US012109412B2

United States Patent
Schmidt et al.

(10) Patent No.: US 12,109,412 B2
(45) Date of Patent: Oct. 8, 2024

(54) COMBINATION ELECTRICAL AND CHEMOTHERAPEUTIC TREATMENT OF CANCER

(71) Applicant: Boston Scientific Scimed, Inc., Maple Grove, MN (US)

(72) Inventors: Brian L. Schmidt, White Bear Lake, MN (US); Benjamin Keith Stein, Shoreview, MN (US); Keith R. Maile, New Brighton, MN (US); Ron A. Balczewski, Bloomington, MN (US); Aleksandra Kharam, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 358 days.

(21) Appl. No.: 16/850,728

(22) Filed: Apr. 16, 2020

(65) Prior Publication Data

US 2020/0330758 A1 Oct. 22, 2020

Related U.S. Application Data

(60) Provisional application No. 62/837,130, filed on Apr. 22, 2019.

(51) Int. Cl.
*A61N 1/36* (2006.01)
*A61B 10/02* (2006.01)
(Continued)

(52) U.S. Cl.
CPC .......... *A61N 1/36002* (2017.08); *A61B 10/02* (2013.01); *A61N 5/0601* (2013.01); *A61P 35/00* (2018.01)

(58) Field of Classification Search
CPC ................................................ A61N 1/36002
See application file for complete search history.

(56) References Cited

U.S. PATENT DOCUMENTS

| 4,016,886 A | 4/1977 | Doss et al. |
| 5,099,838 A | 3/1992 | Bardy |

(Continued)

FOREIGN PATENT DOCUMENTS

| AU | 2005301103 | 5/2006 |
| CN | 101693875 | 4/2010 |

(Continued)

OTHER PUBLICATIONS

"Final Office Action," for U.S. Appl. No. 16/167,140 mailed Dec. 27, 2021 (30 pages).

(Continued)

*Primary Examiner* — William J Levicky
(74) *Attorney, Agent, or Firm* — Pauly, DeVries Smith & Deffner LLC

(57) ABSTRACT

Embodiments herein relate to a method for treating a cancerous tumor located within a subject. The method can include applying one or more electric fields at or near a site of the cancerous tumor, where the cancerous tumor can include a cancerous cell population. The one or more applied electric fields are effective to delay mitosis and cause mitotic synchronization within a proportion of the cancerous cell population. The method can include removing the one or more electric fields to allow mitosis to proceed within the cancerous cell population. The method can include administering a chemotherapeutic agent to the subject after the one or more electric fields have been removed. Other embodiments are also included herein.

13 Claims, 16 Drawing Sheets

(51) Int. Cl.
*A61N 5/06* (2006.01)
*A61P 35/00* (2006.01)

(56) References Cited

U.S. PATENT DOCUMENTS

| | | | |
|---|---|---|---|
| 5,113,869 A | 5/1992 | Nappholz et al. |
| 5,324,328 A | 6/1994 | Li et al. |
| 5,397,342 A | 3/1995 | Heil et al. |
| 5,458,597 A | 10/1995 | Edwards et al. |
| 5,582,609 A | 12/1996 | Swanson et al. |
| 5,630,426 A | 5/1997 | Eggers et al. |
| 5,662,698 A | 9/1997 | Altman et al. |
| 5,834,051 A | 11/1998 | Woloszko et al. |
| 5,871,530 A | 2/1999 | Williams et al. |
| 5,971,530 A | 10/1999 | Hashimoto |
| 6,006,755 A | 12/1999 | Edwards |
| 6,366,808 B1 | 4/2002 | Schroeppel et al. |
| 6,673,623 B1 | 1/2004 | Huberman |
| 6,868,289 B2 | 3/2005 | Palti |
| 6,920,361 B2 | 7/2005 | Williams |
| 7,162,310 B2 | 1/2007 | Doan |
| 7,449,021 B2 | 11/2008 | Underwood et al. |
| 7,524,274 B2 | 4/2009 | Patrick et al. |
| 7,565,205 B2 | 7/2009 | Palti |
| 7,632,235 B1 | 12/2009 | Karicherla et al. |
| 7,656,205 B2 | 2/2010 | Chen et al. |
| 7,715,921 B2 | 5/2010 | Palti |
| 7,720,549 B2 | 5/2010 | Schroeppel et al. |
| 7,805,201 B2 | 9/2010 | Palti |
| 7,809,441 B2 | 10/2010 | Kane et al. |
| 7,890,183 B2 | 2/2011 | Palti et al. |
| 7,917,227 B2 | 3/2011 | Palti |
| 8,002,821 B2 | 8/2011 | Stinson |
| 8,019,414 B2 | 9/2011 | Palti |
| 8,170,648 B2 | 5/2012 | Field et al. |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,483,821 B2 | 7/2013 | Averina et al. |
| 8,500,713 B2 | 8/2013 | Ferek-Petric |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,805,466 B2 | 8/2014 | Salahieh et al. |
| 8,956,352 B2 | 2/2015 | Mauch et al. |
| 9,005,100 B2 | 4/2015 | Gnanashanmugam et al. |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,179,974 B2 | 11/2015 | Ku et al. |
| 9,248,278 B2 | 2/2016 | Crosby et al. |
| 9,283,383 B2 | 3/2016 | Osypka |
| 9,308,039 B2 | 4/2016 | Azure |
| 9,387,323 B2 | 7/2016 | Fleischhacker et al. |
| 9,427,278 B2 | 8/2016 | Swanson |
| 9,440,068 B2 | 9/2016 | Palti et al. |
| 9,474,486 B2 | 10/2016 | Eliason et al. |
| 9,526,911 B1 | 12/2016 | Azure et al. |
| 9,630,022 B2 | 4/2017 | Bourke et al. |
| 9,655,669 B2 | 5/2017 | Palti et al. |
| 9,750,934 B2 | 9/2017 | Palti et al. |
| 9,833,617 B2 | 12/2017 | Travers et al. |
| 9,877,781 B2 | 1/2018 | Grasse et al. |
| 9,910,453 B2 | 3/2018 | Wasserman et al. |
| 10,029,117 B2 | 7/2018 | Bourke |
| 10,238,862 B2 | 3/2019 | Cook et al. |
| 10,265,530 B1 | 4/2019 | Perryman et al. |
| 10,376,177 B2 | 8/2019 | Valvano et al. |
| 10,471,254 B2 | 11/2019 | Sano et al. |
| 11,191,956 B2 | 12/2021 | Giladi et al. |
| 11,331,493 B2 | 5/2022 | Pivonka et al. |
| 11,338,135 B2 | 5/2022 | Schmidt et al. |
| 11,420,049 B2 | 8/2022 | Schmidt et al. |
| 11,607,542 B2 | 3/2023 | Schmidt et al. |
| 11,691,006 B2 | 7/2023 | Schmidt et al. |
| 11,712,561 B2 | 8/2023 | Schmidt et al. |
| 11,850,422 B2 | 12/2023 | Schmidt et al. |
| 11,883,655 B2 | 1/2024 | Srivastava et al. |
| 2001/0044643 A1* | 11/2001 | Litovitz ............ A61N 1/40 607/100 |
| 2002/0026183 A1 | 2/2002 | Simpson |
| 2002/0049485 A1 | 4/2002 | Smits |
| 2002/0065544 A1 | 5/2002 | Smits |
| 2003/0020416 A1 | 1/2003 | Kobayashi |
| 2003/0069623 A1 | 4/2003 | Stypulkowski |
| 2003/0204161 A1 | 10/2003 | Ferek-Petric |
| 2004/0010290 A1 | 1/2004 | Schroeppel et al. |
| 2004/0010303 A1 | 1/2004 | Bolea et al. |
| 2004/0147969 A1 | 7/2004 | Mann et al. |
| 2004/0158288 A1 | 8/2004 | Keisari et al. |
| 2004/0162600 A1 | 8/2004 | Williams |
| 2004/0176804 A1 | 9/2004 | Palti |
| 2004/0215235 A1 | 10/2004 | Jackson et al. |
| 2004/0215296 A1 | 10/2004 | Ganz et al. |
| 2005/0004507 A1 | 1/2005 | Schroeppel et al. |
| 2005/0043894 A1 | 2/2005 | Fernandez |
| 2005/0096584 A1 | 5/2005 | Ferek-petric |
| 2005/0209642 A1* | 9/2005 | Palti ............... A61N 1/40 607/2 |
| 2005/0222623 A1 | 10/2005 | Kroll et al. |
| 2005/0222646 A1 | 10/2005 | Kroll et al. |
| 2005/0240173 A1 | 10/2005 | Palti |
| 2005/0288730 A1 | 12/2005 | Deem et al. |
| 2005/0288761 A1 | 12/2005 | Brabec et al. |
| 2006/0024802 A1 | 2/2006 | Muller et al. |
| 2006/0149341 A1 | 7/2006 | Palti |
| 2006/0190053 A1 | 8/2006 | Dobak |
| 2006/0259092 A1 | 11/2006 | Spadgenske et al. |
| 2006/0259099 A1* | 11/2006 | Goetz ............... A61N 1/37252 607/66 |
| 2006/0282122 A1 | 12/2006 | Palti |
| 2006/0282126 A1 | 12/2006 | Fischbach et al. |
| 2007/0033660 A1 | 2/2007 | Palti |
| 2007/0135861 A1 | 6/2007 | Wallace et al. |
| 2007/0179550 A1 | 8/2007 | Dennis et al. |
| 2007/0225766 A1 | 9/2007 | Palti |
| 2007/0239213 A1 | 10/2007 | Palti |
| 2007/0239244 A1 | 10/2007 | Morgan et al. |
| 2007/0270675 A1 | 11/2007 | Kane et al. |
| 2007/0270916 A1 | 11/2007 | Fischell et al. |
| 2008/0058669 A1 | 3/2008 | Kroll |
| 2008/0058887 A1 | 3/2008 | Griffin et al. |
| 2008/0071350 A1 | 3/2008 | Stinson et al. |
| 2008/0086073 A1 | 4/2008 | McDaniel |
| 2008/0097424 A1 | 4/2008 | Wizeman et al. |
| 2008/0172116 A1 | 7/2008 | Mrva et al. |
| 2008/0195227 A1 | 8/2008 | Boling et al. |
| 2008/0208271 A1 | 8/2008 | Sih et al. |
| 2008/0275524 A1 | 11/2008 | Furness et al. |
| 2009/0076500 A1 | 3/2009 | Azure et al. |
| 2009/0192381 A1 | 7/2009 | Brockway et al. |
| 2009/0234211 A1 | 9/2009 | Li et al. |
| 2010/0016936 A1 | 1/2010 | Stevenson et al. |
| 2010/0168820 A1* | 7/2010 | Maniak ............ A61N 1/37247 607/63 |
| 2010/0198298 A1 | 8/2010 | Schulman et al. |
| 2010/0217356 A1 | 8/2010 | Bikson et al. |
| 2010/0261994 A1 | 10/2010 | Davalos et al. |
| 2010/0298895 A1 | 11/2010 | Ghaffari et al. |
| 2010/0331938 A1 | 12/2010 | Sommer et al. |
| 2011/0071608 A1 | 3/2011 | Fleischhacker et al. |
| 2011/0125215 A1 | 5/2011 | Goetz et al. |
| 2011/0137229 A1 | 6/2011 | Palti et al. |
| 2011/0224665 A1 | 9/2011 | Crosby et al. |
| 2011/0238057 A1 | 9/2011 | Moss et al. |
| 2011/0306878 A1 | 12/2011 | Desimone et al. |
| 2012/0035616 A1 | 2/2012 | Olsen et al. |

(56) References Cited

U.S. PATENT DOCUMENTS

| | | |
|---|---|---|
| 2012/0130444 A1 | 5/2012 | Wei et al. |
| 2012/0158072 A1 | 6/2012 | Venook et al. |
| 2012/0158122 A1 | 6/2012 | Mattson et al. |
| 2012/0203307 A1 | 8/2012 | Schroeppel et al. |
| 2012/0232615 A1 | 9/2012 | Barolat et al. |
| 2012/0283726 A1 | 11/2012 | Palti |
| 2013/0023946 A1 | 1/2013 | Valvano et al. |
| 2013/0165916 A1 | 6/2013 | Mathur et al. |
| 2013/0204068 A1 | 8/2013 | Gnanashanmugam et al. |
| 2013/0261706 A1 | 10/2013 | Mirro et al. |
| 2013/0261711 A1 | 10/2013 | Sivo |
| 2013/0289649 A1 | 10/2013 | Averina et al. |
| 2013/0289664 A1 | 10/2013 | Johanek |
| 2013/0310898 A1 | 11/2013 | Ollivier et al. |
| 2014/0005753 A1 | 1/2014 | Carbunaru |
| 2014/0052227 A1 | 2/2014 | Wahlstrand et al. |
| 2014/0107511 A1 | 4/2014 | Banet et al. |
| 2014/0142670 A1 | 5/2014 | Radhakrishnan et al. |
| 2014/0276781 A1 | 9/2014 | Beani et al. |
| 2014/0276811 A1 | 9/2014 | Koblish et al. |
| 2014/0350541 A1 | 11/2014 | Hill et al. |
| 2014/0350653 A1 | 11/2014 | Shiroff et al. |
| 2015/0005804 A1 | 1/2015 | Franano et al. |
| 2015/0066024 A1 | 3/2015 | Azure |
| 2015/0134022 A1 | 5/2015 | Lee et al. |
| 2015/0180161 A1 | 6/2015 | Olson et al. |
| 2015/0182282 A1 | 7/2015 | Zemel et al. |
| 2015/0320995 A1 | 11/2015 | Nazareth et al. |
| 2015/0374992 A1 | 12/2015 | Crosby et al. |
| 2016/0022986 A1 | 1/2016 | Travers et al. |
| 2016/0029960 A1 | 2/2016 | Toth et al. |
| 2016/0068598 A1 | 3/2016 | Yan et al. |
| 2016/0082258 A1 | 3/2016 | Kramer et al. |
| 2016/0121106 A1 | 5/2016 | Marshall et al. |
| 2016/0128767 A1 | 5/2016 | Azamian et al. |
| 2016/0129276 A1 | 5/2016 | Fried et al. |
| 2016/0250476 A1 | 9/2016 | Kaemmerer et al. |
| 2016/0250483 A1 | 9/2016 | Klimovitch et al. |
| 2016/0331459 A1 | 11/2016 | Townley et al. |
| 2016/0346536 A1* | 12/2016 | Palti ................ A61N 1/32 |
| 2017/0007310 A1 | 1/2017 | Rajagopalan et al. |
| 2017/0035496 A1 | 2/2017 | Nagale et al. |
| 2017/0049514 A1 | 2/2017 | Cosman |
| 2017/0065339 A1 | 3/2017 | Mickelsen |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0215939 A1 | 8/2017 | Palti et al. |
| 2017/0231694 A1 | 8/2017 | Mathur et al. |
| 2017/0251976 A1 | 9/2017 | Schouenborg |
| 2017/0266371 A1 | 9/2017 | Leonhardt et al. |
| 2017/0281934 A1 | 10/2017 | Giladi et al. |
| 2017/0281955 A1 | 10/2017 | Maile et al. |
| 2017/0312501 A1 | 11/2017 | Bornzin et al. |
| 2017/0333702 A1 | 11/2017 | Barner |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0110978 A1 | 4/2018 | Beebe et al. |
| 2018/0154142 A1 | 6/2018 | Guo et al. |
| 2018/0221088 A1 | 8/2018 | Govari et al. |
| 2018/0246079 A1 | 8/2018 | Wang et al. |
| 2018/0256906 A1 | 9/2018 | Pivonka et al. |
| 2018/0289954 A1 | 10/2018 | Hebb et al. |
| 2019/0008555 A1 | 1/2019 | O'Mahony |
| 2019/0117962 A1 | 4/2019 | Chiang et al. |
| 2019/0117969 A1 | 4/2019 | Schmidt et al. |
| 2019/0117970 A1 | 4/2019 | Schmidt et al. |
| 2019/0117971 A1 | 4/2019 | Schmidt et al. |
| 2019/0117972 A1 | 4/2019 | Schmidt et al. |
| 2019/0117973 A1 | 4/2019 | Schmidt et al. |
| 2019/0255344 A1 | 8/2019 | Carter et al. |
| 2019/0262605 A1 | 8/2019 | Babakhani et al. |
| 2019/0321624 A1 | 10/2019 | De Kock et al. |
| 2020/0009377 A1* | 1/2020 | Chang ................ A61N 1/36002 |
| 2020/0061385 A1 | 2/2020 | Schwarz et al. |
| 2020/0330756 A1 | 10/2020 | Schmidt et al. |
| 2020/0330757 A1 | 10/2020 | Schmidt et al. |
| 2020/0338344 A1 | 10/2020 | Schmidt et al. |
| 2020/0338345 A1 | 10/2020 | Schmidt et al. |
| 2020/0338346 A1 | 10/2020 | Schmidt et al. |
| 2021/0260370 A1 | 8/2021 | Srivastava et al. |
| 2021/0339015 A1 | 11/2021 | Dinsmoor et al. |
| 2022/0241586 A1 | 8/2022 | Spehr et al. |
| 2022/0288388 A1 | 9/2022 | Rondoni et al. |
| 2022/0296907 A1 | 9/2022 | Schmidt et al. |
| 2023/0218894 A1 | 7/2023 | Arnholt et al. |
| 2023/0330416 A1 | 10/2023 | Schmidt et al. |
| 2024/0024670 A1 | 1/2024 | Schmidt et al. |
| 2024/0115856 A1 | 4/2024 | Schmidt et al. |
| 2024/0226547 A1 | 7/2024 | Schmidt et al. |

FOREIGN PATENT DOCUMENTS

| | | |
|---|---|---|
| CN | 202365923 | 8/2012 |
| CN | 202844368 | 4/2013 |
| CN | 204698678 | 10/2015 |
| CN | 106823145 | 6/2017 |
| CN | 111263618 | 6/2020 |
| CN | 111263656 | 6/2020 |
| CN | 111278504 | 6/2020 |
| CN | 111432872 | 7/2020 |
| CN | 111465429 | 7/2020 |
| EP | 2942023 | 11/2015 |
| EP | 3700451 | 9/2020 |
| EP | 3700621 | 9/2020 |
| EP | 3700623 | 9/2020 |
| EP | 3700626 | 9/2020 |
| EP | 3700627 | 9/2020 |
| JP | 2011030734 | 2/2011 |
| TW | 201039699 | 11/2010 |
| WO | 9513113 | 5/1995 |
| WO | 9526911 | 10/1995 |
| WO | 9639966 | 12/1996 |
| WO | 0158371 | 8/2001 |
| WO | 0167098 | 9/2001 |
| WO | 2005115535 | 12/2005 |
| WO | 2006047833 | 5/2006 |
| WO | 2008089360 | 7/2008 |
| WO | 2009036457 | 3/2009 |
| WO | 2009036459 | 3/2009 |
| WO | 2013052590 | 4/2013 |
| WO | 2015100451 | 7/2015 |
| WO | 2016065263 | 4/2016 |
| WO | 2016149575 | 9/2016 |
| WO | 2016168485 | 10/2016 |
| WO | 2016179712 | 11/2016 |
| WO | 2016199142 | 12/2016 |
| WO | 2017123981 | 7/2017 |
| WO | 2018207103 | 11/2018 |
| WO | 2019084003 | 5/2019 |
| WO | 2019084011 | 5/2019 |
| WO | 2019084013 | 5/2019 |
| WO | 2019084016 | 5/2019 |
| WO | 2019084021 | 5/2019 |
| WO | 2020219336 | 10/2020 |
| WO | 2020219337 | 10/2020 |
| WO | 2020219339 | 10/2020 |
| WO | 2020219517 | 10/2020 |
| WO | 2020219519 | 10/2020 |
| WO | 2020219521 | 10/2020 |

OTHER PUBLICATIONS

"Non-Final Office Action," for U.S. Appl. No. 16/166,957 mailed Dec. 22, 2021 (39 pages).

"Non-Final Office Action," for U.S. Appl. No. 16/167,087 mailed Dec. 22, 2021 (24 pages).

"Office Action," for Japanese Patent Application No. 2020-542721 mailed Jan. 4, 2022 (2 pages) No English Translation.

(56) References Cited

OTHER PUBLICATIONS

"Response to Communication Pursuant to Art. 94(3) EPC," for European Patent Application No. 18801137.3 filed Jan. 13, 2022 (8 pages).
"Response to Final Rejection," mailed on Nov. 5, 2021 for U.S. Appl. No. 16/855,421, submitted via EFS-Web on Jan. 5, 2022, 11 pages.
"Response to Office Action," for Canadian Patent Application No. 3,079,316 filed Dec. 31, 2021 (15 pages).
"Communication Pursuant to Article 94(3) EPC," for European Patent Application No. 18801138.1 mailed Aug. 29, 2022 (5 pages).
"Decision of Rejection," for Japanese Patent Application No. 2020-542719 mailed Oct. 19, 2021 (3 pages) No English Translation.
"Final Office Action," for U.S. Appl. No. 17/182,436 mailed Jul. 27, 2022 (19 pages).
"International Preliminary Report on Patentability," for PCT Application No. PCT/US2021/019160 mailed Sep. 9, 2022 (10 pages).
"International Search Report and Written Opinion," for PCT Application No. PCT/US2022/021161 mailed Jun. 22, 2022 (15 pages).
"Non-Final Office Action," for U.S. Appl. No. 16/167,087 mailed Sep. 15, 2022 (24 pages).
"Notice of Opposition," for European Patent No. 3700627 filed Aug. 24, 2022 (20 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Response to Final Rejection," mailed on Jul. 5, 2022 for U.S. Appl. No. 16/850,712, submitted via EFS-Web on Sep. 6, 2022, 10 pages.
"Response to Final Rejection," mailed on May 18, 2022 for U.S. Appl. No. 16/166,957, submitted via EFS-Web on Aug. 18, 2022, 14 pages.
"Response to Final Rejection," mailed on May 18, 2022 for U.S. Appl. No. 16/167,087, submitted via EFS-Web on Aug. 18, 2022, 9 pages.
"Response to Final Rejection," mailed on May 27, 2022 for U.S. Appl. No. 16/167,079, submitted via EFS-Web on Aug. 26, 2022, 12 pages.
"Response to Non-Final Rejection," mailed on Jun. 7, 2022 for U.S. Appl. No. 16/855,421, submitted via EFS-Web on Sep. 7, 2022, 9 pages.
"Response to Non-Final Rejection," mailed on May 27, 2022 for U.S. Appl. No. 16/167,140, submitted via EFS-Web on Aug. 25, 2022, 14 pages.
"Response to Non-Final Rejection," mailed on May 27, 2022 for U.S. Appl. No. 16/855,433, submitted via EFS-Web on Aug. 25, 2022, 9 pages.
"Response to Office Action," for Canadian Patent Application No. 3,079,213 filed Aug. 10, 2022 (10 pages).
"Third Office Action," for Japanese Patent Application No. 2020-542721 mailed Aug. 23, 2022 (9 pages) with English translation.
"Response to Final Rejection," mailed on Jul. 5, 2022 and Advisory Action mailed on Sep. 15, 2022 for U.S. Appl. No. 16/850,712, submitted via EFS-Web on Sep. 23, 2022, 10 pages.
"Communication Pursuant to Article 94(3) EPC," for European Patent Application No. 18800411.3 mailed Dec. 22, 2022 (5 pages).
"Non-Final Office Action," for U.S. Appl. No. 16/167,140 Nov. 15, 2022 (29 pages).
"Non-Final Office Action," for U.S. Appl. No. 16/855,433 mailed Nov. 17, 2022 (39 pages).
"Non-Final Office Action," for U.S. Appl. No. 16/855,448 mailed Nov. 7, 2022 (58 pages).
"Non-Final Office Action," for U.S. Appl. No. 17/182,436 mailed Nov. 23, 2022 (19 pages).
"Notice of Allowance," for U.S. Appl. No. 16/855,421 mailed Nov. 16, 2022 (17 pages).
"Office Action," for Canadian Patent Application No. 3,079,213 mailed Dec. 5, 2022 (4 pages).
"Office Action," for Canadian Patent Application No. 3,079,289 mailed Nov. 28, 2022 (7 pages).
"Office Action," for Japanese Patent Application No. 2021-562795 mailed Nov. 15, 2022 (5 pages) with English Translation.
"Office Action," for Japanese Patent Application No. 2021-562798 mailed Nov. 15, 2022 (14 pages), with English translation.
"Response to Non-Final Rejection," mailed on Sep. 15, 2022 for U.S. Appl. No. 16/167,087, submitted via EFS-Web on Dec. 13, 2022, 8 pages.
"Response to Non-Final Rejection," mailed on Sep. 29, 2022 for U.S. Appl. No. 16/166,957, submitted via EFS-Web on Dec. 13, 2022, 16 pages.
"Communication Pursuant to Article 94(3) EPC," for European Patent Application No. 18801138.1 mailed Jun. 7, 2021 (7 pages).
"Examination Report," for Australian Patent Application No. 2018354162 mailed Apr. 21, 2021 (5 pages).
"Examination Report," for Canadian Patent Application No. 3,079,213 mailed Jul. 12, 2021 (4 pages).
"Examination Report," for Canadian Patent Application No. 3,079,282 mailed Jul. 14, 2021 (4 pages).
"Examination Report," for Canadian Patent Application No. 3,079,314 mailed Jul. 14, 2021 (4 pages).
"Final Office Action," for U.S. Appl. No. 16/166,957 mailed May 14, 2021 (33 pages).
"Final Office Action," for U.S. Appl. No. 16/167,079 mailed Jun. 23, 2021 (34 pages).
"Final Office Action," for U.S. Appl. No. 16/167,087 mailed Aug. 2, 2021 (25 pages).
"First Office Action," for Chinese Patent Application No. 201880068896.3 mailed Apr. 13, 2021 (17 pages) with English Summary.
"International Search Report and Written Opinion," for PCT Application No. PCT/US2021/019160 mailed Jun. 2, 2021 (15 pages).
"Non-Final Office Action," for U.S. Appl. No. 16/167,087 mailed Mar. 31, 2021 (28 pages).
"Non-Final Office Action," for U.S. Appl. No. 16/167,140 mailed Jul. 12, 2021 (32 pages).
"Non-Final Office Action," for U.S. Appl. No. 16/855,421 mailed May 28, 2021 (37 pages).
"Office Action," for Canadian Patent Application No. 3,079,289 mailed May 28, 2021 (4 pages).
"Office Action," for Japanese Patent Application No. 2020-542719 mailed Jun. 1, 2021 (9 pages) with English Translation.
"Office Action," for Japanese Patent Application No. 2020-542720 mailed May 11, 2021 (13 pages) with English Translation.
"Response to Examination Report," for Australian Patent Application No. 2018354162 filed Jul. 13, 2021 (18 pages).
"Response to Examination Report," for Australian Patent Application No. 2018354162 filed Mar. 30, 2021 (15 pages).
"Response to Final Rejection," mailed on May 14, 2021 for U.S. Appl. No. 16/166,957, submitted via EFS-Web on Aug. 5, 2021, 18 pages.
"Response to Non-Final Rejection," mailed on Jan. 6, 2021 for U.S. Appl. No. 16/267,079, submitted via EFS-Web on Apr. 6, 2021, 19 pages.
"Response to Non-Final Rejection," mailed on Mar. 31, 2021 for U.S. Appl. No. 16/167,087, submitted via EFS-Web on Jun. 23, 2021, 12 pages.
"Response to Second Examination Report," for Australian Patent Application No. 2018354149 filed Apr. 13, 2021 (19 pages).
"Communication Pursuant to Article 94(3) EPC," for European Patent Application No. 18801137.3 mailed Sep. 15, 2021 (4 pages).
"Decision of Rejection," for Japanese Patent Application No. 2020-54219 mailed Oct. 19, 2021 (6 pages) with English Translation.
"Final Office Action," for U.S. Appl. No. 16/850,720 mailed Nov. 15, 2021 (15 pages).
"Final Office Action," for U.S. Appl. No. 16/855,421 mailed Nov. 5, 2021 (25 pages).
"First Office Action," for Chinese Patent Application No. 201880078117.8 mailed Jul. 20, 2021 (14 pages) with English Summary.
"International Preliminary Report on Patentability," for PCT Application No. PCT/US2020/028508 mailed Nov. 4, 2021 (8 pages).
"International Preliminary Report on Patentability," for PCT Application No. PCT/US2020/028509 mailed Nov. 4, 2021 (9 pages).

(56) References Cited

OTHER PUBLICATIONS

"International Preliminary Report on Patentability," for PCT Application No. PCT/US2020/028512 mailed Nov. 4, 2021 (8 pages).
"International Preliminary Report on Patentability," for PCT Application No. PCT/US2020/029270 mailed Nov. 4, 2021 (11 pages).
"International Preliminary Report on Patentability," for PCT Application No. PCT/US2020/029274 mailed Nov. 4, 2021 (13 pages).
"International Preliminary Report on Patentability," for PCT Application No. PCT/US2020/029277 mailed Nov. 4, 2021 (10 pages).
"Non-Final Office Action," for U.S. Appl. No. 16/167,116 mailed Sep. 3, 2021 (29 pages).
"Non-Final Office Action," for U.S. Appl. No. 16/850,720 mailed Aug. 24, 2021 (32 pages).
"Non-Final Office Action," for U.S. Appl. No. 16/855,433 mailed Sep. 8, 2021 (32 pages).
"Office Action," for Canadian Patent Application No. 3,079,316 mailed Oct. 27, 2021 (4 pages).
"Office Action," for Japanese Patent Application No. 2020-542718 mailed Oct. 19, 2021 (3 pages) No English Translation.
"Office Action," for Japanese Patent Application No. 2020-542722 mailed Oct. 26, 2021 (9 pages) with English Translation.
"Response to Communication Pursuant to Article 94(3) EPC," for European Patent Application No. 18801138.1 filed Oct. 15, 2021 (10 pages).
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Final Rejection mailed on," Aug. 2, 2021 for U.S. Appl. No. 16/167,087, submitted via EFS-Web on Nov. 1, 2021, 12 pages.
"Response to Final Rejection," mailed on Jun. 23, 2021 and the Advisory Action mailed on Oct. 15, 2021 for U.S. Appl. No. 16/167,079, submitted via EFS-Web on Oct. 21, 2021, 19 pages.
"Response to Final Rejection," mailed on Jun. 23, 2021 for U.S. Appl. No. 16/167,079, submitted via EFS-Web on Sep. 9, 2021, 16 pages.
"Response to Final Rejection," mailed on May 14, 2021 and Advisory Action mailed on Aug. 26, 2021 for U.S. Appl. No. 16/166,957, submitted via EFS-Web on Sep. 10, 2021.
"Response to Non-Final Rejection," mailed on Aug. 24, 2021 for U.S. Appl. No. 16/850,720, submitted via EFS-Web on Nov. 1, 2021, 11 pages.
"Response to Non-Final Rejection," mailed on Jul. 12, 2021 for U.S. Appl. No. 16/167,140, submitted via EFS-Web on Oct. 12, 2021, 16 pages.
"Response to Non-Final Rejection," mailed on May 28, 2021 for U.S. Appl. No. 16/855,421, submitted via EFS-Web on Aug. 20, 2021, 11 pages.
"Response to Non-Final Rejection," mailed on Sep. 3, 2021 for U.S. Appl. No. 16/167,116, submitted via EFS-Web on Nov. 2, 2021, 14 pages.
"Response to Non-Final Rejection," mailed on Sep. 8, 2021 for U.S. Appl. No. 16/855,433, submitted via EFS-Web on Nov. 2, 2021, 12 pages.
"Response to Office Action," for Canadian Patent Application No. 3,079,314 filed Nov. 12, 2021 (14 pages).
"Response to Office Action," for Canadian Patent Application No. 3,079,289 filed with CIPO Sep. 23, 2021 (17 pages).
"Second Office Action," for Chinese Patent Application No. 201880068896.3 Oct. 20, 2021 (6 pages), no English translation.
"Non-Final Office Action," for U.S. Appl. No. 16/167,079 mailed Feb. 17, 2022 (37 pages).
"Office Action," for Canadian Patent Application No. 3,079,289 mailed Mar. 24, 2022 (8 pages).
"Response to Final Rejection," mailed on Dec. 27, 2021 and Advisory Action mailed on Mar. 9, 2022 for U.S. Appl. No. 16/167,140, submitted via EFS-Web on Mar. 25, 2022, 11 pages.
"Response to Final Rejection," mailed on Nov. 5, 2021 and Advisory Action mailed on Feb. 9, 2022 for U.S. Appl. No. 16/855,421, submitted via EFS-Web on Mar. 4, 2022, 11 pages.
"Response to Non-Final Rejection," mailed on Dec. 22, 2021 for U.S. Appl. No. 16/166,957, submitted via EFS-Web on Mar. 22, 2022, 13 pages.
"Response to Non-Final Rejection," mailed on Dec. 22, 2021 for U.S. Appl. No. 16/167,087, submitted via EFS-Web on Mar. 22, 2022, 9 pages.
"Response to Non-Final Rejection," mailed on Feb. 1, 2022 for U.S. Appl. No. 17/182,436, submitted via EFS-Web on Mar. 21, 2022, 8 pages.
"Response to Non-Final Rejection," mailed on Jan. 21, 2022 for U.S. Appl. No. 16/850,712, submitted via EFS-Web on Mar. 21, 2022, 10 pages.
"Final Office Action," for U.S. Appl. No. 16/166,957 mailed May 18, 2022 (35 pages).
"Final Office Action," for U.S. Appl. No. 16/167,079 mailed May 27, 2022 (29 pages).
"Final Office Action," for U.S. Appl. No. 16/167,087 mailed May 18, 2022 (26 pages).
"Final Office Action," for U.S. Appl. No. 16/850,712 mailed Jul. 5, 2022 (16 pages).
"Non-Final Office Action," for U.S. Appl. No. 16/167,140 May 27, 2022 (25 pages).
"Non-Final Office Action," for U.S. Appl. No. 16/855,421 mailed Jun. 7, 2022 (21 pages).
"Non-Final Office Action," for U.S. Appl. No. 16/855,433 mailed May 27, 2022 (18 pages).
"Notice of Allowance," for U.S. Appl. No. 16/850,720 mailed Apr. 14, 2022 (17 pages).
"Office Action," for Canadian Patent Application No. 3,079,213 mailed Apr. 20, 2022 (6 pages).
"Office Action," for Canadian Patent Application No. 3,079,314 mailed Apr. 29, 2022 (3 pages).
"Office Action," for Canadian Patent Application No. 3,079,316 mailed Jun. 3, 2022 (3 pages).
"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20727417.6 filed Jun. 1, 2022 (8 pages).
"Response to Communication Pursuant to Rules 161(1) and 162 EPC," for European Patent Application No. 20724333.8 filed Jun. 8, 2022 (8 pages).
"Response to Final Rejection," mailed on Feb. 1, 2022 for U.S. Appl. No. 16/855,433, submitted via EFS-Web on May 2, 2022, 9 pages.
"Response to Non-Final Rejection," mailed on Feb. 17, 2022 for U.S. Appl. No. 16/167,079, submitted via EFS-Web on May 3, 2022, 11 pages.
Notice of Opposition for European Patent Application No. 18801134.0 on behalf of Novocure Gmbh, mailed Jun. 28, 2022 (36 pages).
"Final Office Action," for U.S. Appl. No. 16/855,433 mailed Feb. 1, 2022 (20 pages).
"Non-Final Office Action," for U.S. Appl. No. 16/850,712 mailed Jan. 21, 2022 (40 pages).
"Non-Final Office Action," for U.S. Appl. No. 17/182,436 mailed Feb. 1, 2022 (41 pages).
"Notice of Allowance," for U.S. Appl. No. 16/167,116 mailed Jan. 26, 2022 (19 pages).
"Response to Final Rejection," mailed on Dec. 27, 2021 for U.S. Appl. No. 16/167,140, submitted via EFS-Web on Feb. 9, 2022, 9 pages.

(56) References Cited

OTHER PUBLICATIONS

"Response to Final Rejection," mailed on Nov. 15, 2021 for U.S. Appl. No. 16/850,720, submitted via EFS-Web on Feb. 11, 2022, 12 pages.
"Optune®—Elevate Expectations / Patient Information and Operation Manual," Novocure™, www.optune.com, 46, pages, Jan. 2019.
Di Sebastiano, Andrea R et al., "Preclinical Outcomes of Intratumoral Modulation Therapy for Glioblastoma," Scientific Reports (2018) 8:7301 (11 pages).
File History for U.S. Appl. No. 16/166,957, filed Dec. 28, 2020 (427 pages).
File History for U.S. Appl. No. 16/167,079, filed Dec. 28, 2020 (301 pages).
File History for U.S. Appl. No. 16/167,087, filed Dec. 28, 2020 (310 pages).
File History for U.S. Appl. No. 16/167,116, filed Dec. 28, 2020 (238 pages).
File History for U.S. Appl. No. 16/167, 140, filed Dec. 28, 2020 (231 pages).
"First Examination Report," for Australian Patent Application No. 2018354149 mailed Jul. 29, 2020 (5 pages).
"First Examination Report," for Australian Patent Application No. 2018354157 mailed Jul. 31, 2020 (5 pages).
"First Examination Report," for Australian Patent Application No. 2018354159 mailed Aug. 12, 2020 (5 pages).
"First Examination Report," for Australian Patent Application No. 2018354162 mailed Sep. 29, 20 (8 pages).
"First Examination Report," for Australian Patent Application No. 2018354167 mailed Sep. 14, 2020 (5 pages).
"International Preliminary Report on Patentability," for PCT Application No. PCT/US2018/057104 mailed May 7, 2020 (8 pages).
"International Preliminary Report on Patentability," for PCT Application No. PCT/US2018/057115 mailed May 7, 2020 (9 pages).
"International Preliminary Report on Patentability," for PCT Application No. PCT/US2018/057117 mailed May 7, 2020 (8 pages).
"International Preliminary Report on Patentability," for PCT Application No. PCT/US2018/057120 mailed May 7, 2020 (8 pages).
"International Preliminary Report on Patentability," for PCT Application No. PCT/US2018/057127 mailed May 7, 2020 (8 pages).
"International Search Report and Written Opinion," for PCT Application No. PCT/US2018/057104 mailed Dec. 20, 2018 (14 pages).
"International Search Report and Written Opinion," for PCT Application No. PCT/US2018/057115 mailed Jan. 4, 2019 (13 pages).
"International Search Report and Written Opinion," for PCT Application No. PCT/US2018/057117 mailed Dec. 20, 2018 (14 pages).
"International Search Report and Written Opinion," for PCT Application No. PCT/US2018/057120 mailed Dec. 19, 2018 (14 pages).
"International Search Report and Written Opinion," for PCT Application No. PCT/US2018/057127 mailed Jan. 18, 2019 (12 pages).
"International Search Report and Written Opinion," for PCT Application No. PCT/US2020/028508 mailed Aug. 3, 2020 (13 pages).
"International Search Report and Written Opinion," for PCT Application No. PCT/US2020/028509 mailed Jun. 30, 2020 (15 pages).
"International Search Report and Written Opinion," for PCT Application No. PCT/US2020/028512 mailed Jul. 13, 2020 (14 pages).
"International Search Report and Written Opinion," for PCT Application No. PCT/US2020/029270 mailed Oct. 26, 2020 (19 pages).
"International Search Report and Written Opinion," for PCT Application No. PCT/US2020/029274 mailed Aug. 28, 2020 (19 pages).
"International Search Report and Written Opinion," for PCT Application No. PCT/US2020/029277 mailed Jul. 13, 2020 (15 pages).
"Invitation to Pay Additional Fees," for PCT Application No. PCT/US2020/029270 mailed Aug. 28, 2020 (14 pages).
"Invitation to Pay Additional Fees," for PCT Application No. PCT/US2020/029274 mailed Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
"Novocure Announces Launch of the inovitro™," Laboratory Research System, Press Release, 2 pages, Nov. 21, 2013., 2 pages.
"Response to Communication Pursuant to Rules 161(1) and 162 EPC," for European Patent Application No. 18800411.3 filed Dec. 9, 2020 (11 pages).
"Response to Communication Pursuant to Rules 161(1) and 162 EPC," for European Patent Application No. 18801134.0 filed Dec. 11, 2020 (9 pages).
"Response to Communication Pursuant to Rules 161(1) and 162 EPC," for European Patent Application No. 18801136.5 filed Dec. 10, 2020 (8 pages).
"Response to Communication Pursuant to Rules 161(1) and 162 EPC," for European Patent Application No. 18801137.3 filed Dec. 10, 2020 (7 pages).
"Response to Communication Pursuant to Rules 161(1) and 162 EPC," for European Patent Application No. 18801138.1 filed Dec. 11, 2020 (16 pages).
"Response to Examination Report," for Australian Patent Application No. 2018354149 filed Dec. 21, 2020 (14 pages).
"Response to Examination Report," for Australian Patent Application No. 2018354157 filed Dec. 31, 2020 (17 pages).
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
Xu, Hu et al., "In Vitro Validation of Intratumoral Modulation Therapy for Glioblastoma," Anticancer Research 36:71-80 (2016), 10 pages.
"Communication Pursuant to Article 94(3) EPC," for European Patent Application No. 18801137.3 mailed Mar. 5, 2021 (4 pages).
"Examination Report," for Australian Patent Application No. 2018354162 mailed Feb. 4, 2021 (5 pages).
"Final Office Action," for U.S. Appl. No. 16/167,116 mailed Jan. 21, 2021 (25 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
"Non-Final Office Action," for U.S. Appl. No. 16/166,957 mailed Feb. 17, 2021 (37 pages).
"Non-Final Office Action," for U.S. Appl. No. 16/167,079 mailed Jan. 6, 2021 (28 pages).
"Office Action," for Japanese Patent Application No. 2020-542718 mailed Feb. 9, 2021 11 pages) with English Translation.
"Office Action," for Japanese Patent Application No. 2020-542721 mailed Feb. 9, 2021 (10 pages) with English Summary.
"Office Action," for Japanese Patent Application No. 2020-542722 mailed Feb. 9, 2021 (5 pages) with English Summary.
"Response to Examination Report," for Australian Patent Application No. 2018354159 filed Jan. 18, 2021 (21 pages).
"Response to Examination Report," for Australian Patent Application No. 2018354162 filed Jan. 28, 2021 (15 pages).
"Response to Examination Report," for Australian Patent Application No. 2018354167 filed Jan. 28, 2021 (17 pages).
"Response to Final Rejection," mailed on Jan. 21, 2021 for U.S. Appl. No. 16/167,116, submitted via EFS-Web on Mar. 2, 2021, 12 pages.
"Response to Final Rejection," mailed on Oct. 13, 2020 for U.S. Appl. No. 16/167,087, 11 pages, submitted via EFS-Web on Jan. 13, 2021.
"Response to Final Rejection," mailed on Oct. 19, 2020 for U.S. Appl. No. 16/167,140, submitted via EFS-Web on Jan. 19, 2021, 16 pages.
"Response to Non-Final Rejection," mailed on Feb. 17, 2021 for U.S. Appl. No. 16/166,957, submitted via EFS-Web on Mar. 17, 2021, 17 pages.
"Response to Non-Final Rejection," mailed on Oct. 7, 2020 for U.S. Appl. No. 16/167,116, submitted via EFS-Web on Jan. 6, 2021, 13 pages.
"Second Examination Report," for Australian Patent Application No. 2018354149 mailed Jan. 8, 2021 (4 pages).
"First Office Action," for Chinese Patent Application No. 201880068897.8 mailed Sep. 21, 2022 (11 pages) with English Summary.
"Non-Final Office Action," for U.S. Appl. No. 16/166,957 mailed Sep. 29, 2022 (41 pages).

(56) References Cited

OTHER PUBLICATIONS

"Non-Final Office Action," for U.S. Appl. No. 16/850,712 mailed Oct. 6, 2022 (11 pages).
"Response to Final Rejection," mailed on Jul. 22, 2022 with Request for Continued Examination, for U.S. Appl. No. 17/182,436, submitted via EFS-Web on Sep. 29, 2022, 9 pages.
"Response to Final Rejection," mailed on Jul. 27, 2022 for U.S. Appl. No. 17/182,436, submitted via EFS-Web on Sep. 27, 2022, 9 pages.
"Decision of Rejection," for Japanese Patent Application No. 2021-562795 mailed Mar. 28, 2023 (6 pages) with English translation.
"Final Office Action," for Japanese Patent Application No. 2020-542721 mailed Mar. 7, 2023 (5 pages) with English translation.
"Final Office Action," for U.S. Appl. No. 16/855,433 mailed May 3, 2023 (25 pages).
"First Office Action," for Chinese Patent Application No. 201880078118.2 mailed Mar. 27, 2023 (17 pages) with English translation.
"International Search Report and Written Opinion," for PCT Application No. PCT/US2023/010469 mailed Apr. 12, 2023 (19 pages).
"Response to Communication Pursuant to Article 94(3) EPC," for European Patent Application No. 18800411.3 filed May 2, 2023 (11 pages).
"Communication Pursuant to Article 94(3) EPC," for European Patent Application No. 20724333.8 mailed Mar. 17, 2023 (6 pages).
"Final Office Action," for U.S. Appl. No. 16/166,957 mailed Mar. 7, 2023 (49 pages).
"Final Office Action," for U.S. Appl. No. 16/167,087 mailed Mar. 6, 2023 (30 pages).
"Non-Final Office Action," for U.S. Appl. No. 16/167,079 mailed Mar. 23, 2023 (40 pages).
"Notice of Allowance," for U.S. Appl. No. 16/850,712 Mailed Feb. 7, 2023 (14 pages).
"Notice of Allowance," for U.S. Appl. No. 16/855,448 mailed Mar. 8, 2023 (19 pages).
"Office Action," for Japanese Patent Application No. 2021-562797 mailed Nov. 22, 2022 (9 pages), with English Translation.
"Office Action," for Japanese Patent Application No. 2021-562966 mailed Nov. 29, 2022 (11 pages) with English Translation.
"Office Action," for Japanese Patent Application No. 2021-562972 mailed Nov. 8, 2022 (26 pages) with English Translation.
"Response to Communication Pursuant to Article 94(3) EPC," for European Patent Application No. 18801138.1 filed Mar. 8, 2023 (10 pages).
"Response to Communication Pursuant to Rules 161(1) and 162 EPC," for European Patent Application No. 21712639.0 filed Jan. 20, 2023 (26 pages).
"Response to Non-Final Rejection," for U.S. Appl. No. 16/855,433, mailed on Nov. 17, 2022, submitted via EFS-Web on Feb. 17, 2023, 11 pages.
"Response to Non-Final Rejection," mailed on Nov. 15, 2022, based on U.S. Appl. No. 16/167,140, submitted via EFS- Web on Feb. 15, 2023, 12 pages.
"Response to Non-Final Rejection," mailed on Nov. 23, 2022 for U.S. Appl. No. 17/182,436, submitted via EFS-Web on Feb. 23, 2023, 11 pages.
"Response to Non-Final Rejection," mailed on Nov. 7, 2022 for U.S. Appl. No. 16/855,448, submitted via EFS-Web on Feb. 7, 2023, 9 pages.
"Response to Non-Final Rejection," mailed on Oct. 6, 2022 for U.S. Appl. No. 16/850,712, submitted via EFS-Web on Jan. 4, 2023, 10 pages.
"Response to Office Action," for Canadian Patent Application No. 3,079,213 filed Mar. 8, 2023 (6 pages).
"Response to Office Action," for Canadian Patent Application No. 3,079,289 filed Mar. 24, 2023 (18 pages).
"Second Office Action," for Chinese Patent Application No. 201880068897.8 mailed Feb. 27, 2023 (9 pages) with English Summary.
"Final Office Action," for U.S. Appl. No. 16/167,140 mailed May 24, 2023 (41 pages).
"Final Office Action," for U.S. Appl. No. 17/182,436 mailed May 19, 2023 (22 pages).
"First Office Action," for Chinese Patent Application No. 201880068852.0 mailed Mar. 15, 2023 (9 pages).
"Response to Final Rejection," mailed Mar. 6, 2023 for U.S. Appl. No. 16/167,087, submitted via EFS-Web on Jun. 6, 2023, 10 pages.
"Response to Final Rejection," mailed on Mar. 7, 2023 for U.S. Appl. No. 16/166,957, submitted via EFS-Web on Jun. 7, 2023, 18 pages.
"Second Office Action," for Japanese Patent Application No. 2021-562798 mailed May 9, 2023 (11 pages) with English translation.
"First Office Action," for Chinese Patent Application No. 202080030771.9 mailed Nov. 15, 2023 (7 pages) with English summary.
"Fourth Office Action," for Chinese Patent Application No. 201880068897.8 mailed Oct. 17, 2023 (13 pages) with English Summary.
"Non-Final Office Action," for U.S. Appl. No. 16/166,957 mailed Nov. 14, 2023 (39 pages).
"Response to Communication Pursuant to Article 94(3) EPC," for European Patent Application No. 18801138.1 filed Nov. 16, 2023 (76 pages).
"Response to Final Rejection," mailed on Sep. 14, 2023, for U.S. Appl. No. 16/167,079, submitted via EFS-Web on Dec. 14, 2023, 14 pages.
"Response to Non-Final Rejection," mailed on Oct. 11, 2024, for U.S. Appl. No. 16/167,140, submitted via EFS-Web on Jan. 11, 2024, 12 pages.
"Response to Non-Final Rejection," mailed on Sep. 19, 2023, for U.S. Appl. No. 16/167,087, submitted via EFS- Web on Dec. 19, 2023, 13 pages.
"Response to Office Action," for Canadian Patent Application No. 3,079,289 filed Nov. 3, 2023 (13 pages).
"Written Submissions," as filed in response to Summons to Attend Oral Proceedings for European Patent Application No. 18801134.0 filed Dec. 20, 2023 (137 pages).
"Communication Pursuant to Article 94(3) EPC," for European Patent Application No. 18801138.1 mailed Jul. 7, 2023 (5 pages).
"Decision of Rejection," for Japanese Patent Application No. 2021-562797 mailed May 16, 2023 (10 pages), with English translation.
"Final Office Action," for U.S. Appl. No. 16/167,079 mailed Sep. 14, 2023 (33 pages).
"Non-Final Office Action," for U.S. Appl. No. 16/167,087 mailed Sep. 19, 2023 (38 pages).
"Notice of Allowance," for U.S. Appl. No. 16/855,433 mailed Aug. 23, 2023 (6 pages).
"Notice of Allowance," for U.S. Appl. No. 17/182,436 mailed Sep. 15, 2023 (17 pages).
"Office Action," for Canadian Patent Application No. 3,079,289 mailed Jul. 6, 2023 (3 pages).
"Office Action," for Japanese Patent Application No. 2021-562972 mailed May 5, 2023 (12 pages), with English translation.
"Response to Communication Pursuant to Article 94(3) EPC," for European Patent Application No. 20724333.8 filed Jul. 25, 2023 (28 pages).
"Response to Final Office Action," mailed May 24, 2023, and Advisory Action mailed Sep. 20, 2023, for U.S. Appl. No. 16/167,140, submitted via EFS-Web on Sep. 25, 2023, 12 pages.
"Response to Final Rejection," mailed on May 19, 2023, for U.S. Appl. No. 17/182,436, submitted via EFS-Web on Aug. 21, 2023, 14 pages.
"Response to Final Rejection," mailed on May 24, 2023, for U.S. Appl. No. 16/167,140, submitted via EFS-Web on Aug. 24, 2023, 11 pages.
"Response to Final Rejection," mailed on May 3, 2023, for U.S. Appl. No. 16/855,433, submitted via EFS-Web on Aug. 2, 2023, 10 pages.
"Response to Non-Final Rejection," mailed on Mar. 23, 2023 for U.S. Appl. No. 16/167,079, submitted via EFS-Web on Jun. 23, 2023, 12 pages.

(56) References Cited

OTHER PUBLICATIONS

"Second Office Action," for Japanese Patent Application No. 2021-562966 mailed Jun. 13, 2023 (9 pages), with English translation.
"Summons to Attend Oral Proceedings," for European Patent Application No. 18801136.5 mailed Sep. 12, 2023 (13 pages).
"Supplemental Response to," Final Rejection mailed on Mar. 6, 2023, for U.S. Appl. No. 16/167,087, submitted via EFS-Web on Aug. 31, 2023, 7 pages.
"Third Office Action," for Chinese Patent Application No. 201880068897.8 mailed Jun. 9, 2023 (10 pages) with English Summary.
"Zenchi Examination Report," for Japanese Patent Application No. 2021-562795 mailed Aug. 2, 2023 (9 pages) with English Summary.
"Decision of Rejection," for Japanese Patent Application No. 2021-562972 mailed Sep. 5, 2023 (10 pages) with English Translation.
"International Preliminary Report on Patentability," for PCT Application No. PCT/US2022/021161 mailed Oct. 5, 2023 (9 pages).
"Non-Final Office Action," for U.S. Appl. No. 16/167,140 mailed Oct. 11, 2023 (32 pages).
"Office Action," for Japanese Patent Application No. 2021-562798 mailed Aug. 22, 2023 (4 pages) with English translation.
"Decision of Rejection," for Japanese Patent Application No. 2021-562966 mailed Dec. 26, 2023 (9 pages), with English translation.
"Fifth Office Action," for Chinese Patent Application No. 201880068897.8 mailed Feb. 8, 2024 (8 pages) with English summary.
"Final Office Action," for U.S. Appl. No. 16/167,140 mailed Feb. 7, 2024 (42 pages).
"Non-Final Office Action," for U.S. Appl. No. 17/698,516 mailed Feb. 23, 2024 (69 pages).
"Response to Non-Final Rejection," mailed on Nov. 14, 2024, for U.S. Appl. No. 16/166,957, submitted via EFS-Web on Feb. 14, 2024, 15 pages.
"Second Office Action," for Chinese Patent Application No. 201880078118.2 mailed Jan. 12, 2024 (17 pages) with English translation.
"Extended European Search Report," for European Patent Application No. 24171838.6 mailed May 8, 2024 (6 pages).
"Final Office Action," for U.S. Appl. No. 16/167,087 mailed Apr. 1, 2024 (38 pages).
"Final Rejection Action," for Chinese Patent Application No. 201880078118.2 mailed Mar. 28, 2024 (10 pages) with English translation, 12 pages.
"First Office Action," for Chinese Patent Application No. 202080030415.7 mailed Mar. 6, 2024 (13 pages) with English translation.
"First Office Action," for Chinese Patent Application No. 202080030769.1 mailed Dec. 29, 2023, with English summary (12 pages).
"First Office Action," for Chinese Patent Application No. 202080030850.X mailed Mar. 29, 2024 (14 pages) with English translation.
"First Office Action," for Chinese Patent Application No. 202080030856.7 mailed Mar. 16, 2024 (11 pages) with English translation.
"Non-Final Office Action," for U.S. Appl. No. 16/167,079 mailed Apr. 25, 2024 (34 pages).
"Non-Final Office Action," for U.S. Appl. No. 18/123,776 mailed Mar. 20, 2024 (40 pages).
"Response to Final Rejection," mailed on Feb. 7, 2024, for U.S. Appl. No. 16/167,140, submitted via EFS-Web on May 7, 2024, 12 pages.
"Second Office Action," for Chinese Patent Application No. 201880068852.0 mailed Jan. 15, 2024 (19 pages) with English summary.
Chen, Yu, et al. "Synergistic chemo-photodynamic therapy mediated by light-activated ROS-degradable nanocarriers.," Synergistic chemo-photodynamic therapy mediated by light-activated ROS-degradable nanocarriers. J. Mater. Chem. B, 2019, 7, 460-468. Apr. 12, 2018 (Chen et al) https://pubs.rsc.org/en/content/articlelanding/20 1 9/tb/c8tb03030h, 460-468.
"Communication Pursuant to Article 94(3) EPC," for European Patent Application No. 20724703.2 mailed Jun. 4, 2024 (7 pages).
"Extended European Search Report," for European Patent Application No. 24159633.7 mailed Jun. 14, 2024 (7 pages).
"Extended European Search Report," for European Patent Application No. 24171875.8 mailed Jul. 16, 2024 (8 pages).
"Final Office Action," for U.S. Appl. No. 17/698,516 mailed Aug. 19, 2024 (25 pages).
"Final Rejection Action," for Chinese Patent Application No. 201880068852.0 mailed Jun. 7, 2024 (16 pages) with English Summary.
"International Preliminary Report on Patentability," for PCT Patent Application No. PCT/US2023/010469 mailed Jul. 25, 2024 (12 pages).
"Non-Final Office Action," for U.S. Appl. No. 18/215,603 mailed Jul. 18, 2024, 64 pages.
"Office Action," for Japanese Patent Application No. 2021-562795 mailed Jun. 18, 2024 (8 pages) with English translation.
"Response to Final Rejection," mailed Feb. 7, 2024, and the Advisory Action mailed on Jun. 4, 2024, for U.S. Appl. No. 16/167,140, submitted via EFS-Web on Jul. 2, 2024, 14 pages.
"Response to Final Rejection," mailed on May 31, 2024, for U.S. Appl. No. 16/166,957, submitted via EFS-Web on Aug. 30, 2024, 18 pages.
"Response to Non-Final Rejection," mailed on Apr. 25, 2024, for U.S. Appl. No. 16/167,079, submitted via EFS-Web on Jul. 25, 2024, 16 pages.
"Response to Non-Final Rejection," mailed on Mar. 20, 2024, for U.S. Appl. No. 18/123,776, submitted via EFS-Web on Jun. 20, 2024, 8 pages.
"Second Office Action," for Chinese Patent Application No. 202080030769.1 mailed Jul. 4, 2024 (13 pages) with English translation.
"Supplemental Amendment," filed in response to Non-Final Rejection mailed Mar. 20, 2024, for U.S. Appl. No. 18/123,776, submitted via Patent center on Aug. 30, 2024, 12 pages.
"Zenchi Examination Report," for Japanese Patent Application No. 2021-562966 mailed Aug. 6, 2024 (3 pages) with English Translation.

\* cited by examiner

COMBINATION ELECTRICAL AND CHEMOTHERAPEUTIC TREATMENT OF CANCER

This application claims the benefit of U.S. Provisional Application No. 62/837,130, filed Apr. 22, 2019, the content of which is herein incorporated by reference in its entirety.

FIELD

Embodiments herein relate to methods, devices, and systems for the treatment of a cancerous tumor using one or more of an electrical and/or chemotherapeutic modalities.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

All actively dividing somatic cells undergo cellular division through the cell cycle, including many types of cancerous cells. Actively dividing cells move through two main phases of the cell cycle: interphase and the M phase. During interphase, the longest phase of the cell cycle, an individual cell begins doubling in size and replicating its DNA in preparation for cellular division. Interphase can be broken down into three discrete phases in the following order: the gap phase 1, or G1 phase; the synthesis phase, or S phase; and the gap phase 2, or G2 phase. In the G1 phase, the all of the cellular contents except for the chromosomes are duplicated and the cell begins to double its size. During the S phase, DNA synthesis replicates the chromosomes to form two sister chromatids for each chromosome in the cell. During the G2 phase, the cell continues its growth and prepares the cell and chromosomes for the M phase.

During the M phase, the cell exits interphase and begins the process of mitosis, or nuclear division, which includes separation of the sister chromatids. The M phase ends with cytokinesis, or cytoplasmic division. Mitosis includes four basic phases: prophase, metaphase, anaphase, and telophase. During prophase, the chromosomes start to condense and the nuclear membrane surrounding the nucleus disappears. The mitotic spindle also begins to form during prophase. The mitotic spindle includes a self-organized bipolar array of microtubules and centrosomes. Microtubules are generally formed from the polymerization of the highly polar alpha-tubulin and beta-tubulin proteins. Centrosomes are similarly protein-based organelles, two of which migrate to opposite sides of the dividing cell at this phase. The negatively charged end of the microtubules attach to the centrosomes. The positively charged end of the microtubules radiate toward the equator of the dividing cell where they eventually attach to a kinetochore of each sister chromatid. Metaphase can be defined by all chromosomes being aligned at the equator of the dividing cell and bound in the mitotic spindle. An equal number of sister chromatids are then pulled toward opposite ends of the cell during anaphase. Once all chromosomes have been separated, the process of telophase begins, where the cell membrane begins to form a cleavage furrow between the two newly forming sister cells, and cell division becomes complete once the cells physically separate from one another in a process called cytokinesis.

SUMMARY

In a first aspect, a method for treating a cancerous tumor located within a subject is included. The method can include applying one or more electric fields at or near a site of the cancerous tumor, where the cancerous tumor can include a cancerous cell population. The one or more applied electric fields are effective to delay mitosis and cause mitotic synchronization within a proportion of the cancerous cell population. The method can include removing the one or more electric fields to allow mitosis to proceed within the cancerous cell population. The method can include administering a chemotherapeutic agent to the subject after the one or more electric fields have been removed.

In a second aspect, in addition to one or more of the preceding or following aspects, or in the alternative to some aspects, where applying the one or more electric fields to the cancerous tumor includes applying the one or more electric fields over a time period selected from a range of time periods from 1 minute to 24 hours.

In a third aspect, in addition to one or more of the preceding or following aspects, or in the alternative to some aspects, the method can include administering the chemotherapeutic agent to the subject when at least 5% of the cancerous cell population is synchronized in mitosis in response to the one or more electric fields.

In a fourth aspect, in addition to one or more of the preceding or following aspects, or in the alternative to some aspects, where the one or more electric fields are applied to the cancerous tumor at frequencies selected from a range of between 100 kHz to 300 kHz.

In a fifth aspect, in addition to one or more of the preceding or following aspects, or in the alternative to some aspects, where the one or more electric fields include an electric field strength selected from a range of electric field strengths from 3 V/cm to 5 V/cm.

In a sixth aspect, in addition to one or more of the preceding or following aspects, or in the alternative to some aspects, where the chemotherapeutic agent is administered to the subject in a therapeutically effective dose.

In a seventh aspect, in addition to one or more of the preceding or following aspects, or in the alternative to some aspects, where applying the one or more electric fields to the subject includes applying the one or more electric fields to an exterior of the subject at or near the site of the cancerous tumor.

In an eighth aspect, in addition to one or more of the preceding or following aspects, or in the alternative to some aspects, where applying the one or more electric fields to the cancerous tumor includes applying the one or more electric fields at least partially to an interior of the subject at or near the site of the cancerous tumor.

In a ninth aspect, in addition to one or more of the preceding or following aspects, or in the alternative to some aspects, where applying the one or more electric fields to the cancerous tumor includes applying the one or more electric fields at least partially to an exterior of the subject at or near the site of the cancerous tumor.

In a tenth aspect, in addition to one or more of the preceding or following aspects, or in the alternative to some aspects, where the medical device further includes one or more electrical leads in electrical communication with the electric field generating circuit.

In an eleventh aspect, a method for of treating a cancerous tumor is included. The method can include implanting one or more implantable electrodes inside a body of a subject with the cancerous tumor. The method can include placing one or more external electrodes on an outside surface of the body of the subject. The method can include generating an electric field between at least one pair of electrodes according to a predefined schedule, where the electric field having frequencies within a range of between 10 kHz to 1 MHz. The method can include removing the one or more electric fields; and administering a chemotherapeutic agent at or near a site of the cancerous tumor after the one or more electric fields have been removed.

In a twelfth aspect, in addition to one or more of the preceding or following aspects, or in the alternative to some aspects, where the one or more applied electric fields are effective to delay mitosis and cause mitotic synchronization within a proportion of the cancerous cell population.

In a thirteenth aspect, in addition to one or more of the preceding or following aspects, or in the alternative to some aspects, where removing the one or more electric fields allows mitosis to proceed within the cancerous cell population.

In a fourteenth aspect, a medical device for treating a cancerous tumor is included. The medical device can include an electric field generating circuit configured to generate one or more electric fields at or near a site of the cancerous tumor, where the cancerous tumor can include a cancerous cell population. The medical device can include control circuitry in communication with the electric field generating circuit, where the control circuitry can be configured to control delivery of the one or more electric fields from the electric field generating circuit at or near the site of the cancerous tumor. The control circuitry can cause the electric field generating circuit to generate one or more electric fields at frequencies selected from a range of between 10 kHz to 1 MHz at the site of a cancerous tumor located within a bodily tissue, where the one or more electric fields are effective to delay mitosis and cause mitotic synchronization within a proportion of the cancerous cell population.

In a fifteenth aspect, in addition to one or more of the preceding or following aspects, or in the alternative to some aspects, the medical device further can include one or more electrical leads in electrical communication with the electric field generating circuit.

In a sixteenth aspect, in addition to one or more of the preceding or following aspects, or in the alternative to some aspects, the medical device further can include one or more of: drug delivery catheters for delivery of one or more chemotherapeutic agents; optical leads can include one or more optical emitters for delivering photoactivating light energy; a biopsy apparatus for obtaining a biopsy sample from the cancerous tumor; and irrigation catheters for flushing waste products or bodily fluids.

In a seventeenth aspect, in addition to one or more of the preceding or following aspects, or in the alternative to some aspects, where the chemotherapeutic agent includes an antimitotic agent.

In an eighteenth aspect, in addition to one or more of the preceding or following aspects, or in the alternative to some aspects, where the chemotherapeutic agent includes at least one of vindesine, vincristine, vinblastine, paclitaxel, docetaxel, 2-methoxyestradiol, patupilone, trastuzumab emtansine, and derivatives thereof.

In a nineteenth aspect, in addition to one or more of the preceding or following aspects, or in the alternative to some aspects, where the chemotherapeutic agent includes an optically activated chemotherapeutic agent.

In a twentieth aspect, in addition to one or more of the preceding or following aspects, or in the alternative to some aspects, where the chemotherapeutic agent includes nanoparticles.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

Figure 1:
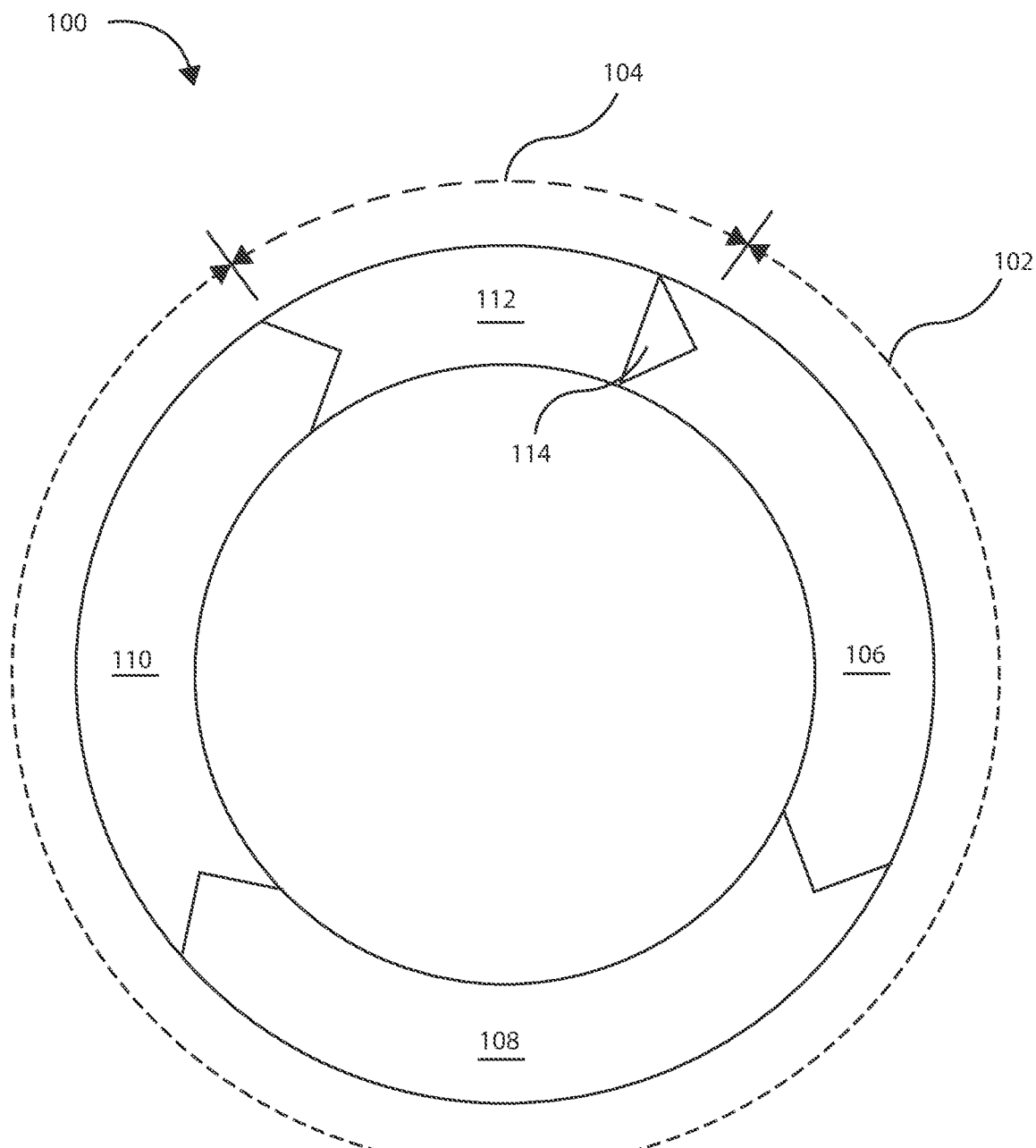
FIG. 1 is a schematic view of an exemplary cell cycle in accordance with various embodiments herein.

While embodiments are susceptible to various modifications and alternative forms, specifics thereof have been shown by way of example and drawings and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that alternating electric fields can disrupt mitosis within a cancerous tumor by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances an alternating electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules, can result in apoptosis (i.e., programmed cell death). It will further be appreciated that in some embodiments, alternating electric fields can disrupt mitosis by interfering with proteins involved in the formation of the contractile ring that is responsible for generating the constricting force when two daughter cells are separated. Various proteins involved in the formation of the contractile ring can include, but are not to be limited to F-actin, myosin-2, anillin, one or more septins, Rho, profilin, cofilin, and male germ cell Ras-related C3 botulinum toxin substrate GTPase activating proteins (MgcRacGAP).

It is also believed that alternating electric fields can synchronize mitosis within a cell population, including cancerous cells. It is believed that synchronizing a cancerous cell population can render the cancerous cell population to be highly susceptible to one or more chemotherapeutic agents in a shorter time period due to the chemotherapeutic agent being more effective in targeting the synchronous mitotically active cell population.

In addition, in some embodiments, optically activated chemotherapeutic agents may be administered in combination with electrical stimulation therapy. In some embodiments, nanoparticles may be administered in combination with electrical stimulation therapy.

Referring now to FIG. 1, a schematic view of an exemplary eukaryotic cell cycle 100 is shown in accordance with the embodiments herein. A eukaryotic cell cycle can be broken into two major phases, including interphase 102 and the M phase 104. Interphase includes three key phases, including the G1 phase 106 (i.e., the gap phase 1); the S phase 108 (i.e., the synthesis phase); and the G2 phase 110 (i.e., the gap phase 2). During the G1 phase 106, the cell prepares itself for doubling by beginning the process of duplicating all of its cellular contents, exclusive of the chromosomes. During the S phase 108, the cell synthesizes new DNA through the process of DNA replication to form two sister chromatids for each chromosome in the cell. During the G2 phase 110, the cell continues its growth and it synthesizes the proteins required by the cell for the M phase.

Figure 2:
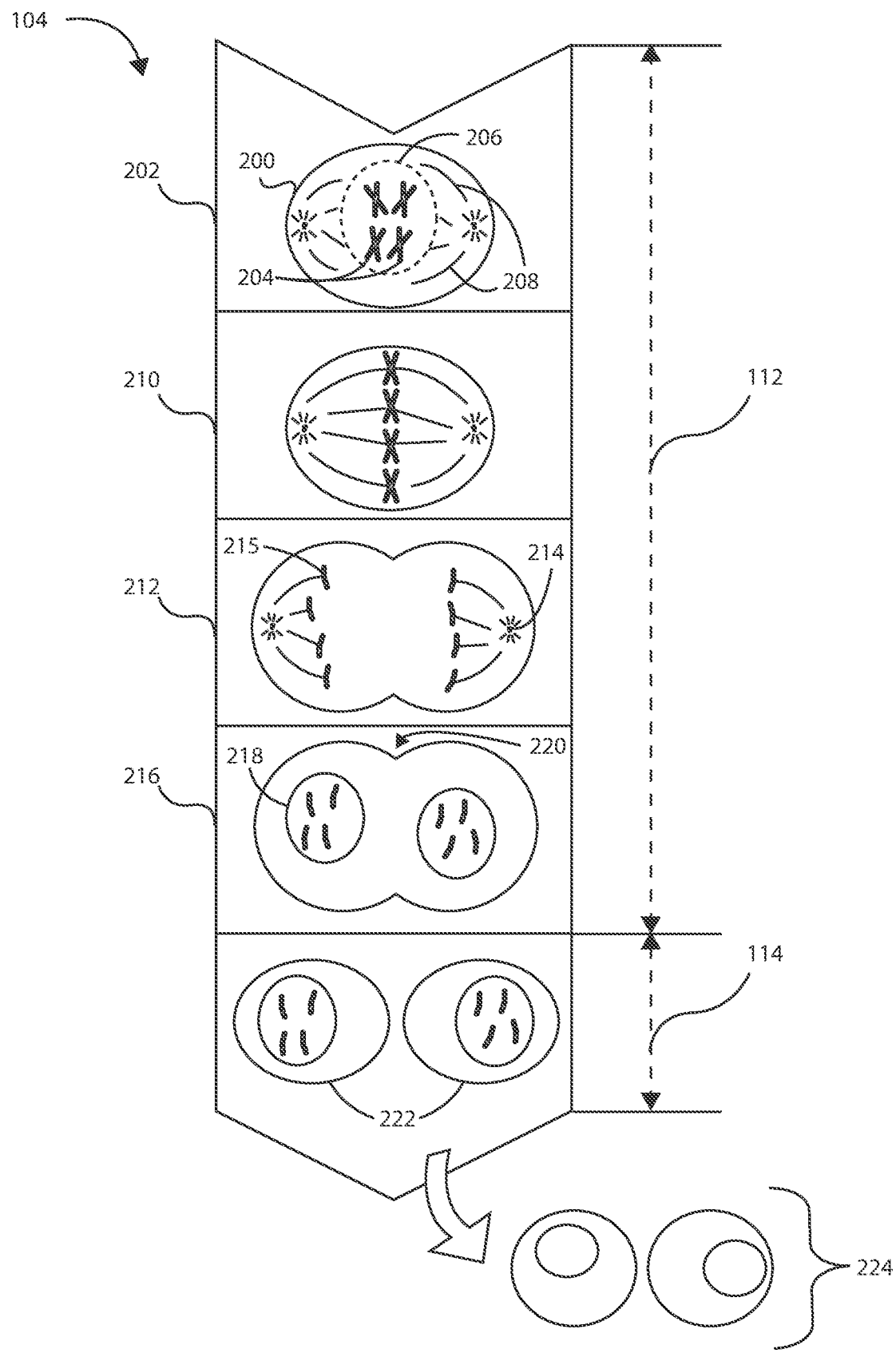
FIG. 2 is a schematic view of the M-phase in a healthy eukaryotic cell in accordance with various embodiments herein.

The M phase of the cell cycle 100 consists of two key phases: mitosis 112 and cytokinesis 114. Mitosis 112 is the process of nuclear division, and cytokinesis 114 is the process of cytoplasmic division. Referring now to FIG. 2, a schematic view of the M phase 104 in an exemplary eukaryotic cell cycle is shown in accordance with the embodiments herein. For healthy exemplary cell 200, mitosis begins at the process of prophase 202, where the chromosomes 204 begin to condense to form a pair of identical sister chromatids (sister chromatids 215 will be discussed below), the nuclear envelope 206 surrounding the nucleus disappears, and the spindle apparatus, including the spindle fibers 208, begin to form. Prophase 202 is followed by metaphase 210, where the chromosomes 204 line up on the equatorial plane of the dividing cell and become bound by the spindle fibers 208 at the kinetochores of each chromosome. The chromosomes 204 are then separated during anaphase 212 by the action of the spindle fibers 208 pulling each sister chromatid 215 towards each centrosome 214 and to opposite poles of the dividing cell. During telophase 216, a nuclear membrane 218 reforms around each set of chromosomes 204 at the opposite poles of the dividing cell, and a cleavage furrow 220 begins to form between the two halves of the dividing cell. The final step in the cell cycle is the step of cytokinesis 114, resulting in the formation of two genetically identical daughter cells 222 that can exit the cell cycle or reenter a subsequent cell cycle process 224.

Many cancerous cells are highly metabolically active and have high mitotic rates associated with cellular division. The methods and medical devices for treating a cancerous tumor described herein can target mitosis in the rapidly dividing cancer cells. Without being bound by any particular theory, application of a chemotherapeutic agent and/or applied antimitotic therapies, can alter the phases of mitosis within a cancerous cell in a number of ways.

Figure 3:
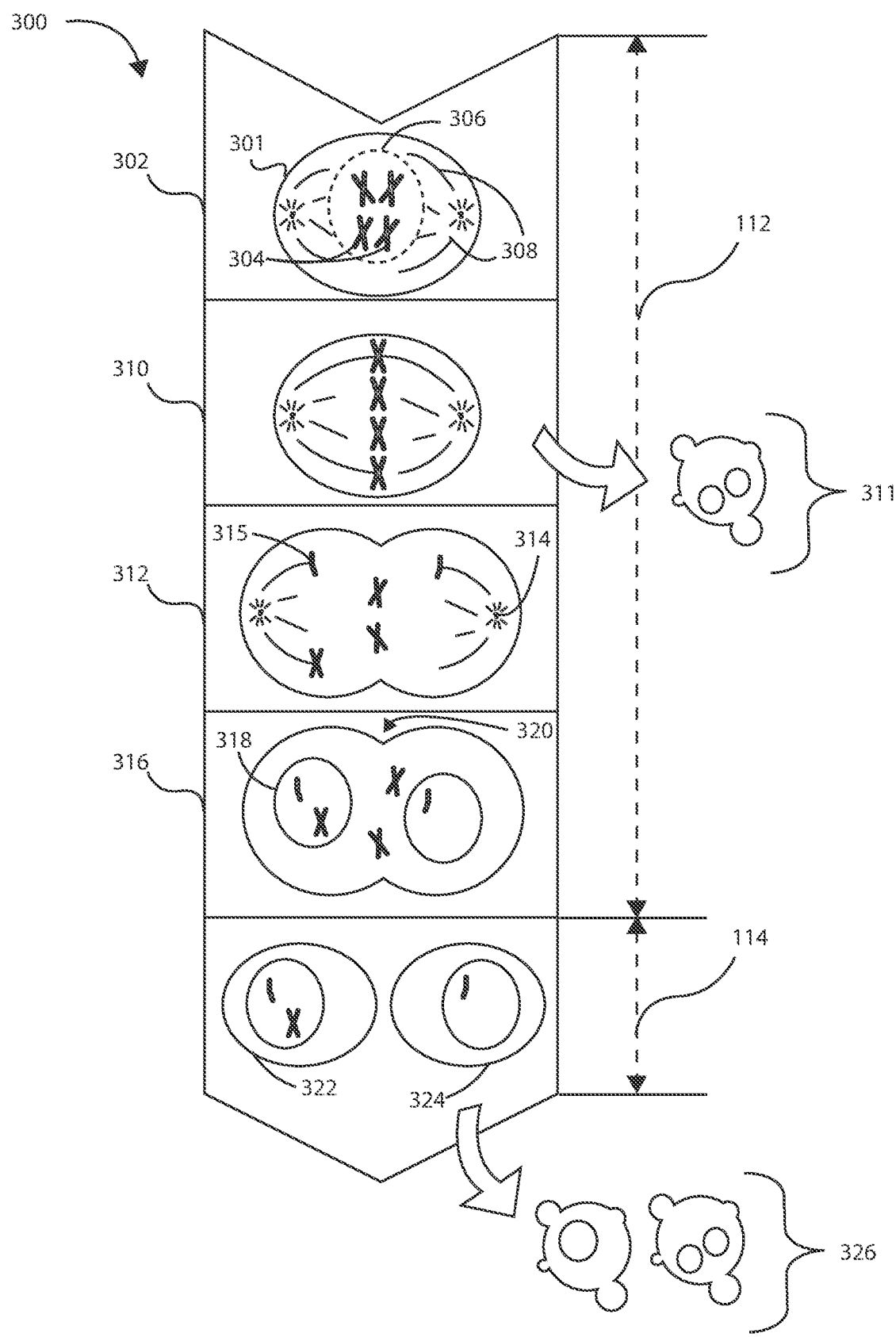
FIG. 3 is a schematic view of M-phase in a cancerous eukaryotic cell in accordance with various embodiments herein.

Referring now to FIG. 3, a schematic view of the M phase 300 in an exemplary cancerous cell 301 that has been disrupted by a chemotherapeutic agent and/or applied antimitotic therapy is shown in accordance with the embodiments herein. Mitosis within cancerous cell 301 begins similar to a healthy exemplary cell 200 as shown in FIG. 2. The process of mitosis within cancerous cell 301 begins in prophase 302, where the chromosomes 304 of the cancerous cell 301 begin to condense, the nuclear envelope 306 surrounding the nucleus disappears, and the spindle apparatus, including the spindle fibers 308, begin to form. An antimitotic agent and/or applied antimitotic therapy administered to cancerous cell 301 can destabilize spindle fiber 308 formation so that during metaphase 310, not all of the chromosomes become bound by the spindle fibers 308. In some embodiments, the chemotherapeutic agent is an antimitotic agent.

A consequence of destabilized spindle fibers can include mitotic arrest, or delay, in mitosis, which can lead to cell death (i.e., apoptosis) or mitotic slippage 311. A dividing cancerous cell can also proceed through mitosis through abnormal cellular division. If mitosis continues through abnormal cellular division and the chromosomes 304 cannot be separated evenly, then sister chromatids 315 and/or duplicated chromosomes 304 can be pulled towards the centrosomes 314 to opposite poles of the dividing cell and become unevenly distributed during anaphase 312. The cell can then proceed to telophase 316 where a nuclear membrane 318 can reform around each set of the chromosomes 304 at the opposite poles of the dividing cell, and a cleavage furrow 320 can form between the two halves of the cell. The final step in the cell cycle for the cancerous cell 301 is the step of cytokinesis 114, resulting in the formation of a first genetically distinct daughter cell 322 and a second genetically distinct daughter cell 324. In some embodiments, the genetically distinct daughter cells can die via apoptosis, reenter interphase of a subsequent cell cycle and die, or reenter mitosis 326.

Figure 4:
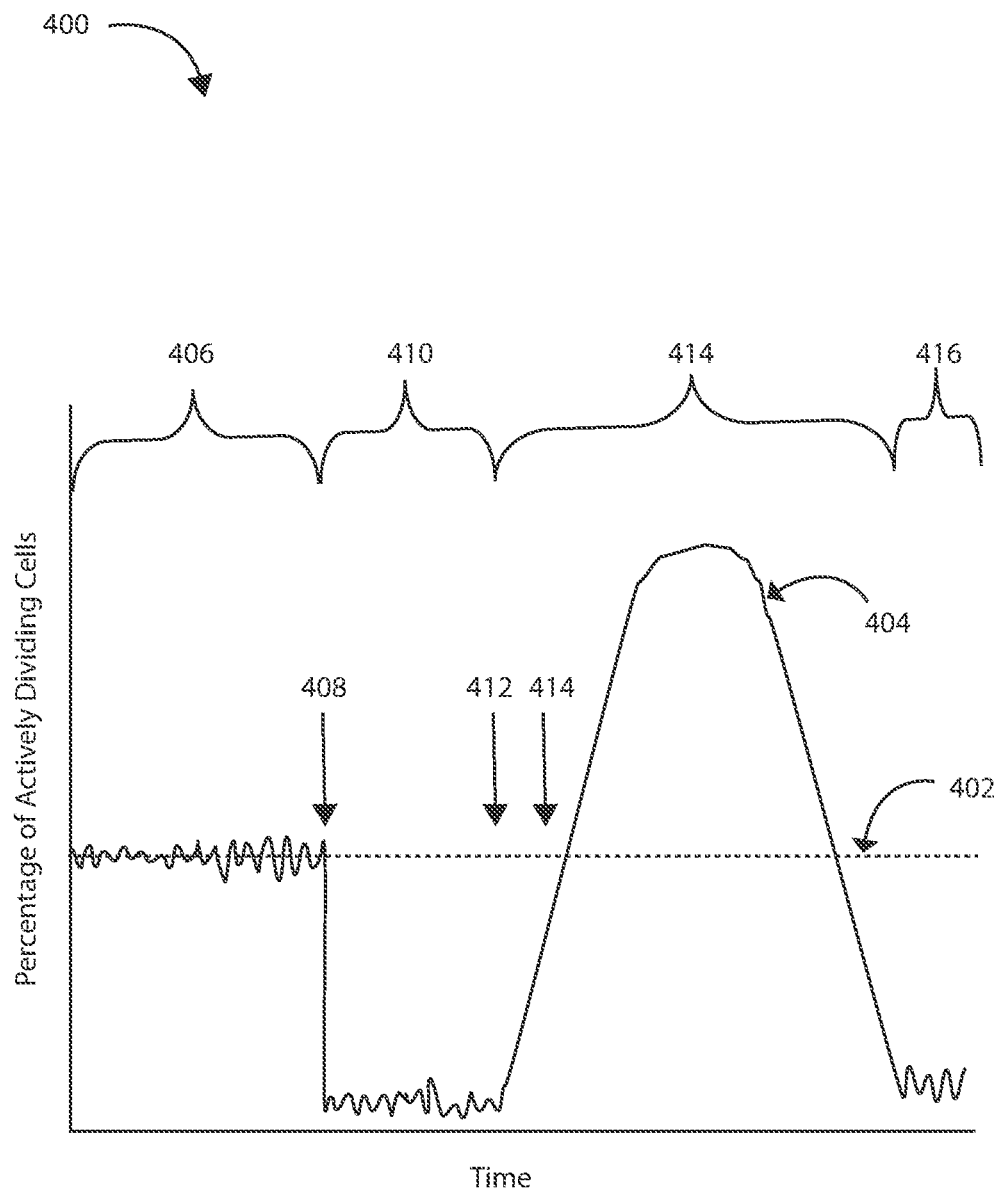
FIG. 4 is a schematic plot of the percent of actively dividing cells verses time in accordance with various embodiments herein.

A given cell population can include a baseline percentage of cells actively dividing at any given time. Referring now to FIG. 4, an exemplary graph 400 of the percentage of actively dividing cells versus time is shown in accordance with various embodiments herein. Plot 402 shows an average baseline percentage of actively dividing cells in a cancerous cell population of a cancerous tumor as a function of time. Plot 404 shows the percentage of actively dividing cells in an exemplary cancerous cell population of a cancerous tumor undergoing a method for treating a cancerous tumor. The cancerous cell population exhibits a baseline percentage of actively dividing cells during time 406. When an electric field is applied to the cancerous cell population 408, the percentage of cells actively dividing is halted and decreases in during time 410. Without being bound by any particular theory, it is believed that the applied electric field can be effective to delay mitosis within the given cell population and cause mitotic synchronization within at least a proportion of the given cell population. In some embodiments, the applied electric field can be effective to delay mitosis within a healthy cell population and cause mitotic synchronization within at least a proportion of the healthy cell population. In some embodiments, the applied electric field can be effective to delay mitosis within a cancerous cell population and cause mitotic synchronization within at least a proportion of the cancerous cell population.

After a predetermined amount of time, the applied electric field is removed 412. Release of the electric field allows the cells of the cancerous cell population to start actively dividing and continue proceeding through mitosis in synchrony. After the electric field is released 412, a chemotherapeutic agent can be administered to the cancerous cell population 414. The amount of time between releasing the electric field 412 and administering a chemotherapeutic agent 414 can vary as described below. It should be noted that in some embodiments, the chemotherapeutic agent can be administered to the cancerous cell population before the electric field is released.

Without being bound by any particular theory, when the cells within the cancerous cell population are in a state of mitotic synchronization, it is believed that administration of a chemotherapeutic agent can effectively reduce or destroy the number of viable cancerous cells present in the cancerous tumor. While release of the electric field allows the cells to proceed through mitosis, eventually the application of the electric field and/or the administration of the chemotherapeutic agent can reduce the number of actively dividing cells during time 414. Eventually, the combined treatment of the electric field and the chemotherapeutic agent can effectively decrease the number of viable cells in the cancerous tumor during time 416.

Figure 5:
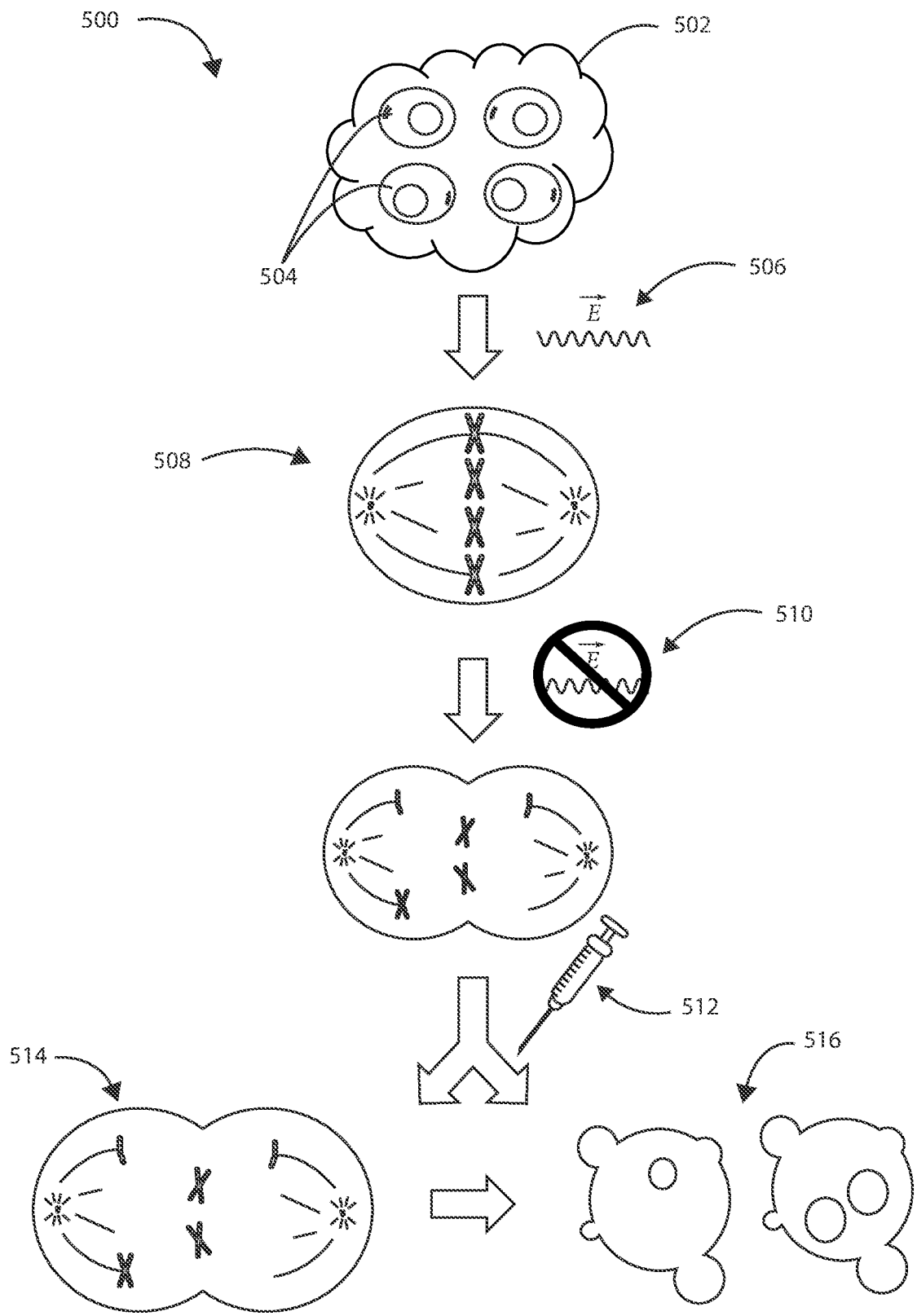
FIG. 5 is a schematic view of a method in accordance with various embodiments herein.

An exemplary method of treating a cancerous tumor can include application of one or more electric fields at or near the site of a cancerous tumor followed by administration of a chemotherapeutic agent. Referring now to FIG. 5, a schematic flow diagram of an exemplary method 500 for treating a cancerous tumor 502 located in a subject is shown in accordance with various embodiments herein. The method 500 can include applying one or more electric fields 506 at or near a site of the cancerous tumor 502. The cancerous tumor 502 can include a cancerous cell population 504. The one or more applied electric fields can be effective to delay mitosis in the cancerous cell population 504 and cause mitotic synchronization within at least a proportion of the cells within the cancerous cell population 508. The method 500 can include removing the one or more electric fields to allow mitosis to proceed within the cancerous cell population 510. The method 500 can include administering a chemotherapeutic agent at or near a site of the cancerous tumor after the one or more electric fields have been removed 512. In some embodiments, the chemotherapeutic agent can be delivered systemically through an intravenous port external to the body, or via an implantable device having an implantable conduit implanted within in the systemic vasculature, such as one implanted in the pectoral space. Administration of the chemotherapeutic agent can cause a disruption of mitosis within the cancerous cell population 514 and eventually lead to cell death within the cancerous cell population 516. In some embodiments, the method 500 can include inserting a transcutaneous access port at or near the site of the cancerous tumor.

Figure 6:
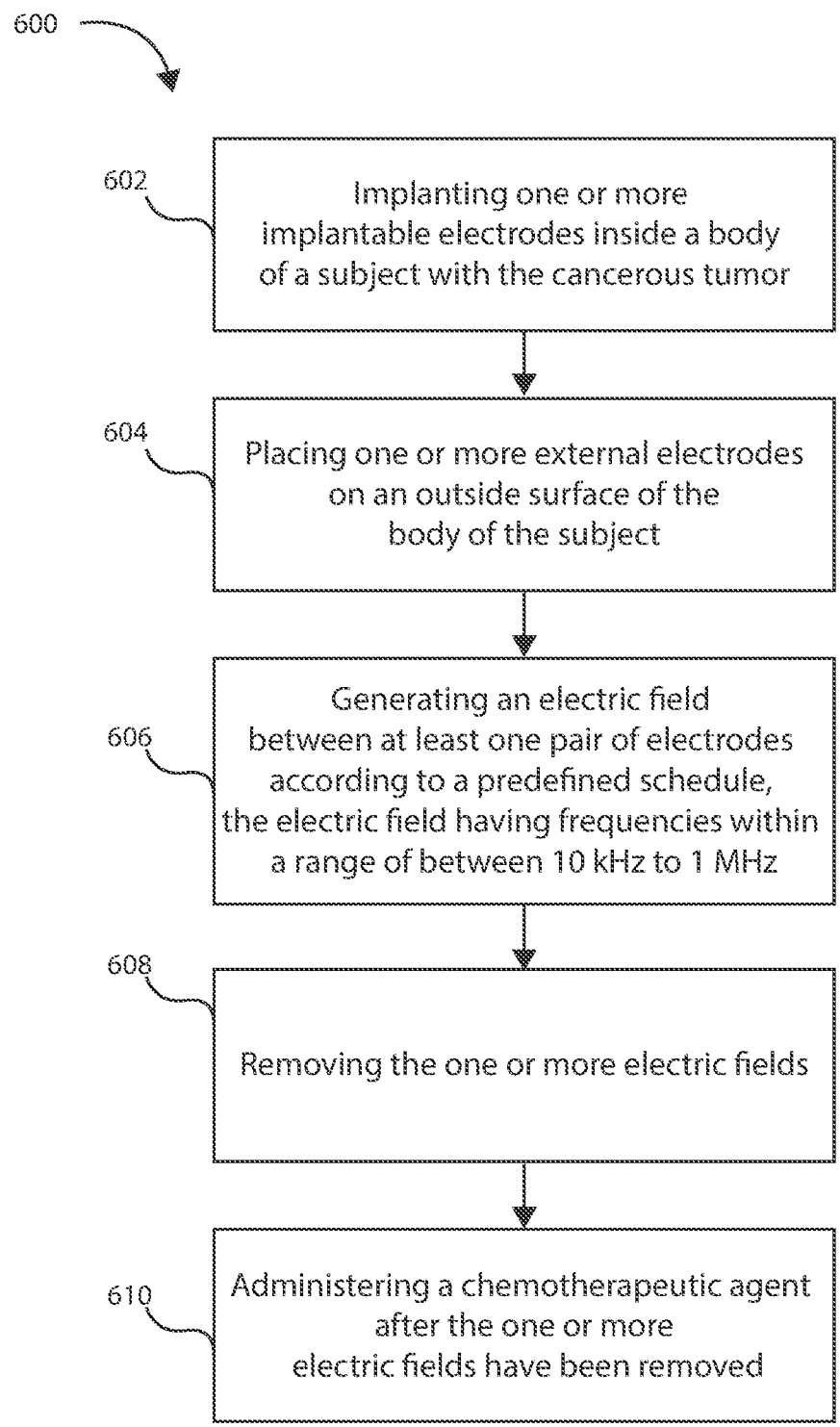
FIG. 6 is a schematic view of a method in accordance with various embodiments herein.

The methods herein can include the use of one or more implantable electrodes to treat a cancerous tumor. Referring now to FIG. 6, a method 600 for of treating a cancerous tumor is shown in accordance with various methods herein. The method 600 includes implanting one or more implantable electrodes inside a body of a subject with the cancerous tumor 602. The method 600 includes placing one or more external electrodes on an outside surface of the body of the subject 604. The method includes generating an electric field between at least one pair of electrodes according to a predefined schedule 606, the electric field having frequencies within a range of between 10 kHz to 1 MHz. The method 600 includes removing the one or more electric fields 608. The method includes administering a chemotherapeutic agent at or near a site of the cancerous tumor, or systemically, after the one or more electric fields have been removed 610. In some embodiments, the one or more applied electric fields of method 600 are effective to delay mitosis and cause mitotic synchronization within a proportion of the cancerous cell population. In some embodiments, removing the one or more electric fields in method 600 allows mitosis to proceed within the cancerous cell population.

Figure 7:
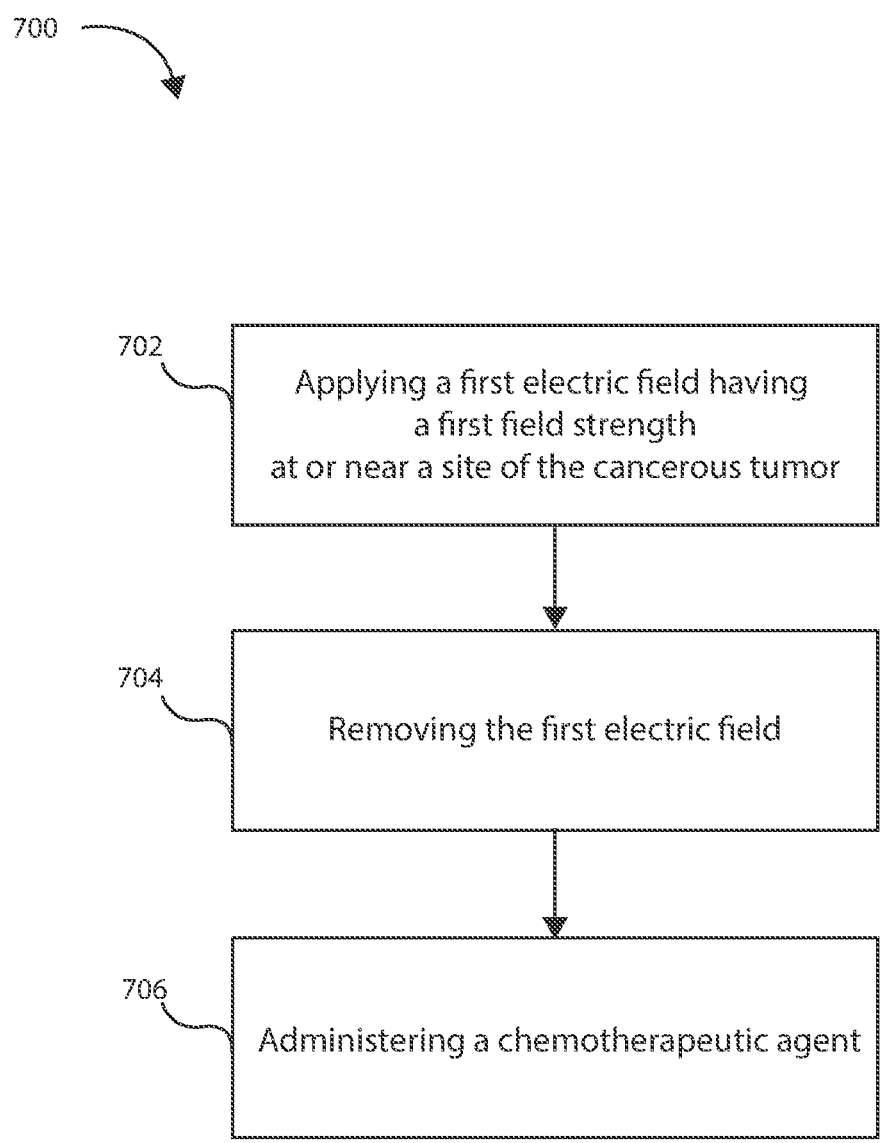
FIG. 7 is a schematic view of a method in accordance with various embodiments herein.

To optimize the delay of mitosis within the a given cell population and to cause mitotic synchronization within larger proportion of the given cell population, multiple applications of one or more electric fields can precede administration of chemotherapeutic agents, as will be discussed in reference to FIG. 7 and FIG. 8. Referring now to FIG. 7, a method 700 for treating a cancerous tumor located within a subject is shown with various embodiments herein. The method 700 can include applying a first electric field having a first field strength at or near a site of the cancerous tumor 702, where the cancerous tumor includes a cancerous cell population. The first electric field can be effective to delay mitosis and cause mitotic synchronization within a proportion of the cancerous cell population. The method 700 can include removing the first electric field to allow mitosis to proceed within the cancerous cell population 704. The method 700 can include administering a chemotherapeutic agent at or near a site of the cancerous tumor after the first electric field has been removed 706.

Figure 8:
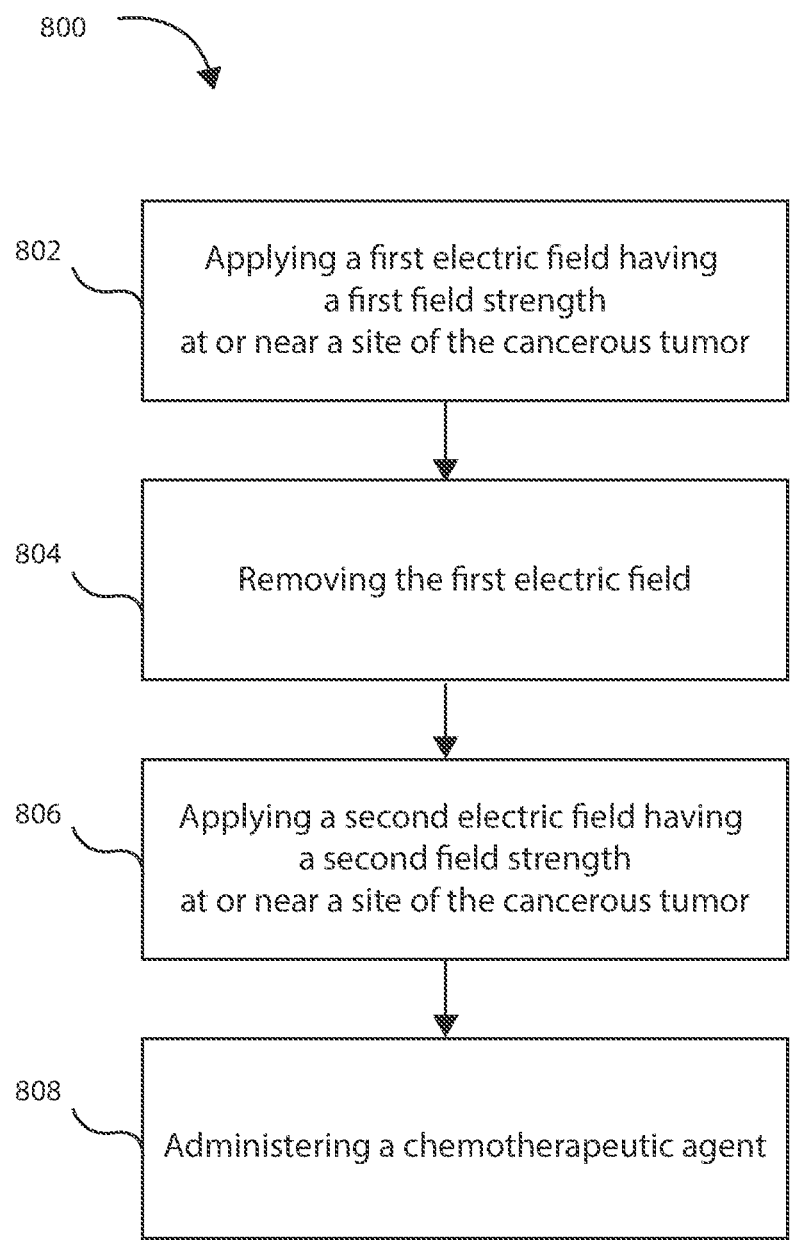
FIG. 8 is a schematic view of a method in accordance with various embodiments herein.

Referring now to FIG. 8, a method 800 for treating a cancerous tumor located within a subject is shown with various embodiments herein. The method 800 can include applying a first electric field having a first field strength at or near a site of the cancerous tumor 802, where the cancerous tumor includes a cancerous cell population. The first electric field can be effective to delay mitosis and cause mitotic synchronization within a proportion of the cancerous cell population. The method 800 can include removing the first electric field to allow mitosis to proceed within the cancerous cell population 804. The method 800 can include applying a second electric field having a second electric field strength at or near the site of the cancerous tumor after removing the first electric field and prior to administering the chemotherapeutic agent 806. The second electric field can be effective to delay mitosis and cause mitotic synchronization within a proportion of the cancerous cell population. The method 800 can include administering a chemotherapeutic agent at or near a site of the cancerous tumor after the first electric field has been removed 808. In some embodiments, the method 800 can include applying a third electric field having a third field strength at or near the site of a cancerous tumor. In some embodiments, the method 800 can include applying a fourth electric field having a fourth field strength at or near the site of a cancerous tumor. In other embodiments, the method 800 can include applying a fifth, sixth, seventh, eighth, ninth, or tenth electric field at or near the site of a cancerous tumor. In yet other embodiments, the method 800 can include applying greater than a tenth electric field at or near the site of a cancerous tumor.

The methods of applying a second or greater electric field having a second or greater electric field strength can include waiting a predetermined amount of time between applications of successive electric fields. By way of example, the method 800 can include waiting a predetermined amount of time after removing the first electric field prior to applying the second electric field. Similarly, in the application of a third electric field having a third electric field strength, application of the third electric field can be delayed by waiting a predetermined amount of time after removing the second electric field prior to applying the third electric field. However, in some embodiments, applying a second or greater electric field having a second or greater electric field strength can include applying the second or greater electric field immediately after application of the preceding electric field.

In some embodiments, the second electric field strength is less than the first electric field strength. In some embodiments, the second electric field strength is greater than the first electric field strength. In other embodiments, the second electric field strength is the same as the first electric field strength. In some embodiments, each successive application of an additional electric field having its unique electric field strength can include the additional electric field having an electric field strength that is less than, that is greater than, or that is the same as the preceding or successive electric fields.

Figure 9:
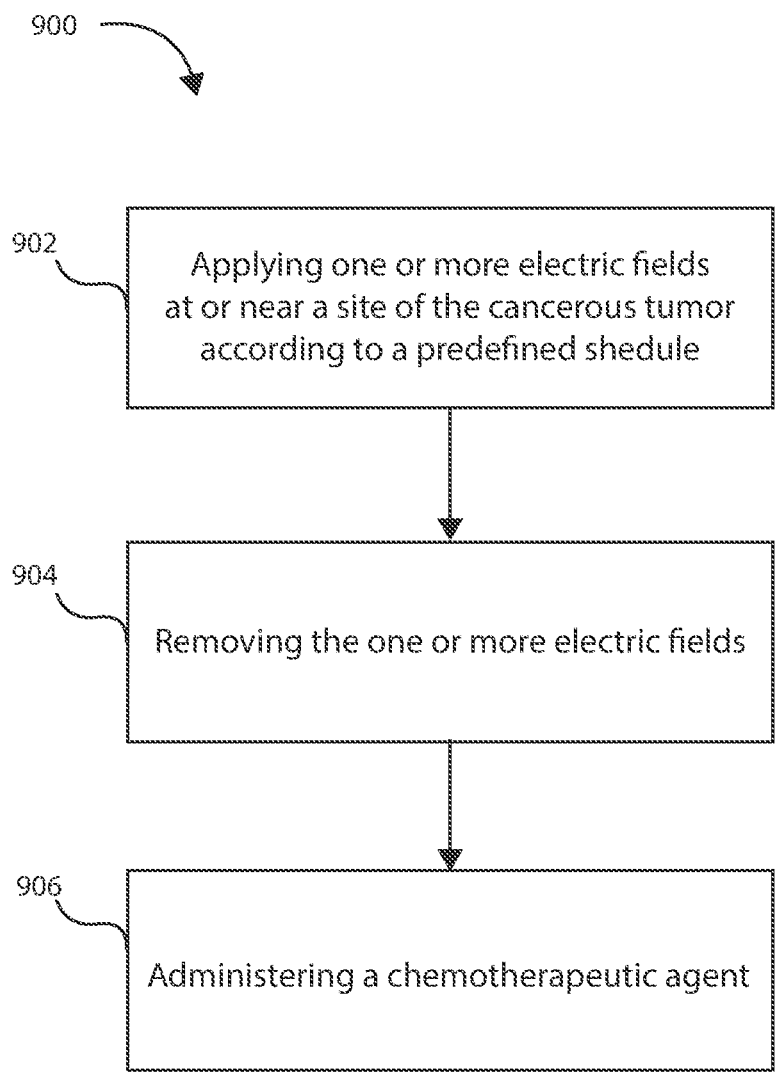
FIG. 9 is a schematic view of a method in accordance with various embodiments herein.

Application of the one or more electric fields in the methods herein can be temporally controlled. Referring now to FIG. 9, a method 900 for treating a cancerous tumor located within a subject is shown in accordance with the embodiments herein. The method 900 can include applying one or more electric fields at or near a site of the cancerous tumor according to a predefined schedule 902. The cancerous tumor include a cancerous cell population. The predefined schedule can cause the electric fields to vary in at least one of intensity and frequency over the course of a defined time period of at least six hours. The one or more applied electric fields of method 900 can be effective to delay mitosis and cause mitotic synchronization within a proportion of the cancerous cell population. In some embodiments, the method 900 can include removing the one or more electric fields to allow mitosis to proceed within the cancerous cell population 904. In other embodiments, the method 900 can include administering a chemotherapeutic agent at or near a site of the cancerous tumor after the one or more electric fields have been removed 906. In some embodiments, the method 900 can further include receiving a pause command from the subject, wherein the pause command causes cessation of applying the electric field.

Temporal control of the application of the one or more electric fields can include temporal variation of at least one of the intensity and frequency of the one or more electric fields on a predefined schedule. In some embodiments, temporal control of the application of the one or more electric fields can include temporal variation of at least one of the intensity and frequency, as compared to an initial intensity of frequency, of the one or more electric fields on a predefined schedule. In some embodiments, the predefined schedule includes one or more predetermined down periods wherein the one or more applied electric fields is decreased in intensity or frequency by at least 50% for at least 4 hours. In some embodiments, the predefined schedule includes one or more predetermined down periods wherein the one or more applied electric fields is decreased in intensity or frequency by at least 75% for at least 4 hours. In some embodiments, the predefined schedule includes one or more predetermined down periods wherein the one or more applied electric fields is decreased in intensity or frequency by greater than or equal to 25%, 30%, 35%, 40%, 45%, 50%, 55%, 60%, 65%, 70%, 75%, 80%, 85%, 90%, 95%, 98%, 99% or 100% or can be an amount falling in a range within any of the foregoing.

Figure 10:
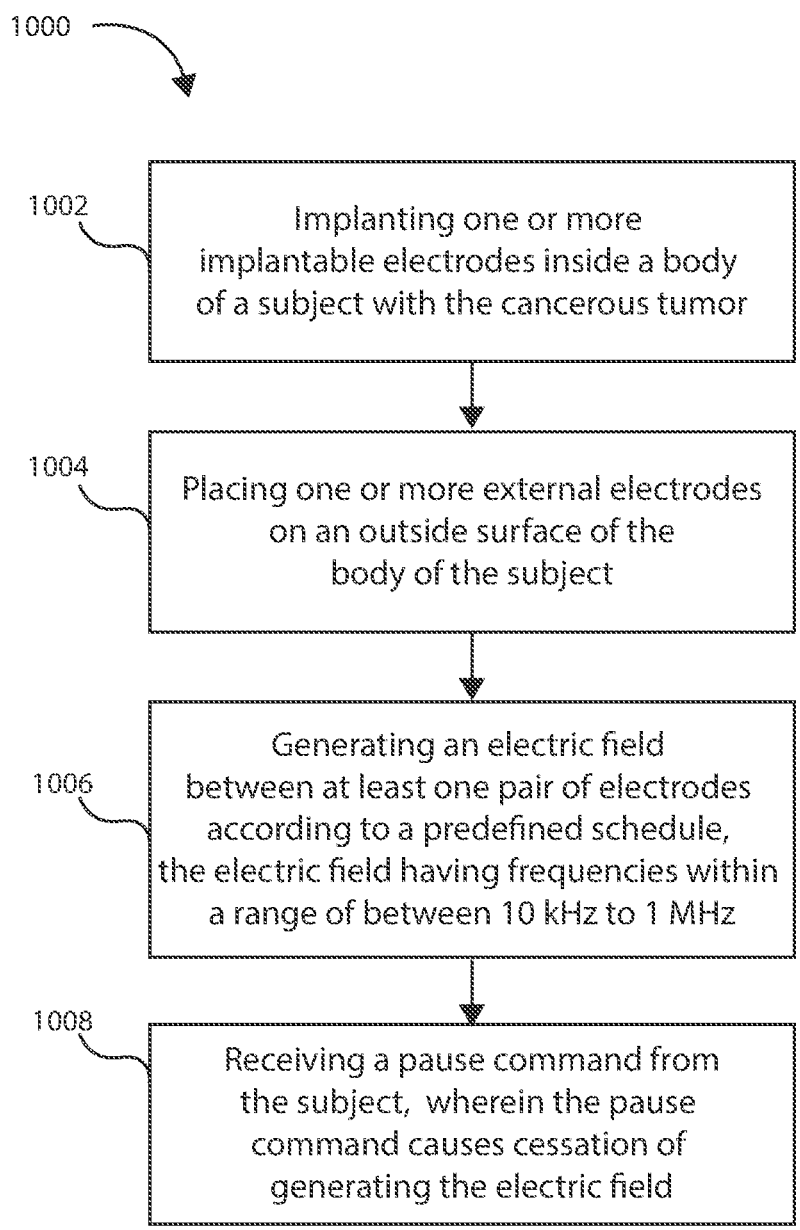
FIG. 10 is a schematic view of a method in accordance with various embodiments herein.

The various methods herein can include receiving a command from a subject and/or a care provider during the course of treating a cancerous tumor. Referring now to FIG. 10, a method 1000 for treating a cancerous tumor is shown in accordance with the embodiments herein. The method 1000 can include implanting one or more implantable electrodes inside a body of a subject with the cancerous tumor 1002. The method 1000 can include placing one or more external electrodes on an outside surface of the body of the subject 1004. The method 1000 can include generating an electric field between at least one pair of electrodes according to a predefined schedule 1006, the electric field having frequencies within a range of between 10 kHz to 1 MHz. The method 1000 can include receiving a pause command from the subject and/or a care provider, where the pause command causes cessation of generating the electric field 1008. In some embodiments, the method 1000 can include reinitiating generating the electric field between the at least one pair of electrodes according to the predefined schedule after a time period has elapsed after receiving the pause command from the subject and/or a care provider. In some embodiments, the method 1000 can include receiving an on command from the subject and/or a care provider, wherein the on command reestablishes generating the electric field. In other embodiments, the wherein the predefined schedule of method 1000 can include temporal variation of at least one of the intensity and frequency of the electric field, as described elsewhere herein. In some embodiments, the method 1000 can include administering a chemotherapeutic agent at or near a site of the cancerous tumor after during a time when the one or more electric fields have been paused.

Various commands can be received from the subject and/or a care provider during the course of treatment for a cancerous tumor with the various methods herein. In some embodiments, the command received from the subject and/or a care provider can include a pause command. A pause command can be received from a subject and/or a care provider to pause the application of the first electric field when the subject experiences one or more side effects including dizziness, nausea, fatigue, light headedness, headache, or localized pain. The pause command received from the subject and/or a care provider can include at least one of an off command, an off-for-a-set-time command, an off button depressed command, or an off-status reminder command. The off command can temporarily suspend generation of the electric field. The off-for-a-set-time command can temporarily suspend generation of the electric field for a predetermined period of time. By way of example, the off-for-a-set-time command can temporarily suspend generation of the electric field for at least 1 hour. In some embodiments, the off-for-a-set-time command can temporarily suspend generation of the electric field for at least 6 hours. In some embodiments, the off-for-a-set-time command can temporarily suspend generation of the electric field for at least 10 hours. In some embodiments, the off-for-a-set-time command can temporarily suspend generation of the electric field for greater than or equal to 1, 2, 3, 4, 5, 6, 7, 8, 9, 10, 11, or 12 hours, or can be an amount falling in a range within any of the foregoing.

In the various methods described herein, applying the one or more electric fields can include at least applying an electric field at various electric field strengths. By way of example, the one or more electric fields can be applied to the cancerous tumor at electric field strengths selected from a range of electric field strengths from 0.25 V/cm to 500 V/cm. In some embodiments, the one or more electric fields can be applied to the cancerous tumor at electric field strengths selected from a range of electric field strengths from 1 V/cm to 10 V/cm. In some embodiments, the one or more electric fields can be applied to the cancerous tumor at electric field strengths selected from a range of electric field strengths from 1 V/cm to 5 V/cm. In some embodiments, the one or more electric fields can be applied to the cancerous tumor at electric field strengths selected from a range of electric field strengths from 3 V/cm to 5 V/cm. In some embodiments, the field strength can be greater than or equal to 0.25 V/cm, 0.50 V/cm, 0.75 V/cm, 1.00 V/cm, 1.25 V/cm, 1.50 V/cm, 1.75 V/cm, 2.00 V/cm, 2.25 V/cm, 2.50 V/cm, 2.75 V/cm, 3.00 V/cm, 3.25 V/cm, 3.50 V/cm, 3.75 V/cm, 4.00 V/cm, 4.25 V/cm, 4.50 V/cm, 4.75 V/cm, 5.00 V/cm, 5.25 V/cm, 5.50 V/cm, 5.75 V/cm, 6.00 V/cm, 6.25 V/cm, 6.50 V/cm, 6.75 V/cm, 7.00 V/cm, 7.25 V/cm, 7.50 V/cm, 7.75 V/cm, 8.00 V/cm, 8.25 V/cm, 8.50 V/cm, 8.75 V/cm, 9.00 V/cm, 9.25 V/cm, 9.50 V/cm, 9.75 V/cm, 10 V/cm, 20 V/cm, 30 V/cm, 40 V/cm, 50 V/cm, 60 V/cm, 70 V/cm, 80 V/cm, 90 V/cm, 100 V/cm, 150 V/cm, 200 V/cm, 250 V/cm, 300 V/cm, 350 V/cm, 400 V/cm, 450 V/cm, or 500 V/cm, or can be an amount falling in a range within any of the foregoing.

In the various methods described herein, applying the one or more electric fields can include at least applying an electric field at various frequencies. The one or more electric fields can be applied to the cancerous tumor at frequencies selected from a range within 10 kilohertz (kHz) to 1 megahertz (MHz). In some embodiments, the one or more electric fields can be applied to the cancerous tumor at frequencies selected from a range within 100 kHz to 500 kHz. In some embodiments, the one or more electric fields can be applied to the cancerous tumor at frequencies selected from a range within 100 kHz to 300 kHz. In some embodiments, the frequency of the one or more applied electric fields can be greater than or equal to 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, or 1 MHz or can be an amount falling in a range within any of the foregoing.

In various embodiments herein, the electric field can be released (ceased) and then a chemotherapeutic agent can be administered. In various embodiments, the amount of time between releasing the electric field and administering the chemotherapeutic agent can be about 0, 5, 10, 15, 20, 25, 30, 40, 50, 60, 90, 120 or 180 minutes, of an amount falling within a range between any of the foregoing.

In the various methods described herein, applying the one or more electric fields can include at least applying an electric field for various predetermined time periods. The one or more electric fields can be applied at or near the site of the cancerous tumor over a predetermined time period selected from a range of predetermined time periods from 1 minute to 24 hours. In some embodiments, the one or more electric fields can be applied at or near the site of the cancerous tumor over a predetermined time period can be greater than or equal to 1, 10, 20, 30, 40, or 50 minutes, or 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, or 48 hours, or can be an amount falling in a range within any of the foregoing.

In the various methods described herein, administering a chemotherapeutic agent can include administering the chemotherapeutic agent when at least a certain percentage of the population is synchronized in mitosis. In some embodiments, administering the chemotherapeutic agent to the cancerous tumor includes administering the chemotherapeutic agent when at least 5% of the cancerous cell population is synchronized in mitosis in response to the one or more electric fields. In some embodiments, administering the chemotherapeutic agent to the cancerous tumor includes administering the chemotherapeutic agent when at least 25% of the cancerous cell population is synchronized in mitosis in response to the one or more electric fields. In some embodiments, administering the chemotherapeutic agent to the cancerous tumor includes administering the chemotherapeutic agent when at least 50% of the cancerous cell population is synchronized in mitosis in response to the one or more electric fields. In some embodiments, administering the chemotherapeutic agent to the cancerous tumor includes administering the chemotherapeutic agent when at least 75% of the cancerous cell population is synchronized in mitosis in response to the one or more electric fields. In some embodiments, the percentage of cells in a state of delayed mitosis and mitotic synchronization can be greater than or equal to 5%, 10%, 15%, 20%, 25%, 30%, 35%, 40%, 45%, 50%, 55%, 60%, 65%, 70%, 75%, 80%, 85%, 90%, or 95%, or can be an amount falling in a range within any of the foregoing.

In the various methods described herein, administering a chemotherapeutic agent can include administering the chemotherapeutic agent for various predetermined time periods. The chemotherapeutic agent can be administered at or near the site of the cancerous tumor over a predetermined time period selected from a range of predetermined time periods from less than 1 minute to 600 minutes. In some embodiments, the chemotherapeutic agent can be administered at or near the site of the cancerous tumor over a predetermined time period can be greater than or equal to 1 sec., 5 sec., 10 sec., 15 sec., 20 sec., 25 sec., 30 sec., 35 sec., 40 sec., 45 sec., 50 sec., 55 sec., or 60 sec., 5 min., 10 min., 15 min., 20 min., 25 min., 30 min., 35 min., 40 min., 45 min., 50 min., 55 min., 60 min, 120 min, 180 min, 240 min, 300 min, 360 min, 420 min, 480 min, 540 min, or 600 min, or can be an amount falling in a range within any of the foregoing. It will be appreciated that the chemotherapeutic agent can also be administered systemically at a site away from the cancerous tumor.

In some embodiments, the chemotherapeutic agent is administered to a subject within a 12-hour time period following removal of the electric field. In some embodiments, the chemotherapeutic agent is administered to a subject within a 6-hour time period following removal of the electric field. In some embodiments, the chemotherapeutic agent is administered to a subject within a 3-hour time period following removal of the electric field. In some embodiments, the chemotherapeutic agent is administered to the subject within a 1-hour time period following removal of the electric field. Administration of chemotherapeutic agents will be discussed in more detail below.

In the various methods described herein, applying the one or more electric fields at or near the site of the cancerous tumor can include applying the one or more electric fields to the exterior or interior of the subject. In some embodiments, applying the one or more electric fields to the cancerous tumor can include applying the one or more electric fields entirely to the exterior of the subject at or near the site of the cancerous tumor. In some embodiments, applying the one or more electric fields to the cancerous tumor can include applying the one or more electric fields entirely to the interior of the subject at or near the site of the cancerous tumor. In some embodiments, applying the one or more electric fields to the cancerous tumor can include applying the one or more electric fields at least partially to the exterior of the subject at or near the site of the cancerous tumor. In some embodiments, applying the one or more electric fields to the cancerous tumor can include applying the one or more electric fields at least partially to the interior of the subject at or near the site of the cancerous tumor. In other embodiments, applying the one or more electric fields to the cancerous tumor can include applying the one or more electric fields partially to the interior and partially to the exterior of the subject at or near the site of the cancerous tumor. It will be appreciated that applying an electric field to the exterior of a subject can result in propagation of the electric field into the body of the subject.

Figure 11:
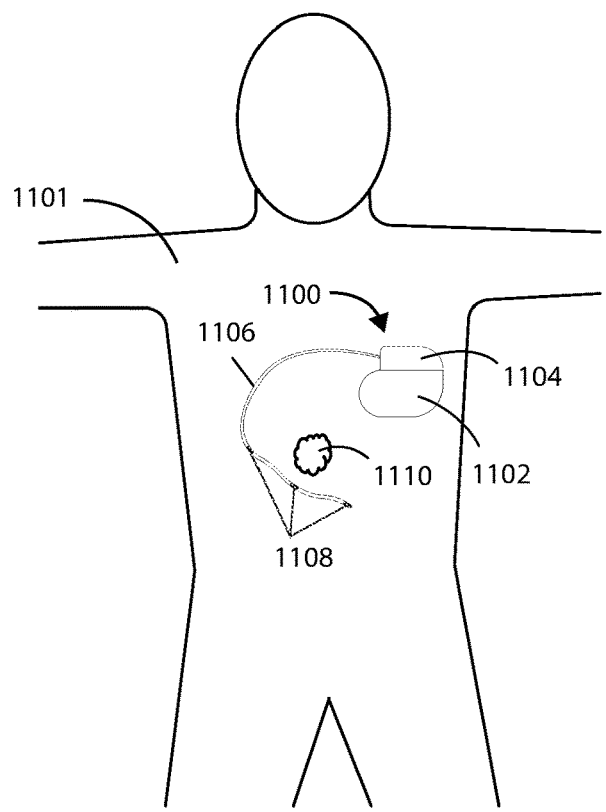
FIG. 11 is a schematic view a medical device in accordance with various embodiments herein.
Figure 12:
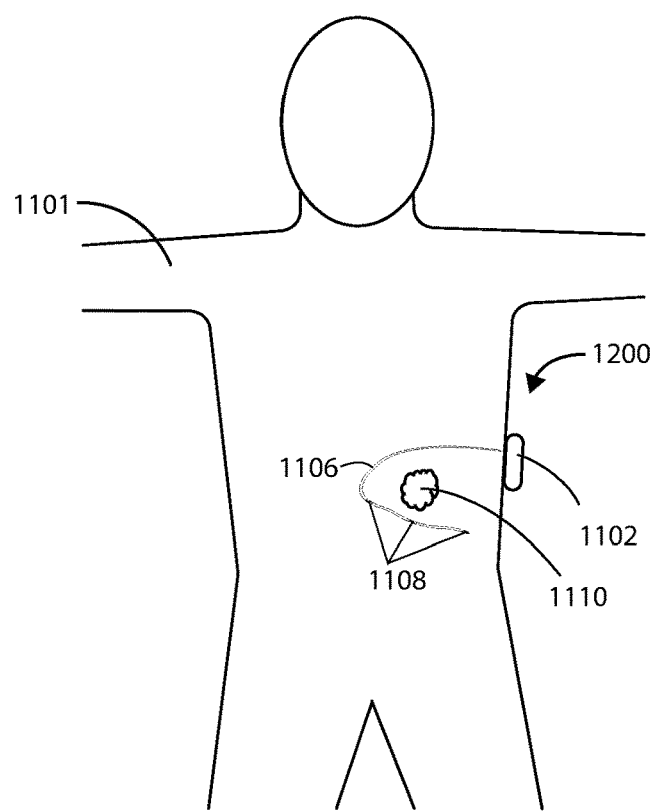
FIG. 12 is a schematic view a medical device in accordance with various embodiments herein.

The various methods herein can be delivered to a subject with a cancerous tumor using a variety of medical devices. Referring now to FIG. 11 and FIG. 12, schematic diagrams of a subject 1101 with a cancerous tumor 1110 are shown in accordance to the embodiments herein. In FIG. 11, the subject 1101 has a medical device 1100 implanted entirely within the body of the subject 1101 at or near the site of a cancerous tumor located within a bodily tissue. Various implant sites can be used including areas such as in the limbs, the upper torso, the abdominal area, the head, and the like. In FIG. 12, the subject 1101 has a medical device 1200 at least partially implanted within body of the subject 1101 at or near the site of a cancerous tumor located within a bodily tissue. In some embodiments, the medical device can be entirely external to the subject. In some embodiments, the medical device can be partially external to the subject. In some embodiments, the medical device can be partially implanted and partially external to the body of a subject. In other embodiments, a partially implanted medical device can include a transcutaneous connection between components disposed internal to the body and external to the body. A partially implanted medical device can wirelessly communicate with a partially external portion of a medical device over a wireless connection.

In some embodiments, a portion of the medical device can be entirely implanted and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include the many of the same components as and can be configured to perform many of the same functions as a pulse generator. In embodiments where a portion of a medical device is entirely implanted, and a portion of the medical device is entirely external, the portion of the medical device that is entirely external can communicate wirelessly with the portion of the medical device that is entirely internal. However, in other embodiments a wired connection can be used.

The medical device 1100 can include a housing 1102 and a header 1104 coupled to the housing 1102, and medical device 1200 can include a housing 1102. Various materials can be used. However, in some embodiments, the housing 1102 can be formed of a material such as a metal, ceramic, polymer, composite, or the like. In some embodiments, the housing 1102, or one or more portions thereof, can be formed of titanium. The header 1104 can be formed of various materials, but in some embodiments the header 1104 can be formed of a translucent polymer such as an epoxy material. In some embodiments the header 1104 can be hollow. In other embodiments the header 1104 can be filled with components and/or structural materials such as epoxy or another material such that it is non-hollow.

In some embodiments where a portion of the medical device 1100 or 1200 is partially external, the header 1104 and housing 1102 can be surrounded by a protective casing made of durable polymeric material. In other embodiments, where a portion of the medical device 1100 or 1200 is partially external, the header 1104 and housing 1102 can be surrounded by a protective casing made of a combination of polymeric material, metallic material, and/or glass material.

The header 1104 can be coupled to one or more leads 1106. The header 1104 can serve to provide fixation of the proximal end of one or more leads 1106 and electrically couple the one or more leads 1106 to one or more components within the housing 1102. The one or more leads 1106 can include one or more electrodes 1108 disposed along the length of the electrical leads 1106. In some embodiments, electrodes 1108 can include electric field generating electrodes and in other embodiments electrodes 1108 can include electric field sensing electrodes. In some embodiments, leads 1106 can include both electric field generating and electric field sensing electrodes. In other embodiments, leads 1106 can include any number of electrodes that are both electric field sensing and electric field generating. It will be appreciated that while many embodiments of medical devices herein are designed to function with leads, leadless medical devices that generate electrical fields are also contemplated herein. In some embodiments, the electrodes 1108 can be tip electrodes on the most distal end of the leads 1106.

Figure 13:
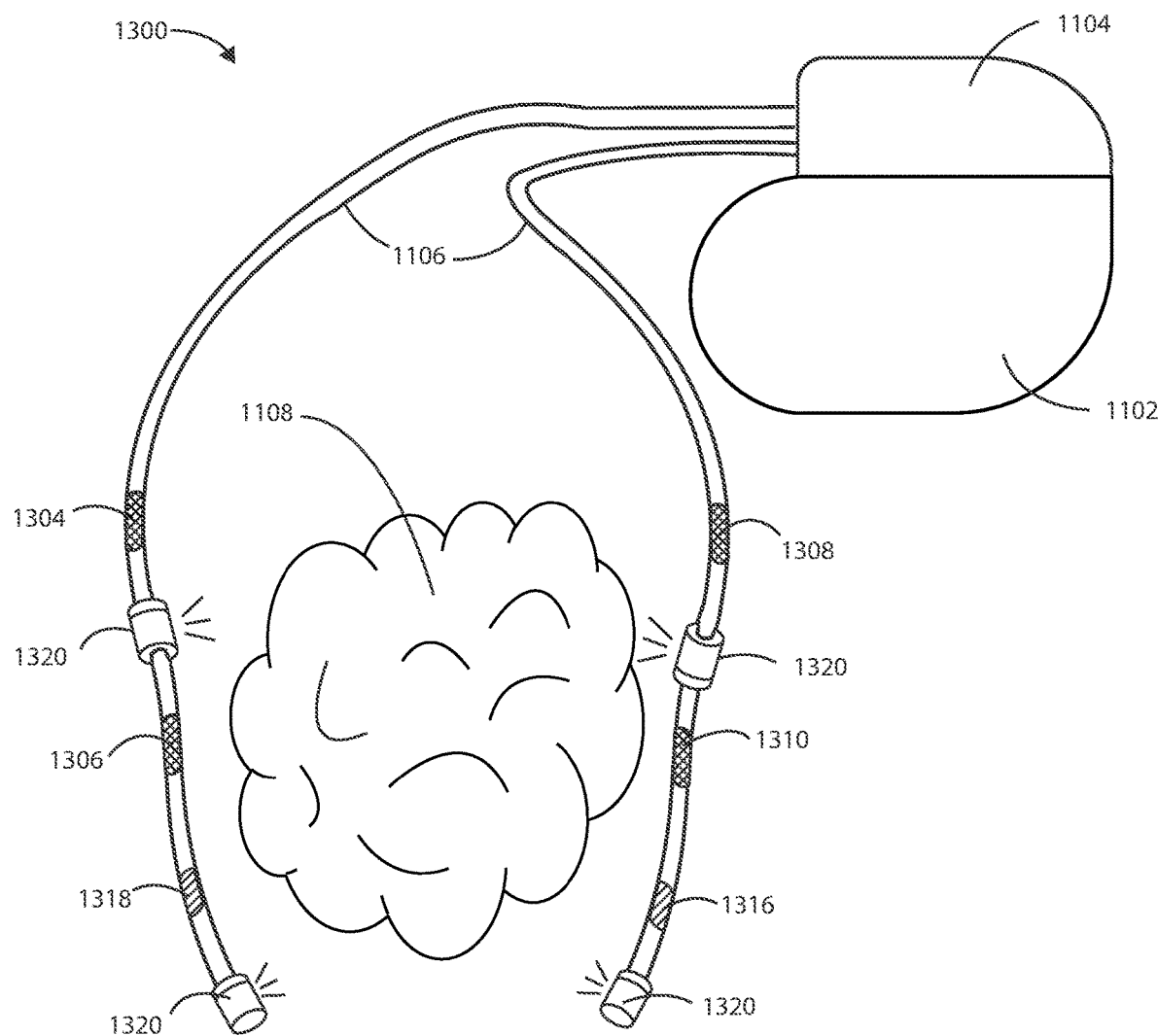
FIG. 13 is a schematic view a medical device in accordance with various embodiments herein.

Referring now to FIG. 13, a schematic diagram of a medical device 1300 is shown in accordance with the embodiments herein. Medical device 1300 can include housing 1102 and header 1104, and one or more leads 1106. Leads 1106 can include one or more electrodes such as electrodes 1304, 1306, 1308, or 1310, disposed along the length of the leads 1106. In some embodiments, electrodes 1304, 1306, 1308, or 1310 can include electric field generating electrodes and in other embodiments electrodes 1304, 1306, 1308, or 1310 can include electric field sensing electrodes. In some embodiments, leads 1106 can include both electric field generating and electric field sensing electrodes.

The proximal ends of leads 1106 are disposed within the header 1104. The distal ends of electrical leads 1106 can surround a cancerous tumor 1110 such that the electrodes 1304, 1306, 1308, or 1310 are brought into proximity of the cancerous tumor 1110. In some embodiments, the leads 1106 can be positioned within the vasculature such that electrodes 1304, 1306, 1308, or 1310 are adjacent to or positioned within the cancerous tumor 1110. However, it will be appreciated that leads 1106 can be disposed in various places within or around the cancerous tumor 1110. In some embodiments, the leads 1106 can pass directly through the cancerous tumor 1110.

In some embodiments, the leads 1106 can include one or more tracking markers 1316 or 1318 along the length of the lead for use in determining the precise location of the electrodes relative to the tumor. In some embodiments, the one or more tracking markers can be disposed directly distal or directly proximal to the one or more electrodes disposed on the lead. In some embodiments, the tracking markers can be formed from a magnetic material. In some embodiments, the tracking markers can be formed from a radiographic material. In some embodiments, the tracking markers can be formed from a fluorographic material.

In some embodiments, the leads 1106 can include one or more optical emitters 1320 for delivering optical energy at the site of the cancerous tumor. The optical emitters can be positioned along the length of leads 1106 or at the most distal tip of leads 1106. In some embodiments herein, the chemotherapeutic agent can include an optically activated chemotherapeutic agent, which will be discussed in more detail below. In some embodiments, the leads 1106 can include one or more optical fibers to deliver optical energy to the site of the cancerous tumor. The optical emitters can include, but are not to be limited to, light emitting diodes (LEDs) or laser diodes. In some embodiments, the leads 1106 can include one or more optical fibers to delivery optical energy to the site of the cancerous tumor. The optical emitters suitable for activating the optically activated chemotherapeutic agents used herein can include those with a maximum emission wavelength that can be greater than or equal to 350 nm, 400 nm, 450 nm, 500 nm, 550 nm, 600 nm, 650 nm, 700 nm, 750 nm, 800 nm, or 850 nm, or can be an amount falling in a range within any of the foregoing. It will be appreciated that optical emitters suitable for use herein may include those including an emission maximum ±10 nm on either side of the emission maximum. It will be appreciated that optical emitters suitable for use herein may include those including an emission maximum ±20 nm on either side of the emission maximum.

It will be appreciated that a plurality of electric field vectors can be generated between various combinations of electrodes 1304, 1306, 1308, or 1310 disposed along leads 1106 to create an electric field. For example, one or more electric field vectors can be generated between electrodes 1304 and 1308. Similarly, one or more electric field vectors can be generated between electrodes 1304 and 1310. It will also be appreciated that one or more electric field vectors can be generated between any combination of electrodes 1304, 1306, 1308, or 1310. In some embodiments, one or more electric field vectors can be generated between any combination of electrodes 1304, 1306, 1308, or 1310 and the housing 1102 of medical device. It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

Figure 14:
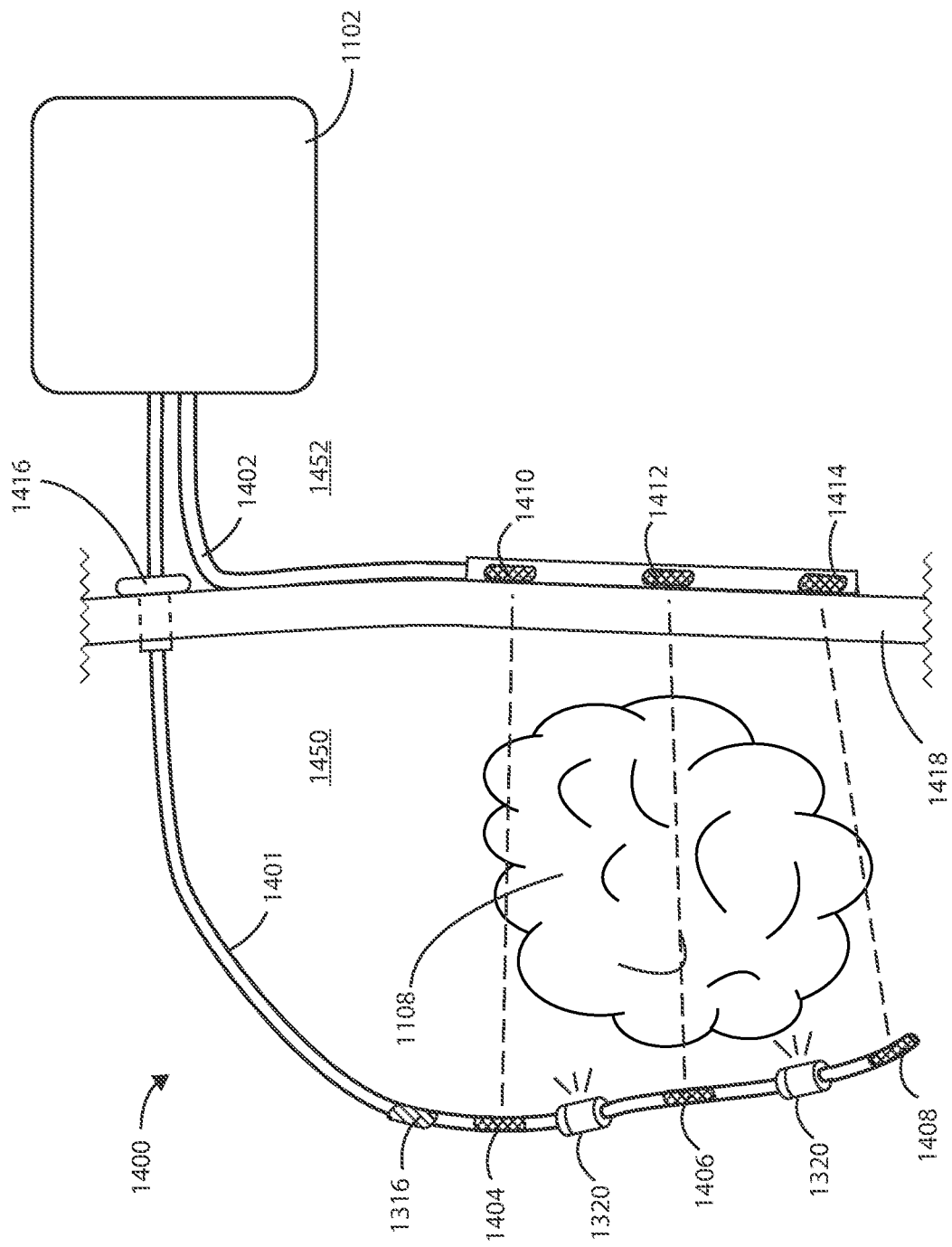
FIG. 14 is a schematic view a medical device in accordance with various embodiments herein.

Referring now to FIG. 14, a schematic diagram of a medical device 1400 is shown in accordance with the embodiments herein. Medical device 1400 can include an internal portion at the internal side 1450 of the subject's body and an external portion at the external side 1452 of the subject's body. The internal portion of medical device 1400 can include internal electric lead 1401 and the external portion can include the housing 1102 and the external electric lead 1402. The medical device 1400 can also include a transcutaneous access port 1416 spanning the exterior surface 1418 of the subjects body at or near the site of the cancerous tumor suitable to receive on or more leads of catheters. By way of example, transcutaneous access port 1416 can be configured to receive at least one of the internal electric lead 1401; a drug delivery catheter for delivery of one or more chemotherapeutic agents; an optical lead including one or more optical emitters for delivering optical energy; a biopsy apparatus for obtaining a biopsy sample from the cancerous tumor; or an irrigation catheter for flushing the site of the cancerous tumor of waste products or bodily fluids.

Internal electric lead 1401 can include one or more electrodes such as electrodes 1404, 1406, or 1408 disposed along the length of internal electric lead 1106. External electric lead 1402 can include electrodes 1410, 1412, or 1414 disposed along the length of the external electric lead 1402. In some embodiments, electrodes 1404, 1406, 1408, 1410, 1412, or 1414 can include electric field generating electrodes and in other embodiments electrodes 1404, 1406, 1408, 1410, 1412, or 1414 can include electric field sensing electrodes. In some embodiments, internal electric leads 1401 or external electric leads 1402 can include both electric field generating and electric field sensing electrodes.

The proximal ends of internal electric lead 1401 or external electric lead 1402 are disposed within the housing 1102. The distal ends of internal electric lead 1401 can surround a cancerous tumor 1110 such that the electrodes 1404, 1406, of 1408 are brought into proximity of the cancerous tumor 1110. External electric lead 1402 can be place on the exterior of the subject's body near the site of the cancerous tumor such that the electrodes 1410, 1412, and 1414 are in electrical communication with electrodes 1404, 1406, and 1408 on internal electric lead 1106. In some embodiments, the internal electric lead 1401 can be positioned within the vasculature such that electrodes 1404, 1406, or 1408 are adjacent to or positioned within the cancerous tumor 1110. However, it will be appreciated that internal electric lead 1401 can be disposed in various places within or around the cancerous tumor 1110. In some embodiments, the internal electric lead 1401 can pass directly through the cancerous tumor 1110.

In some embodiments, the internal electric lead 1401 can include one or more tracking markers 1316 along the length of the internal electric lead 1401 for use in determining the precise location of the electrodes relative to the tumor. In some embodiments, the one or more tracking markers can be disposed directly distal or directly proximal to the one or more electrodes disposed on the internal electric lead 1401. In some embodiments, the tracking markers can be formed from a magnetic material. In some embodiments, the tracking markers can be formed from a radiographic material. In some embodiments, the tracking markers can be formed from a fluorographic material.

It will be appreciated that a plurality of electric field vectors can be generated between various combinations of electrodes 1404, 1406, 1408, 1410, 1412, or 1414 disposed along internal electric lead 1401 and external electric lead 1402 to create an electric field. For example, one or more electric field vectors can be generated between electrodes 1404 and 1410. Similarly, one or more electric field vectors can be generated between electrodes 1406 and 1412. It will also be appreciated that one or more electric field vectors can be generated between any combination of electrodes 1404, 1406, 1408, 1410, 1412, or 1414. In some embodiments, one or more electric field vectors can be generated between any combination of electrodes 1404, 1406, 1408, 1410, 1412, or 1414 and the housing 1102 of medical device 1400. It will be appreciated that one or more unipolar or multipolar leads can be used in accordance with the embodiments herein. In some embodiments, a combination of unipolar and multipolar leads can be used. In other embodiments, a circular lead, clamp lead, cuff lead, paddle lead, or patch lead can be used.

Figure 15:
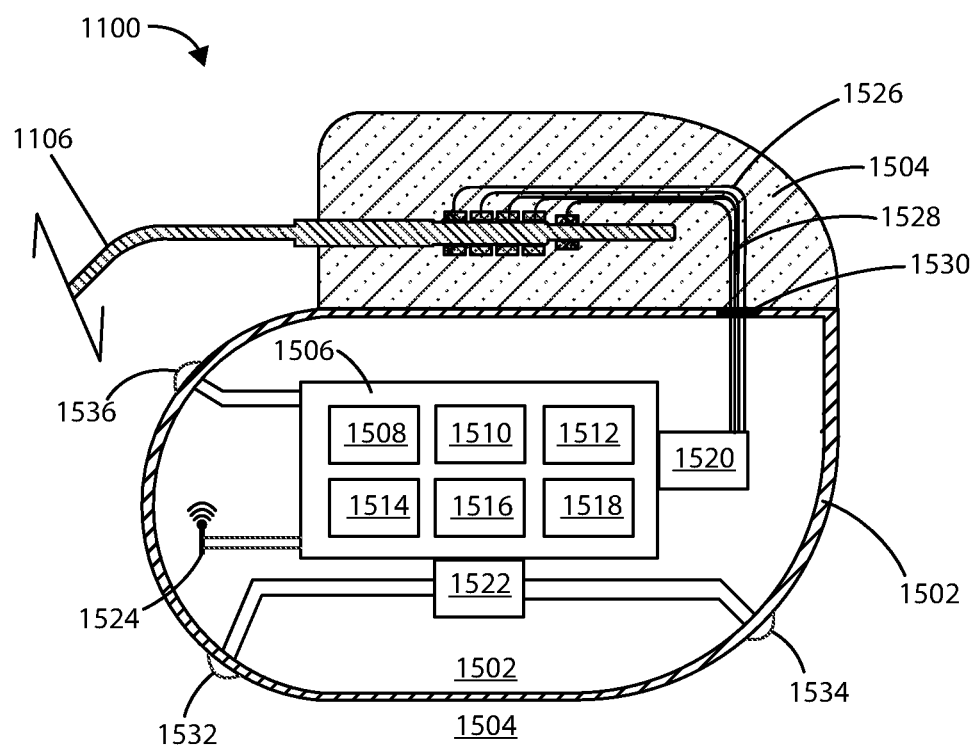
FIG. 15 is a schematic cross-sectional view of medical device in accordance with various embodiments herein.

Referring now to FIG. 15, a schematic cross-sectional view of exemplary medical device 1100 of FIG. 11 is shown in accordance with various embodiments herein. It will be appreciated the features of medical device 1100 can be included in any of the medical devices described herein. Housing 1102 can define an interior volume 1502 that can be hollow and that in some embodiments is hermetically sealed off from the area 1504 outside of medical device 1100. In other embodiments the housing 1102 can be filled with components and/or structural materials such that it is non-hollow. The medical device 1100 can include control circuitry 1506, which can include various components 1508, 1510, 1512, 1514, 1516, and 1518 disposed within housing 1102. In some embodiments, these components can be integrated and in other embodiments these components can be separate. In yet other embodiments, there can be a combination of both integrated and separate components. The medical device 1100 can also include an antenna 1524, to allow for unidirectional or bidirectional wireless data communication. In some embodiments, the components of medical device 1100 can include an inductive energy receiver coil (not shown) communicatively coupled or attached thereto to facilitate transcutaneous recharging of the medical device via recharging circuitry.

The various components 1508, 1510, 1512, 1514, 1516, and 1518 of control circuitry 1506 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 1506 can be in communication with an electric field generating circuit 1520 that can be configured to generate electric current to create one or more fields. The electric field generating circuit 1520 can be integrated with the control circuitry 1506 or can be a separate component from control circuitry 1506. Control circuitry 1506 can be configured to control delivery of electric current from the electric field generating circuit 1520. In some embodiments, the electric field generating circuit 1520 can be present in a portion of the medical device that is external to the body.

In some embodiments, the control circuitry 1506 can be configured to direct the electric field generating circuit 1520 to deliver an electric field using one or more frequencies selected from a range of within 10 kHz to 1 MHz. In some embodiments, the control circuitry 1506 can be configured to direct the electric field generating circuit 1520 to deliver an electric field at one or more frequencies selected from a range of within 100 kHz to 500 kHz. In some embodiments, the control circuitry 1506 can be configured to direct the electric field generating circuit 1520 to deliver an electric field at one or more frequencies selected from a range of within 100 kHz to 300 kHz. In some embodiments, the control circuitry 1506 can be configured to direct the electric field generating circuit 1520 to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry 1506 can be configured to direct the electric field generating circuit 1520 to deliver an electric field using currents ranging from 1 mAmp to 1000 mAmp to the site of a cancerous tumor. In some embodiments, the control circuitry 1506 can be configured to direct the electric field generating circuit 1520 to deliver an electric field using currents ranging from 20 mAmp to 500 mAmp to the site of a cancerous tumor. In some embodiments, the control circuitry 1506 can be configured to direct the electric field generating circuit 1520 to deliver an electric field using currents ranging from 30 mAmp to 300 mAmp to the site of a cancerous tumor.

In some embodiments, the control circuitry 1506 can be configured to direct the electric field generating circuit 1520 to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit 1520 to deliver an electric field at a current falling within a range, wherein any of the forgoing currents can serve as the lower or upper bound of the range, provided that the lower bound of the range is a value less than the upper bound of the range.

In some embodiments, the control circuitry 1506 can be configured to direct the electric field generating circuit 1520 to deliver an electric field using voltages ranging from 1 $V_{rms}$ to 50 $V_{rms}$ to the site of a cancerous tumor. In some embodiments, the control circuitry 1506 can be configured to direct the electric field generating circuit 1520 to deliver an electric field using voltages ranging from 5 $V_{rms}$ to 30 $V_{rms}$ to the site of a cancerous tumor. In some embodiments, the control circuitry 1506 can be configured to direct the electric field generating circuit 1520 to deliver an electric field using voltages ranging from 10 $V_{rms}$ to 20 $V_{rms}$ to the site of a cancerous tumor.

In some embodiments, the control circuitry 1506 can be configured to direct the electric field generating circuit 1520 to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit 1520 to deliver an electric field using a voltage falling within a range, wherein any of the forgoing voltages can serve as the lower or upper bound of the range, provided that the lower bound of the range is a value less than the upper bound of the range.

In some embodiments, the control circuitry 1506 can be configured to direct the electric field generating circuit 1520 to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit 1520 can deliver an electric field using a frequency falling within a range, wherein any of the foregoing frequencies can serve as the upper or lower bound of the range, provided that the upper bound is greater than the lower bound.

In some embodiments, the control circuitry 1506 can be configured to direct the electric field generating circuit 1520 to generate one or more applied electric field strengths selected from a range of within 0.25 V/cm to 1000 V/cm. In some embodiments, the control circuitry 1506 can be configured to direct the electric field generating circuit 1520 to generate one or more applied electric field strengths of greater than 3 V/cm. In some embodiments, the control circuitry 1506 can be configured to direct the electric field generating circuit 1520 to generate one or more applied electric field strengths selected from a range of within 1 V/cm to 10 V/cm. In some embodiments, the control circuitry 1506 can be configured to direct the electric field generating circuit 1520 to generate one or more applied electric field strengths selected from a range of within 3 V/cm to 5 V/cm.

In other embodiments, the control circuitry 1506 can be configured to direct the electric field generating circuit 1520 to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0 V/cm, 800.0 V/cm, 900.0 V/cm, 1000.0 V/cm. It will be appreciated that the electric field generating circuit 1520 can generate an electric field having a field strength at a treatment site falling within a range, wherein any of the foregoing field strengths can serve as the upper or lower bound of the range, provided that the upper bound is greater than the lower bound.

In some embodiments, the control circuitry 1506 can be configured to direct the electric field generating circuit 1520 to deliver an electric field via leads 1106 to the site of a cancerous tumor located within a bodily tissue. In other embodiments, the control circuitry 1506 can be configured to direct the electric field generating circuit 1520 to deliver an electric field via the housing 1102 of medical device 1100 to the site of a cancerous tumor located within a bodily tissue. In other embodiments, the control circuitry 1506 can be configured to direct the electric field generating circuit 1520 to deliver an electric field between leads 1106 and the housing 1102 of medical device 1100. In some embodiments, one or more leads 1106 can be in electrical communication with the electric field generating circuit 1520. In some embodiments, the one or more leads 1106 can include one or more electrodes 1108 disposed along the length of the leads 1106, where the electrodes 1108 can be in electrical communication with the electric field generating circuit 1520.

In some embodiments, various components within medical device 1100 can include an electric field sensing circuit 1522 configured to generate a signal corresponding to sensed electric fields. Electric field sensing circuit 1522 can be integrated with control circuitry 1506 or it can be separate from control circuitry 1506.

Sensing electrodes can be disposed on or adjacent to the housing of the medical device, on one or more leads connected to the housing, on a separate device implanted near or in the tumor, or any combination of these locations. In some embodiments, the electric field sensing circuit 1522 can include a first sensing electrode 1532 and a second sensing electrode 1534. In other embodiments, the housing 1102 itself can serve as a sensing electrode for the electric field sensing circuit 1522. The electrodes 1532 and 1534 can be in communication with the electric field sensing circuit 1522. The electric field sensing circuit 1522 can measure the electrical potential difference (voltage) between the first electrode 1532 and the second electrode 1534. In some embodiments, the electric field sensing circuit 1522 can measure the electrical potential difference (voltage) between the first electrode 1532 or second electrode 1534, and an electrode disposed along the length of one or more leads 1106. In some embodiments, the electric field sensing circuit can be configured to measure sensed electric fields and to record electric field strength in V/cm.

It will be appreciated that the electric field sensing circuit 1522 can additionally measure an electrical potential difference between the first electrode 1532 or the second electrode 1534 and the housing 1102 itself. In other embodiments, the medical device can include a third electrode 1536, which can be an electric field sensing electrode or an electric field generating electrode. In some embodiments, one or more sensing electrodes can be disposed along lead 1106 and can serve as additional locations for sensing an electric field. Many combinations can be imagined for measuring electrical potential difference between electrodes disposed along the length of one or more leads 1106 and the housing 1102 in accordance with the embodiments herein.

In some embodiments, the one or more leads 1106 can be in electrical communication with the electric field generating circuit 1520. The one or more leads 1106 can include one or more electrodes 1108, as shown in FIG. 11. In some embodiments, various electrical conductors, such as electrical conductors 1526 and 1528, can pass from the header 1104 through a feed-through structure 1530 and into the interior volume 1502 of medical device 1100. As such, the electrical conductors 1526 and 1528 can serve to provide electrical communication between the one or more leads 1106 and control circuitry 1506 disposed within the interior volume 1502 of the housing 1102.

In some embodiments, recorder circuitry can be configured to record the data produced by the electric field sensing circuit 1522 and record time stamps regarding the same. In some embodiments, the control circuitry 1506 can be hardwired to execute various functions, while in other embodiments the control circuitry 1506 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 16:
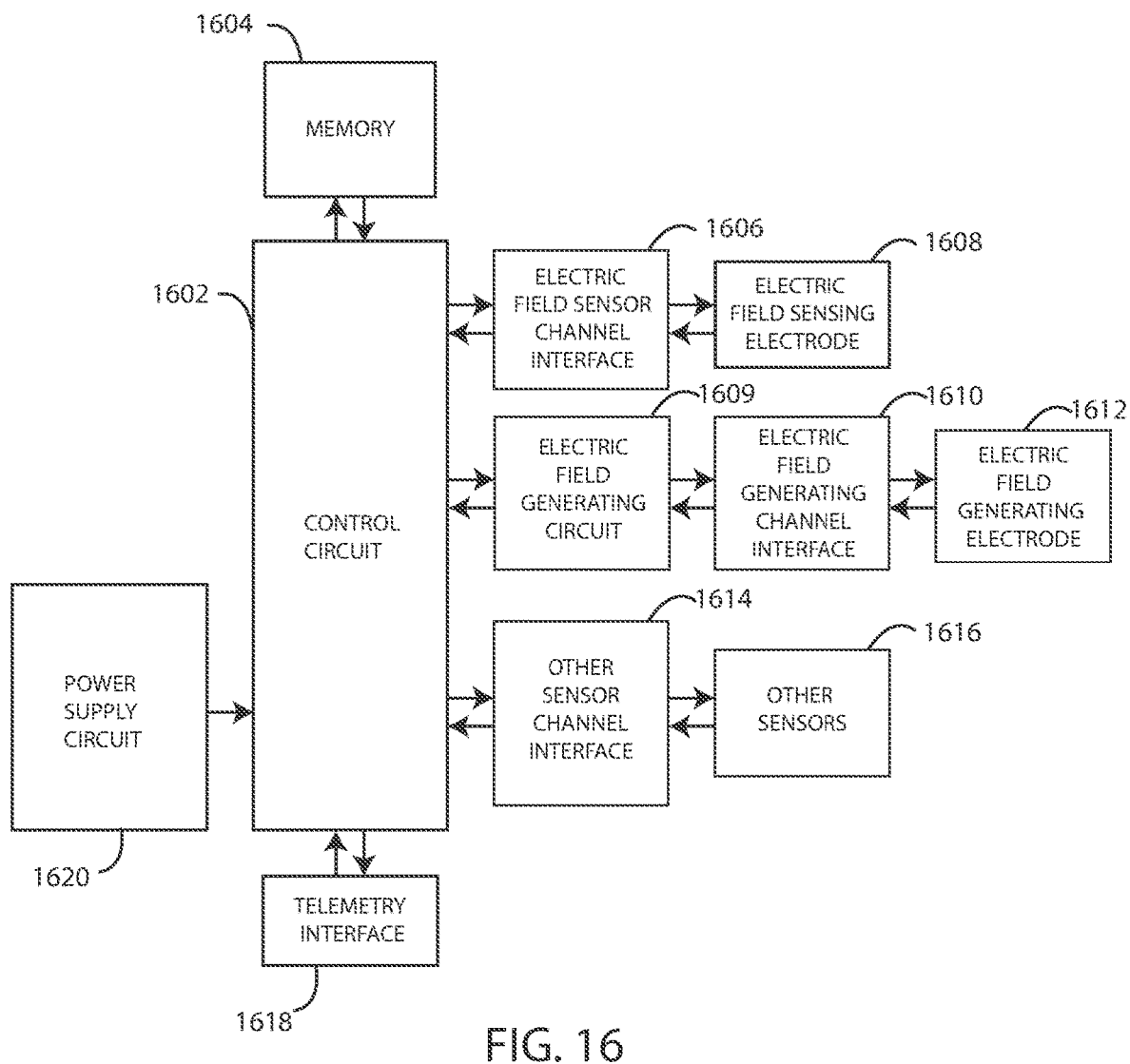
FIG. 16 is a schematic diagram of components of a medical device in accordance with various embodiments herein.

Elements of various embodiments of the medical devices described herein are shown in FIG. 16. However, it will be appreciated that some embodiments can include additional elements beyond those shown in FIG. 16. In addition, some embodiments may lack some elements shown in FIG. 16. The medical devices as embodied herein can gather information through one or more sensing channels and can output information through one or more field generating channels. A microprocessor 1602 can communicate with a memory 1604 via a bidirectional data bus. The microprocessor 1602 can be in electric communication with power supply circuit 1620. The memory 1604 can include read only memory (ROM) or random access memory (RAM) for program storage and RAM for data storage. The microprocessor 1602 can also be connected to a telemetry interface 1618 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. In some embodiments, the medical device can include an inductive energy receiver coil interface (not shown) communicatively coupled or attached thereto to facilitate transcutaneous recharging of the medical device.

The medical device can include one or more electric field sensing electrodes 1608 and one or more electric field sensor channel interfaces 1606 that can communicate with a port of microprocessor 1602. The medical device can also include one or more electric field generating electrodes 1612 and one or more electric field generating channel interfaces 1610 and one or more electric field generating circuits 1609 that can communicate with a port of microprocessor 1602. The medical device can also include one or more other sensors 1616, such as physiological sensors, respiration sensors, or chemical sensors, and one or more other sensor channel interfaces 1614 that can communicate with a port of microprocessor 1602. The channel interfaces 1606, 1610, and 1614 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

In some embodiments, the physiological sensors can include sensors that monitor temperature, blood flow, blood pressure, and the like. In some embodiments, the respiration sensors can include sensors that monitor respiration rate, respiration peak amplitude, and the like. In some embodiments, the chemical sensors can measure the quantity of an analyte present in a treatment area about the sensor, including but not limited to analytes such as of blood urea nitrogen, creatinine, fibrin, fibrinogen, immunoglobulins, deoxyribonucleic acids, ribonucleic acids, potassium, sodium, chloride, calcium, magnesium, lithium, hydronium, hydrogen phosphate, bicarbonate, and the like. However, many other analytes are also contemplated herein. Exemplary chemical/analyte sensors are disclosed in commonly owned U.S. Pat. No. 7,809,441 to Kane et al., and which is hereby incorporated by reference in its entirety.

Although the other sensors 1616 are shown as part of a medical device in FIG. 16, it is realized that in some embodiments one or more of the other sensors could be physically separate from the medical device. In various embodiments, one or more of the other sensors can be within another implanted medical device communicatively coupled to a medical device via telemetry interface 1618. In yet other embodiments, one or more of the other sensors can be external to the body and coupled to a medical device via telemetry interface 1618. In some embodiments, the other sensors can include drug delivery sensors, biopsy apparatus sensors, optical sensors, or irrigation sensors.

In some embodiments, the medical devices herein can include an electric field generating circuit configured to generate one or more electric fields at or near a site of the cancerous tumor. The medical devices herein can include control circuitry in communication with the electric field generating circuit, the control circuitry configured to control delivery of the one or more electric fields from the electric field generating circuit at or near the site of the cancerous tumor. The control circuitry can cause the electric field generating circuit to generate one or more electric fields at frequencies selected from a range of between 10 kHz to 1 MHz at the site of a cancerous tumor located within a bodily tissue, the one or more electric fields effective to delay mitosis and cause mitotic synchronization within a proportion of the cancerous cell population. In some embodiments, the medical device further can include one or more electrical leads in electrical communication with the electric field generating circuit.

In some embodiments, the medical devices herein include a medical device system for treating a cancerous tumor. The medical device housing can include an electric field generating circuit configured to generate one or more electric fields at or near a site of the cancerous tumor, the cancerous tumor including a cancerous cell population. The medical device system can include control circuitry in communication with the electric field generating circuit, where the control circuitry is configured to control delivery of the one or more electric fields from the electric field generating circuit at or near the site of the cancerous tumor. The medical device system can include a drug delivery catheter for administering one or more chemotherapeutic agents at or near the site of the cancerous tumor. The control circuitry of the medical device system causes the electric field generating circuit to generate one or more electric fields at frequencies selected from a range of between 10 kHz to 1 MHz at the site of a cancerous tumor located within a bodily tissue, the one or more electric fields effective to delay mitosis and cause mitotic synchronization within a proportion of the cancerous cell population.

In some embodiments, the medical devices herein can include a medical device for treating a cancerous tumor located within a subject. The medical device can include an electric field generating circuit configured to generate one or more electric fields at or near a site of the cancerous tumor, the cancerous tumor including a cancerous cell population. The medical device can include control circuitry in communication with the electric field generating circuit. The control circuitry of the medical devices controls delivery of the one or more electric fields from the electric field generating circuit at or near the site of the cancerous tumor by following a predefined schedule that causes the electric fields to vary in at least one of intensity and frequency over the course of a defined time period of at least six hours.

The medical devices herein can include a medical device for treating a cancerous tumor, including one or more implantable electrodes configured for placement on the inside of a body of a subject with the cancerous tumor. The medical device can include one or more external electrodes configured for placement on an outside surface of the body of the subject. The medical device can include an electric field generating circuit configured for generating an electric field between at least one pair of electrodes according to a predefined schedule, the electric field having frequencies within a range of between 10 kHz to 1 MHz. The medical device can include control circuitry configured for receiving a pause command from the subject, wherein the pause command causes cessation of generating the electric field.

Chemotherapeutic Agents

One or more chemotherapeutic agents can be suitable for use with the methods and devices described herein. In some embodiments, the therapeutic agents suitable for use herein can include antimitotic agents. The anti-mitotic agents can include anti-mitotic agents that act on the microtubules (i.e., spindle fiber) present during mitosis. Suitable anti-mitotic agents can include those that have microtuble-stabilizing properties or those that have microtuble-destablizing properties. Without wishing to be bound by any particular theories, it is believed that anti-mitotic agents including those that have microtuble-stablizing properties or those that have microtuble-destablizing properties act on various domains of either alpha-tubulin or beta-tubulin proteins that make up the microtubule structure.

In some embodiments, the anti-mitotic agents herein can include anti-mitotic agents that act on the contractile ring, which can include, but are not to be limited to F-actin, myosin-2, anillin, one or more septins, Rho, profilin, cofilin, and male germ cell Ras-related C3 botulinum toxin substrate GTPase activating proteins (MgcRacGAP). In other embodiments, the anti-mitotic agents can include anti-miotic agents that act on nuclei acids, such as DNA and RNA. Suitable anti-mitotic agents can include those that have contractile ring—stabilizing properties or those that have contractile ring—destabilizing properties. Without wishing to be bound by any particular theories, it is believed that anti-mitotic agents including those that have contractile ring—stabilizing properties or those that have contractile ring—destabilizing properties act on various domains of the proteins that form the contractile ring, as discussed herein.

Chemotherapeutic agents suitable for use herein include, but are not to be limited to, at least one of vindesine, vincristine, vinblastine, paclitaxel, docetaxel, 2-methoxyestradiol, patupilone, trastuzumab emtansine, and derivatives thereof. In some embodiments, the chemotherapeutic agents herein include those that have a therapeutic half-life of less than 24 hours. In some embodiments, the chemotherapeutic agents herein include those that have a therapeutic half-life of less than 48 hours. In some embodiments, the chemotherapeutic agents herein include those that have a therapeutic half-life of less than 60 hours.

The chemotherapeutic agents herein can be administered at or near the site of the cancerous tumor in a therapeutically effective dose. In some embodiments, the chemotherapeutic agents herein can be administered away from the site of the cancerous tumor into the systemic circulation in a therapeutically effective does. The chemotherapeutic agents can be administered through a transcutaneous access port that is in fluid communication with the systemic venous system anywhere on the subject's body.

In some embodiments, a therapeutically effective dose of chemotherapeutic agent includes a concentrated dosage amount delivered to the subject within a 6-hour time period following removal of the electric field, where the concentrated dosage amount is equivalent to a conventional non-concentrated dosage amount delivered over a 24-hour time period. In some embodiments, a concentrated dosage amount of the chemotherapeutic agent can delivered to the subject within one or two hours, In some embodiments, a concentrated dosage amount of the chemotherapeutic agent can delivered to the subject under one or two hours, followed by an administration of a dilute dosage of the chemotherapeutic agent for a predetermined period of time, which can include 6 hours, 12 hours, 24 hours, 48 hours, 72 hours, or longer, where the concentrated dosage amount is equivalent to a conventional non-concentrated dosage amount delivered within a 24-hour time period to a 72-hour time period range.

The chemotherapeutic agents herein can include optically activated chemotherapeutic agent. The optically activated chemotherapeutic agents can include, but are not to be limited to, photoactivated platinum compounds or photoactivated photostatin compounds. In some embodiments, the photoactivated photostatin compounds include light-activated combretastatin A-4, and analogs and derivatives thereof. In some embodiments, the optically activated chemotherapeutic agents can be optically activated by visible light emitted by optical emitters present on various leads described herein within the range of 350 nm to 850 nm. In some embodiments, the optically activated chemotherapeutic agents can be optically activated by visible light within the range of 450 nm to 650 nm. The optically activated chemotherapeutic agents herein can include those that are optically activated by a wavelength that can be greater than or equal to 350 nm, 400 nm, 450 nm, 500 nm, 550 nm, 600 nm, 650 nm, 700 nm, 750 nm, 800 nm, or 850 nm, or can be an amount falling in a range within any of the foregoing. In some embodiments, the optically activated chemotherapeutic agents herein can be optically inactivated by visible light within the range of 350 nm to 850 nm. In some embodiments, the if the optically activated chemotherapeutic agents herein are optically inactivated by visible light within the range of 350 nm to 850 nm, the can be further activated by visible light within the range of 350 nm to 850 nm for multiple cycles.

Suitable optically activated chemotherapeutic agents include, but are not to be limited to, photoactivated platinum compounds or photoactivated photostatin compounds. In some embodiments, the photoactivated photostatin compounds include light-activated combretastatin A-4, and analogs and derivatives thereof.

The methods herein can include a method for treating a cancerous tumor located within a subject including applying one or more electric fields at or near a site of the cancerous tumor, the cancerous tumor including a cancerous cell population. The method can include removing the one or more electric fields and administering an optically activated chemotherapeutic agent at or near a site of the cancerous tumor after the one or more electric fields have been removed. The method can include irradiating the optically activated chemotherapeutic agent by delivering photoactivating light energy at or near the site of the cancerous tumor. In some embodiments, the optically activated chemotherapeutic agent is administered at a therapeutically effective dose of optically activated chemotherapeutic agent for release at or near the site of the cancerous tumor. In some embodiments, the therapeutically effective dose includes a concentrated dosage amount delivered to the subject within a 6-hour time period following removal of the electric field, where the concentrated dosage amount is equivalent to a conventional non-concentrated dosage amount delivered over a 24-hour time period.

The medical devices herein can include treating a cancerous tumor located within a subject including an electric field generating circuit configured to generate one or more electric fields at or near a site of the cancerous tumor, the cancerous tumor including a cancerous cell population. The medical device can include control circuitry in communication with the electric field generating circuit, the control circuitry configured to control delivery of the one or more electric fields from the electric field generating circuit at or near the site of the cancerous tumor. The medical device can include a catheter configured to administer an optically activated chemotherapeutic agent at or near a site of the cancerous tumor. The medical device can include one or more optical emitters configured to irradiate the optically activated chemotherapeutic agent by delivering photoactivating light energy at or near the site of the cancerous tumor.

The chemotherapeutic agents herein can include nanoparticles. In some embodiments, the nanoparticles are made from a polymer, such as a biodegradable polymer. In some embodiments, the nanoparticles can include an effective amount of chemotherapeutic agent for release at or near the site of the cancerous tumor. In some embodiments, the nanoparticles include at least one of the vindesine, vincristine, vinblastine, paclitaxel, docetaxel, 2-methoxyestradiol, patupilone, trastuzumab emtansine, and derivatives thereof. The nanoparticles can be released at or near the site of a cancerous tumor to deliver a therapeutically effective dose of optically active chemotherapeutic agent. In some embodiments, the therapeutically effective dose includes a concentrated dosage amount delivered to the subject within a 6-hour time period following removal of the electric field, where the concentrated dosage amount is equivalent to a conventional non-concentrated dosage amount delivered over a 24-hour time period. In some embodiments, the nanoparticles can include an effective amount of optically activated chemotherapeutic agent, as described elsewhere herein.

The methods herein can include a method for treating a cancerous tumor located within a subject, including applying one or more electric fields at or near a site of the cancerous tumor, the cancerous tumor including a cancerous cell population. The method can include administering nanoparticles including a chemotherapeutic agent at or near the site of the cancerous tumor. In some embodiments, the method can include removing the one or more electric fields before administering the nanoparticles at or near the site of the cancerous tumor.

The medical devices herein can include a medical device for treating a cancerous tumor located within a subject including an electric field generating circuit configured to generate one or more electric fields at or near a site of the cancerous tumor, the cancerous tumor including a cancerous cell population. The medical device can include control circuitry in communication with the electric field generating circuit, the control circuitry configured to control delivery of the one or more electric fields from the electric field generating circuit at or near the site of the cancerous tumor. The medical device can include a catheter configured to administer an nanoparticles at or near a site of the cancerous tumor.

Additional Agents and Modalities

One or more additional agents or modalities can be suitable for use with the methods and devices described herein. By way of example, an immunologic agent can be combined with an alternating electric field therapy. Suitable immunologic agents can include, but are not to be limited to, immunostimulant agents and immunosuppressive agents. In some embodiments, an immunostimulant can include one or more agents that stimulate the immune system. In other embodiments, an immunosuppressive can include one or more agents that suppress the immune system. In some embodiments, a combination of immunostimulant agents and immunosuppressive agents can be used. In other embodiments, and immunostimulant agent and/or an immunosuppressive agent can be used in conjunction with a chemotherapeutic agent during a given therapy.

Exemplary immunostimulant agents can include bacterial vaccines, viral vaccines, therapeutic vaccines, interferons, interleukins, colony stimulating factors, male and female sex hormones, growth hormone, vitamin D, and the like. In some embodiments the immunostimulant agent can be specific, while in other embodiments the immunostimulant agent can be non-specific. Exemplary immunosuppressive agents can include calcineurin inhibitors, interleukin inhibitors, TNF alpha inhibitors, antibodies, glucocorticoids, cytostatics, alkylating agents, antimetabolites such as nucleotide analogs, protein synthesis inhibitors, anti-rejection agents, and the like.

One or more additional modalities or agents can also be suitable for use with the methods and devices described herein. By way of example, use of radiation therapy in conjunction with alternating electric field therapy is also contemplated herein. In some embodiments, targeted drug therapy, immunotherapy, or hormone therapy can be used in conjunction with alternating electric field therapies described herein.

Applied Electric Fields

The electric fields applied to the cancerous tumors using the methods herein can be applied using a variety of modalities. Exemplary therapeutic parameter sets can include those that implement the following concepts: sweeping through a range of frequencies; stacking of one or more frequencies simultaneously; stepping through one or more frequencies sequentially; the spatial or temporal delivery of one or more electric fields; sweeping through a range of electric field strengths; applying an effective rotating electric field; modulating a voltage control mode or a current control mode; implementing one or more duty cycles; pulse width modulation; manipulation of the electrical waveform shape and/or pulse sequence; and the occasional use of high frequency or high electric fields strength pulses.

The therapeutic parameter sets can be programmed into a medical device to operate autonomously, or they can be queried and manipulated by the subject or a clinician using an external computation device such as a programmer, a home-based unit, and/or a mobile unit (e.g. a cellular phone, personal computer, smart phone, tablet computer, and the like). In other embodiments, the therapeutic parameter sets can be wirelessly communicated to the medical device from an external computation device. Frequencies and/or electric field strengths suitable for use in any of the therapeutic parameter sets herein are discussed above with respect to electric field generating circuit. In some embodiments, one or more therapeutic parameter sets can be implemented simultaneously. In other embodiments, one or more therapeutic parameter sets can be implemented in an alternating fashion.

Figure 17:
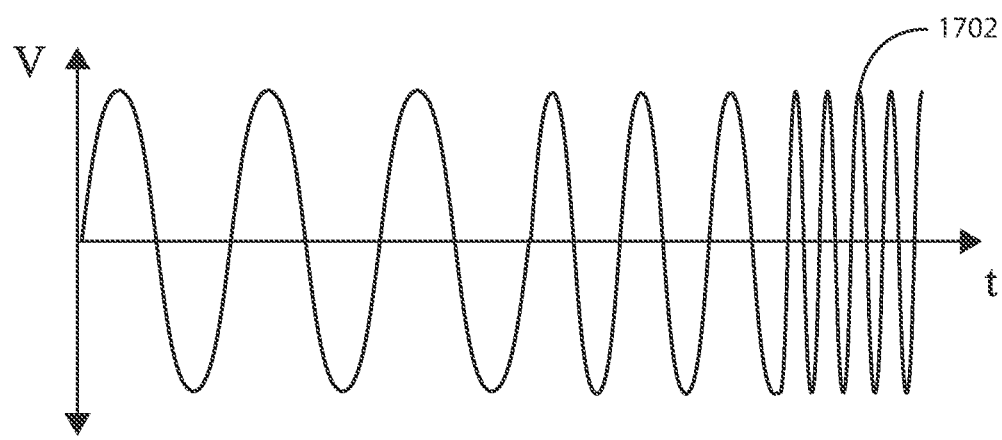
FIG. 17 is a plot of an exemplary electric field in accordance with various embodiments herein.
Figure 18:
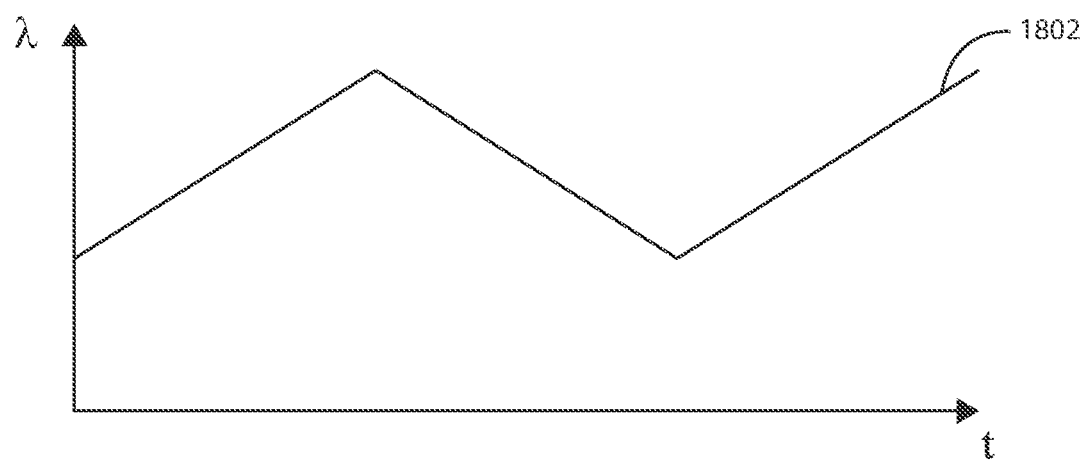
FIG. 18 is a plot of an exemplary electric field in accordance with various embodiments herein.

By way of example, an electric field can be applied to the site of a cancerous tumor by sweeping through a range of frequencies. Referring now to FIG. 17, exemplary plot 1702 shows an alternating electric field, where the frequency of the increases over time. Similarly, FIG. 18 shows the change in frequency as a function of time in exemplary plot 1802 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above with respect to electric field generating circuit 1609, provided that the lower end of each range is a value less than the upper end of each range. At times, it may be beneficial to have some amount of overlap between the frequency range of the first and second frequency sweep.

Leads and Electrodes

The leads described herein can be placed into the body at or near the site of a cancerous tumor using a number of techniques. Placement of one or more leads can include using techniques such as transvascular placement, tunneling into the subcutaneous space, and/or surgical placement. In some embodiments, the placement of one or more leads can include placement via one or more natural body orifices. The leads can be placed adjacent to or within a cancerous tumor. In some embodiments, multiple leads can be used near to or far from the cancerous tumor.

In some embodiments one or more leads described herein can be placed in the subcutaneous space. Electrodes on leads placed in the subcutaneous space can be used as the primary near-field generating electrode or as a far-field field generating electrode. In some embodiments, electrodes on leads placed in the subcutaneous space can be used as the primary near-field generating electrode or as a far-field field generating electrode in conjunction with the housing of a medical device. Likewise, one or more leads can be placed transvascularly to act as far-field field generating electrodes in conjunction with an electrode at or near the site of the cancerous tumor or in conjunction with the housing of a medical device.

The leads and electrodes described herein can include additional functional and structural features. In some embodiments, the leads can include those that are compatible with imaging and treatment techniques, including but not limited to MRI (magnetic resonance imaging), X-ray imaging, deep brain stimulation techniques, and/or radiation therapy. In some embodiments, the leads can include one or more conductor cores made from conducting materials. The conductor cores can be formed from conducting materials including metals and/or other conducting materials. Metals can include, but are not limited to, palladium, platinum, silver, gold, copper, aluminum, various alloys including stainless steel, nickel-cobalt alloys such as MP35N® and the like. In some embodiments, the conductor core can be a multifilar coil, including but not limited to a bifilar coil, a trifilar coil, and a quadfilar coil.

In some embodiments, electrodes can be disposed along the length of one or more leads as described herein. Suitable materials for use in the electrodes described herein can include metals such as palladium, to minimize coupling and artifact generation in magnetic fields. In some embodiments, electrodes can be made from other metals and/or other conducting materials. Metals can include, but are not limited to, palladium, platinum, platinum alloys such as platinum-iridium alloy, gold, copper, tantalum, titanium, various alloys including stainless steel, and the like. In some embodiments, electrodes can be in the form of wound coils that can provide an added benefit of increased surface area without compromising flexibility of the electrodes. In some embodiments, the implantable device housing can serve as an electrode.

The leads described herein can also include one or more electrodes disposed along the length of the lead. The leads can include two or more electrodes disposed along the length of the lead. In some embodiments, the electrodes can be tip electrodes found at the distal end of the lead. In other embodiments, the electrodes can be ring electrodes found along the lead but not at the tip of the lead.

In some embodiments, the electrodes can be coil electrodes. In some embodiments, a ring or tip electrode can be positioned in or adjacent to a tumor or cancerous tissue and a coil electrode can be positioned farther from the tumor or cancerous tissue in order to help provide spatial diversity to the generated electric fields. In some embodiments, one or more electrodes can have a length along the lengthwise axis (e.g., proximal to distal axis) of about 0.5, 1, 1.5, 2, 3, 4, 5, 7.5, 10, 15, 20, 30, 40, 50, 75, 100 mm or more. In some embodiments, one or more of the electrodes can have a length falling within a range wherein any of the foregoing distances can serve as the upper or lower bound of the range, provided that the upper bound is greater than the lower bound.

The leads can be unipolar, bipolar, or multipolar. In some embodiments, a unipolar lead can include a lead that generates an electric field between one electrode and the housing of the medical device. In some embodiments, a bipolar lead can include a lead that can generate and electric field between two electrodes disposed along the lead, or between both electrodes and the housing of the medical device. In some embodiments, a multipolar lead can include a lead that can generate an electric field between the more than two electrodes disposed along the lead, between more than two electrodes and the housing of the medical device, or any number of combinations of configurations of electrodes and the housing of the medical device.

The leads herein can include one or more optical emitters along the length of the lead. Optical emitters suitable for use herein can include those that emit light that falls anywhere along the visible spectrum from about 350 nm to 950 nm. Suitable optical emitters can include light emitting diodes or laser diodes. Suitable LEDs can be made from one or more of gallium arsenide (GaAs), gallium phosphide (GaP), gallium arsenide phosphide (GaAsP), silicon carbide (SiC) or fallium indium nitride (GaInN). In some embodiments, the LEDs suitable for use herein can include an LED capable of emitting only one color, or a mono-color LED; an LED capable of emitting two colors, or a bi-color LED; an LED capable of emitting three colors, or a tri-color LED; or an LED capable of emitting more than three colors. The LEDs can be in electrical communication with control circuitry within the housing of the medical devices described herein. In some embodiments, one or more laser diodes can be included along the leads herein, and the laser diodes can be in optical communication with one or more optical fibers disposed within the leads and used for transmitting light from a laser source to a laser diode.

The electrodes suitable for use here can be made of conductive polymers such as carbon filled silicone, polyacetylene, polypyrrole, polyaniline, polytiophene, polyfuran, polyisoprene, polybutadiene, polyparaphenylene, and the like. In other embodiments, the electrodes can be insulated. In some embodiments, the insulation surrounding and electrode can include microporous insulators to prevent cellular apposition, yet still allow for current flow. Microporous insulators can be made from a number of the insulating materials described herein, including but not limited to polytetrafluoroethylene (ePTFE), polyethylene-co-tetrafluoroethene (ETFE), polyurethanes, silicones, poly(p-xylylene) polymers such as Parylene polymers, polyether block amides such as PEBAX®, nylons, or derivatives thereof. In some embodiments, the electrodes can be coated with various materials, including but not limited to hydrogels or fractal coatings such as iridium oxide, titanium oxide, tantalum pentoxide, other metal oxides, poly(p-xylylene) polymers such as Parylene, and the like.

A number of lead fixation techniques and configurations can be used in accordance with the embodiments herein. Some non-limiting examples of lead fixation techniques can include biocompatible glue fixation, talon fixation, helix coil fixation, passive centering of the lead in the vascular system, tine fixation within the localized vascular system, spiral bias fixation within the localized vascular system, compression fixation, suture sleeve fixation, and the like. In some examples, the leads embodied herein can be placed within the vascular system surrounding or adjacent to the site of the cancerous tumor. In other embodiments, the leads embodied herein can be place surgically at or within or surrounding the site of the cancerous tumor.

The leads suitable for use herein can also include one or more open lumens that run the entire longitudinal length of, or a select portion of the longitudinal length of the lead. In some embodiments, the open lumen can include an integrated biopsy apparatus suitable for obtaining biopsy samples from a cancerous tumor site on a periodic basis to monitor disease progression and/or regression. Leads having an open lumen can also be configured to include an integrated drug delivery lumen that can deliver one or more drugs, such as steroids or chemotherapy agents, to the site of the tumor in a single bolus or periodically via a metered pump. The leads can include one or more portals disposed along the length of the lead to provide an outlet for drug delivery at or near the site of a cancerous tumor.

In some embodiments a portion of the lead or the entire lead can include a drug eluting coating. In some embodiments, the drug eluting coating can include an anti-inflammatory agent, such as a steroid. In some embodiments, the steroid can be dexamethasone. In other embodiments, the drug eluting coating can include a chemotherapy agent. In some embodiments, the chemotherapy agent can include a taxane or derivatives thereof, including but not limited to paclitaxel, docetaxel, and the like. In other embodiments, the drug eluting coating can be configured to release additional classes of chemotherapy agents, including, but not limited to alkylating agents, plant alkaloids such as vinca alkaloids, cytotoxic antibiotics, topoisomerase inhibitors, and the like. In some embodiments, the drug eluting coating can be configured to release the drug from the coating in a time-release fashion.

The leads herein can adopt a number of shapes or configurations. In some embodiments, the leads can be linear and in other embodiments the leads can be circular. A circular lead may be a completely closed loop or it may be a semi-closed loop. In some embodiments, the lead can include a bendable core that can allow the lead to be shaped into many configurations, including but not limited to a U shape, an S shape, a spiral shape, a half circle, an oval, and the like.

In yet other examples, the leads suitable for use herein can include fluorimetric or magnetic markers that can assist the clinician in precise placement at or near the site of a cancerous tumor. The leads can also include integrated pH sensors for detecting the change in the pH at or near the cancerous tumor or other chemical sensors suitable for analyzing the concentration of a chemical analyte of interest.

Electric Field Generators

The medical devices embodied herein can include electric field generators particularly suited for therapeutic and diagnostic techniques used during the course of treatment for a cancerous tumor. In some embodiments, the electric field generators suitable for use herein can include those that have been treated by radiation hardening to make the components resistant to the damaging effects of radiation therapy treatments often prescribed as a main line treatment for cancerous tumors. Electric field generators can include components such as those described in reference to FIGS. 3 and 5 above.

Electric field generators embodied herein can be programmed with any number of therapeutic parameter sets as described. The electric field generators can be programmed prior to implant, or they can be programmed by a clinician using an external computation device such as a programmer, a home-based unit, and/or a mobile unit (e.g. a cellular phone, personal computer, smart phone, tablet computer, and the like). In some embodiments, therapy parameters can be delivered to the electric field generator via a telemetry circuit. In some embodiments, the electric field generator can include a recharge circuit communicatively coupled to a receiver coil to facilitate transcutaneous recharging of the medical device. In some embodiments, the electric field generator can communicate wirelessly between the receiver coil and an external charging device.

Further Embodiments

In an embodiment, a method for treating a cancerous tumor located within a subject is included, the method including applying one or more electric fields at or near a site of the cancerous tumor, the cancerous tumor can include a cancerous cell population; wherein the one or more applied electric fields are effective to delay mitosis and cause mitotic synchronization within a proportion of the cancerous cell population; removing the one or more electric fields to allow mitosis to proceed within the cancerous cell population; and administering a chemotherapeutic agent to the subject after the one or more electric fields have been removed.

In an embodiment, applying the one or more electric fields to the cancerous tumor includes applying the one or more electric fields over a time period selected from a range of time periods from 1 minute to 24 hours.

In an embodiment, a method further can include administering the chemotherapeutic agent to the subject when at least 5% of the cancerous cell population is synchronized in mitosis in response to the one or more electric fields.

In an embodiment, a method further can include administering the chemotherapeutic agent to the subject when at least 25% of the cancerous cell population is synchronized in mitosis in response to the one or more electric fields.

In an embodiment, a method further can include administering the chemotherapeutic agent to the subject when at least 50% of the cancerous cell population is synchronized in mitosis in response to the one or more electric fields.

In an embodiment, a method further can include administering the chemotherapeutic agent to the subject when at least 75% of the cancerous cell population is synchronized in mitosis in response to the one or more electric fields.

In an embodiment, the one or more electric fields are applied to the cancerous tumor at frequencies selected from a range of between 10 kHz to 1 MHz.

In an embodiment, the one or more electric fields are applied to the cancerous tumor at frequencies selected from a range of between 100 kHz to 500 kHz.

In an embodiment, the one or more electric fields are applied to the cancerous tumor at frequencies selected from a range of between 100 kHz to 300 kHz.

In an embodiment, the one or more electric fields include an electric field strength selected from a range of electric field strengths from 0.25 V/cm to 1000 V/cm.

In an embodiment, the one or more electric fields include an electric field strength selected from a range of electric field strengths from 1 V/cm to 10 V/cm.

In an embodiment, the one or more electric fields include an electric field strength selected from a range of electric field strengths from 3 V/cm to 5 V/cm.

In an embodiment, the chemotherapeutic agent is administered to the subject in a therapeutically effective dose.

In an embodiment, the therapeutically effective dose includes a concentrated dosage amount delivered to the subject within a 6-hour time period following removal of the electric field, the concentrated dosage amount being equivalent to a conventional non-concentrated dosage amount delivered over a 24-hour time period.

In an embodiment, the chemotherapeutic agent includes an agent with a therapeutic half-life of less than 48 hours.

In an embodiment, the chemotherapeutic agent includes an anti-mitotic agent.

In an embodiment, the chemotherapeutic agent includes at least one of vindesine, vincristine, vinblastine, paclitaxel, docetaxel, 2-methoxyestradiol, patupilone, trastuzumab emtansine, and derivatives thereof.

In an embodiment, the chemotherapeutic agent includes an optically activated chemotherapeutic agent.

In an embodiment, the optically activated chemotherapeutic agent includes photoactivated platinum compounds or photoactivated photostatin compounds.

In an embodiment, the photoactivated photostatin compounds include light-activated combretastatin A-4, and analogs and derivatives thereof.

In an embodiment, the optically activated chemotherapeutic agent can be optically activated by visible light within a range of 350 nm to 850 nm.

In an embodiment, the optically activated chemotherapeutic agent can be optically inactivated by visible light within a range of 350 nm to 850 nm.

In an embodiment, the chemotherapeutic agent includes nanoparticles.

In an embodiment, the nanoparticles include an effective amount of chemotherapeutic agent for release at or near the site of the cancerous tumor.

In an embodiment, a method further can include inserting a transcutaneous access port at or near the site of the cancerous tumor.

In an embodiment, the transcutaneous access port is configured to accept one or more leads.

In an embodiment, the one or more leads include: drug delivery catheters having an open lumen for delivery of one or more chemotherapeutic agents; optical leads can include one or more optical emitters for delivering photoactivating light energy; a biopsy apparatus for obtaining a biopsy sample from the cancerous tumor; and irrigation catheters for flushing waste products or bodily fluids.

In an embodiment, applying the one or more electric fields to the subject includes applying the one or more electric fields to an exterior of the subject at or near the site of the cancerous tumor.

In an embodiment, applying the one or more electric fields to the cancerous tumor includes applying the one or more electric fields at least partially to an interior of the subject at or near the site of the cancerous tumor.

In an embodiment, applying the one or more electric fields to the cancerous tumor includes applying the one or more electric fields at least partially to an exterior of the subject at or near the site of the cancerous tumor.

In an embodiment, applying the one or more electric fields to the cancerous tumor includes applying the one or more electric fields with one or more implantable electrodes within an interior of the subject at or near the site of the cancerous tumor.

In an embodiment, the medical device generating the one or more electric fields can include: an electric field generating circuit; and control circuitry in communication with the electric field generating circuit, the control circuitry configured to control delivery of the one or more electric fields from the electric field generating circuit at or near the site of the cancerous tumor.

In an embodiment, the medical device further includes one or more electrical leads in electrical communication with the electric field generating circuit.

In an embodiment, the medical device is configured to be implanted entirely within the subject.

In an embodiment, the medical device is configured to be entirely external to the subject.

In an embodiment, the medical device is configured to be partially implanted within the subject.

In an embodiment, the medical device is configured to be partially external to the subject.

In an embodiment, a method for of treating a cancerous tumor is included, the method including implanting one or more implantable electrodes inside a body of a subject with the cancerous tumor; placing one or more external electrodes on an outside surface of the body of the subject; generating an electric field between at least one pair of electrodes according to a predefined schedule, the electric field having frequencies within a range of between 10 kHz to 1 MHz; and removing the one or more electric fields; and administering a chemotherapeutic agent at or near a site of the cancerous tumor after the one or more electric fields have been removed.

In an embodiment, the one or more applied electric fields are effective to delay mitosis and cause mitotic synchronization within a proportion of the cancerous cell population.

In an embodiment, removing the one or more electric fields allows mitosis to proceed within the cancerous cell population.

In an embodiment, a method for treating a cancerous tumor located within a subject is included, the method including applying a first electric field having a first field strength at or near a site of the cancerous tumor, the cancerous tumor can include a cancerous cell population; wherein the first electric field is effective to delay mitosis and cause mitotic synchronization within a proportion of the cancerous cell population; removing the first electric field to allow mitosis to proceed within the cancerous cell population; and administering a chemotherapeutic agent at or near a site of the cancerous tumor after the first electric field has been removed.

In an embodiment, the method can further include applying a second electric field having a second electric field strength at or near the site of the cancerous tumor after removing the first electric field and prior to administering the chemotherapeutic agent, wherein the second electric field is effective to delay mitosis and cause mitotic synchronization within a proportion of the cancerous cell population.

In an embodiment, the method can further include waiting a predetermined amount of time after removing the first electric field prior to applying the second electric field.

In an embodiment, the second electric field strength is less than the first electric field strength.

In an embodiment, the second electric field strength is greater than the first electric field strength.

In an embodiment, the second electric field strength is the same as the first electric field strength.

In an embodiment, the method can further include receiving a pause command from the subject to pause the application of the first electric field when the subject experiences one or more side effects can include dizziness, nausea, fatigue, light headedness, headache, or localized pain.

In an embodiment, the method can further include receiving an on command from the subject, wherein the on command reestablishes generating the first electric field.

In an embodiment, a medical device for treating a cancerous tumor is included having an electric field generating circuit configured to generate one or more electric fields at or near a site of the cancerous tumor, the cancerous tumor can include a cancerous cell population; control circuitry in communication with the electric field generating circuit, the control circuitry configured to control delivery of the one or more electric fields from the electric field generating circuit at or near the site of the cancerous tumor; wherein the control circuitry causes the electric field generating circuit to generate one or more electric fields at frequencies selected from a range of between 10 kHz to 1 MHz at the site of a cancerous tumor located within a bodily tissue, the one or more electric fields effective to delay mitosis and cause mitotic synchronization within a proportion of the cancerous cell population.

In an embodiment, the medical device can include one or more electrical leads in electrical communication with the electric field generating circuit.

In an embodiment, the medical device can include one or more of: drug delivery catheters for delivery of one or more chemotherapeutic agents; optical leads can include one or more optical emitters for delivering photoactivating light energy; a biopsy apparatus for obtaining a biopsy sample from the cancerous tumor; and irrigation catheters for flushing waste products or bodily fluids.

In an embodiment, the medical device is configured to be implanted entirely within the subject.

In an embodiment, the medical device is configured to be partially implanted within the subject.

In an embodiment, the medical device is configured to be entirely external to the subject.

In an embodiment, a medical device system for treating a cancerous tumor is included having a medical device housing, the medical device housing is included having an electric field generating circuit configured to generate one or more electric fields at or near a site of the cancerous tumor, the cancerous tumor can include a cancerous cell population; control circuitry in communication with the electric field generating circuit, the control circuitry configured to control delivery of the one or more electric fields from the electric field generating circuit at or near the site of the cancerous tumor; a drug delivery catheter for administering one or more chemotherapeutic agents at or near the site of the cancerous tumor; and wherein the control circuitry causes the electric field generating circuit to generate one or more electric fields at frequencies selected from a range of between 10 kHz to 1 MHz at the site of a cancerous tumor located within a bodily tissue.

In an embodiment, the medical device can include a delivery port configured to receive at least one of: a drug delivery catheter for delivery of one or more chemotherapeutic agents; an optical lead can include one or more optical emitters for delivering optical energy; a biopsy apparatus for obtaining a biopsy sample from the cancerous tumor; and an irrigation catheter for flushing the site of the cancerous tumor.

In an embodiment, a method for treating a cancerous tumor located within a subject is included, the method applying one or more electric fields at or near a site of the cancerous tumor according to a predefined schedule, the cancerous tumor can include a cancerous cell population; wherein the predefined schedule causes the electric fields to vary in at least one of intensity and frequency over the course of a defined time period of at least six hours.

In an embodiment, the one or more applied electric fields are effective to delay mitosis and cause mitotic synchronization within a proportion of the cancerous cell population.

In an embodiment, a method can further include removing the one or more electric fields to allow mitosis to proceed within the cancerous cell population.

In an embodiment, a method can further include administering a chemotherapeutic agent at or near a site of the cancerous tumor after the one or more electric fields have been removed.

In an embodiment, a method can further include receiving a pause command from the subject, wherein the pause command causes cessation of applying the electric field.

In an embodiment, the predefined schedule includes temporal variation of at least one of the intensity and frequency of the one or more electric fields.

In an embodiment, the predefined schedule includes one or more predetermined down periods wherein the one or more applied electric fields is decreased in intensity or frequency by at least 50% for at least 4 hours.

In an embodiment, the predefined schedule includes one or more predetermined down periods wherein the one or more applied electric fields is decreased in intensity or frequency by at least 75% for at least 4 hours.

In an embodiment, a method for treating a cancerous tumor located within a subject is included, the method including applying one or more electric fields at or near a site of the cancerous tumor according to a predefined schedule, the cancerous tumor can include a cancerous cell population; wherein the one or more applied electric fields are effective to delay mitosis and cause mitotic synchronization within a proportion of the cancerous cell population; removing the one or more electric fields to allow mitosis to proceed within the cancerous cell population.

In an embodiment, a medical device for treating a cancerous tumor located within a subject is included having an electric field generating circuit configured to generate one or more electric fields at or near a site of the cancerous tumor, the cancerous tumor can include a cancerous cell population; control circuitry in communication with the electric field generating circuit; wherein the control circuitry is configured to control delivery of the one or more electric fields from the electric field generating circuit at or near the site of the cancerous tumor by following a predefined schedule that causes the electric fields to vary in at least one of intensity and frequency over the course of a defined time period of at least six hours.

In an embodiment, a method for of treating a cancerous tumor is included, the method including implanting one or more implantable electrodes inside a body of a subject with the cancerous tumor; placing one or more external electrodes on an outside surface of the body of the subject; generating an electric field between at least one pair of electrodes according to a predefined schedule, the electric field having frequencies within a range of between 10 kHz to 1 MHz; and receiving a pause command from the subject, wherein the pause command causes cessation of generating the electric field.

In an embodiment, a method can further include reinitiating generating the electric field between the at least one pair of electrodes according to the predefined schedule after a time period has elapsed after receiving the pause command from the subject.

In an embodiment, the predefined schedule includes temporal variation of at least one of the intensity and frequency of the electric field.

In an embodiment, the pause command received from the patient includes at least one of an off command, an off-for-a-set-time command, an off button depressed command, or an off-status reminder command.

In an embodiment, a method can include receiving an on command from the subject, wherein the on command reestablishes generating the electric field.

In an embodiment, a medical device for of treating a cancerous tumor is included having one or more implantable electrodes configured for placement on the inside of a body of a subject with the cancerous tumor; one or more external electrodes configured for placement on an outside surface of the body of the subject; an electric field generating circuit configured for generating an electric field between at least one pair of electrodes according to a predefined schedule, the electric field having frequencies within a range of between 10 kHz to 1 MHz; and control circuitry configured for receiving a pause command from the subject, wherein the pause command causes cessation of generating the electric field.

In an embodiment, a method for treating a cancerous tumor located within a subject is included, the method including applying one or more electric fields at or near a site of the cancerous tumor, the cancerous tumor can include a cancerous cell population; removing the one or more electric fields; administering an optically activated chemotherapeutic agent at or near a site of the cancerous tumor after the one or more electric fields have been removed; and irradiating the optically activated chemotherapeutic agent by delivering photoactivating light energy at or near the site of the cancerous tumor.

In an embodiment, the optically activated chemotherapeutic agent includes a therapeutically effective dose of optically activated chemotherapeutic agent for release at or near the site of the cancerous tumor.

In an embodiment, the therapeutically effective dose includes a concentrated dosage amount delivered to the subject within a 6-hour time period following removal of the electric field, the concentrated dosage amount being equivalent to a conventional non-concentrated dosage amount delivered over a 24-hour time period.

In an embodiment, the optically activated chemotherapeutic agent includes photoactivated platinum compounds or photoactivated photostatin compounds.

In an embodiment, the photoactivated photostatin compounds include light-activated combretastatin A-4, and analogs and derivatives thereof.

In an embodiment, the optically activated chemotherapeutic agent can be optically activated by visible light within the range of 350 nm to 850 nm.

In an embodiment, the optically activated chemotherapeutic agent can be optically inactivated by visible light within the range of 450 nm to 650 nm.

In an embodiment, a medical device for treating a cancerous tumor located within a subject is included having an electric field generating circuit configured to generate one or more electric fields at or near a site of the cancerous tumor, the cancerous tumor can include a cancerous cell population; control circuitry in communication with the electric field generating circuit, the control circuitry configured to control delivery of the one or more electric fields from the electric field generating circuit at or near the site of the cancerous tumor; a catheter configured to administer an optically activated chemotherapeutic agent at or near a site of the cancerous tumor; and a one or more optical emitters configured to irradiate the optically activated chemotherapeutic agent by delivering photoactivating light energy at or near the site of the cancerous tumor.

In an embodiment, a method for treating a cancerous tumor located within a subject is included, the method including applying one or more electric fields at or near a site of the cancerous tumor, the cancerous tumor can include a cancerous cell population; and administering nanoparticles can include a chemotherapeutic agent at or near the site of the cancerous tumor.

In an embodiment, a method can further include removing the one or more electric fields before administering the nanoparticles at or near the site of the cancerous tumor.

In an embodiment, the nanoparticles include a therapeutically effective dose of chemotherapeutic agent for release at or near the site of the cancerous tumor.

In an embodiment, the therapeutically effective dose includes a concentrated dosage amount delivered to the subject within a 6-hour time period following removal of the electric field, the concentrated dosage amount being equivalent to a conventional non-concentrated dosage amount delivered over a 24-hour time period.

In an embodiment, the chemotherapeutic agent includes at least one of vindesine, vincristine, vinblastine, paclitaxel, docetaxel, 2-methoxyestradiol, patupilone, trastuzumab emtansine, and derivatives thereof.

In an embodiment, the nanoparticles include a biodegradable polymer.

In an embodiment, a medical device for treating a cancerous tumor located within a subject is included having an electric field generating circuit configured to generate one or more electric fields at or near a site of the cancerous tumor, the cancerous tumor can include a cancerous cell population; control circuitry in communication with the electric field generating circuit, the control circuitry configured to control delivery of the one or more electric fields from the electric field generating circuit at or near the site of the cancerous tumor; and a catheter configured to administer an nanoparticles at or near a site of the cancerous tumor.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method for treating a cancerous tumor located within a subject comprising:

applying one or more electric fields at or near a site of the cancerous tumor, the cancerous tumor comprising a cancerous cell population;

wherein the one or more applied electric fields are effective to delay mitosis and cause mitotic synchronization within a proportion of the cancerous cell population;

receiving a pause command from the subject and/or a care provider, wherein the pause command causes cessation of the one or more electric fields to allow mitosis to proceed within the cancerous cell population;

reinitiating the one or more electric fields after a time period has elapsed after receiving the pause command, wherein the one or more electric fields is decreased by at least 50% for at least 4 hours; and administering a chemotherapeutic agent to the subject after the one or more electric fields have been removed.

2. The method of claim 1, wherein applying the one or more electric fields to the cancerous tumor comprises applying the one or more electric fields over a time period selected from a range of time periods from 1 minute to 24 hours.

3. The method of claim 1, further comprising administering the chemotherapeutic agent to the subject when at least 5% of the cancerous cell population is synchronized in mitosis in response to the one or more electric fields.

4. The method of claim 1, wherein the one or more electric fields are applied to the cancerous tumor at frequencies selected from a range of between 100 kHz to 300 kHz.

5. The method of claim 1, wherein the one or more electric fields comprise an electric field strength selected from a range of electric field strengths from 3 V/cm to 5 V/cm.

6. The method of claim 1, wherein the chemotherapeutic agent is administered to the subject in a therapeutically effective dose.

7. The method of claim 1, wherein applying the one or more electric fields to the subject comprises applying the one or more electric fields to an exterior of the subject at or near the site of the cancerous tumor.

8. The method of claim 1, wherein applying the one or more electric fields to the cancerous tumor comprises applying the one or more electric fields at least partially to an interior of the subject at or near the site of the cancerous tumor.

9. The method of claim 1, wherein applying the one or more electric fields to the cancerous tumor comprises applying the one or more electric fields at least partially to an exterior of the subject at or near the site of the cancerous tumor.

10. The method of claim 9, wherein the medical device further comprises one or more electrical leads in electrical communication with an electric field generating circuit.

11. The method of claim 10, wherein the one or more electrical leads comprise one or more optical emitters disposed along a length of the one or more electrical leads.

12. A method for treating a cancerous tumor located within a subject comprising:

applying a first electric field having at first field strength at or near a site of the cancerous tumor, the cancerous tumor comprising a cancerous cell population;

removing the first electric field to allow mitosis to proceed within the cancerous cell population;

applying a second electric field having a second field strength at or near the site of the cancerous tumor; and administering a chemotherapeutic agent to the subject after the first electric field and the second electric field have been removed;

wherein the first electric field and the second electric field are effective to delay mitosis and cause mitotic synchronization within a proportion of the cancerous cell population; and wherein the chemotherapeutic agent is administered to the subject 5 to 180 minutes after the first electric field and the second electric field have been removed.

13. A method for treating a cancerous tumor located within a subject comprising:

applying one or more electric fields at or near a site of the cancerous tumor, the cancerous tumor comprising a cancerous cell population;

wherein the one or more applied electric fields are effective to delay mitosis and cause mitotic synchronization within a proportion of the cancerous cell population;

removing the one or more electric fields to allow mitosis to proceed within the cancerous cell population; and administering the chemotherapeutic agent to the subject when at least 5% of the cancerous cell population is synchronized in mitosis in response to the one or more electric fields.

\* \* \* \* \*